(12) United States Patent
Pech et al.

(10) Patent No.: US 11,015,178 B2
(45) Date of Patent: *May 25, 2021

(54) ENZYMATIC SYNTHESIS OF L-NUCLEIC ACIDS

(71) Applicant: Aptarion Biotech AG, Berlin (DE)

(72) Inventors: Andreas Pech, Halle (DE); Ralf David, Leipzig (DE); Florian Jarosch, Berlin (DE); Michael Jahnz, Berlin (DE); Sven Klussmann, Berlin (DE)

(73) Assignee: APTARION biotech AG, Berlin (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/831,601

(22) Filed: Dec. 5, 2017

(65) Prior Publication Data
US 2018/0208910 A1    Jul. 26, 2018

Related U.S. Application Data

(63) Continuation of application No. 14/401,128, filed as application No. PCT/EP2013/001458 on May 16, 2013, now Pat. No. 9,850,471.

(30) Foreign Application Priority Data

May 16, 2012 (EP) .................... 12003887

(51) Int. Cl.
| | |
|---|---|
| C12N 9/12 | (2006.01) |
| C12N 15/115 | (2010.01) |
| C12P 19/34 | (2006.01) |
| C12N 15/10 | (2006.01) |

(52) U.S. Cl.
CPC ......... *C12N 9/1252* (2013.01); *C12N 9/1241* (2013.01); *C12N 15/1048* (2013.01); *C12N 15/115* (2013.01); *C12P 19/34* (2013.01); *C12Y 207/07007* (2013.01); *C12Y 207/07* (2013.01)

(58) Field of Classification Search
None
See application file for complete search history.

(56) References Cited

U.S. PATENT DOCUMENTS

| | | | |
|---|---|---|---|
| 6,605,713 | B1 | 8/2003 | Furste et al. |
| 9,850,471 | B2 | 12/2017 | Pech et al. |
| 2005/0196392 | A1 | 9/2005 | Anderson |
| 2006/0003326 | A1 | 1/2006 | Lange et al. |
| 2010/0081710 | A1 | 4/2010 | Lange et al. |

FOREIGN PATENT DOCUMENTS

| | | | | |
|---|---|---|---|---|
| DE | 10156274 | | 12/2003 | |
| WO | 03020969 | | 3/2003 | |
| WO | 03047743 | | 12/2003 | |
| WO | WO-2010050485 A1 | * | 5/2010 | ........... C07K 5/0215 |

OTHER PUBLICATIONS

Katoh et al., Consecutive Elongation of D-Amino Acids in Translation, Cell Chem. Biol., 2017, 24, 46-54.*
Sampson, Aptamers and Selex, World Patent Information, 2003, 25, 123-29.*
Jungbauer et al., Current status of technical protein refolding, J. Biotechnol., 2007, 128, 587-96.*
Yamaguchi et al., Protein refolding using chemical refolding additives, Biotechnol. J., 2012, 8, 17-31.*
English-language machine translation of WO 2010/050485, 2010.*
Wang et al., A synthetic molecular system capable of mirror-image genetic replication and transcription, Nat. Chem., 2016, 8, 698-704.*
Pisani et al., Domain organization and biochemical features of Sulfolobus solfataricus DNA polymerase, Extremophiles, 1998, 2, 171-77.*
Xu et al., Total chemical synthesis of a thermostable enzyme capable of polymerase chain reaction, Cell Discovery 3, 2017, 17008. (Year: 2017).*
GenBank AAA65326.1, 2014.
George Church, Life: What a Concept!, 14 pages, Aug. 27, 2007, Edge Foundation, Inc., https://www.edge.org/conversation/george_church-george-church%E2%80%941ife-what-a-concept.
James H. Brewster et al., Left-Handed Comments, 3 pages, Nov. 20, 1992, Science, 258:1289, US.
George Church, Fabricating with DNA, 22 pages, Aug. 22, 2007, FAB 4: The Fourth International Fab Lab Forum and Symposium on Digital Fabrication, http://cba.mit.edu/events/07.08.fab/Church.ppt.
Brewer & Laskowski, "Left-Handed Comments," Science 258:1289, 1992.
Brockman,ed., "Life: What a Concept," Edge 221, Sep. 4, 2007.
Church, "Fabricating with DNA," Fab Lab Forum & Dig Fab Symp, Aug. 22, 2007.
Oliveros et al., "Characterization . . . repair," JBC 272(49)30899-30910, 1997.
Boudsocq et al., "Solfolobus . . . pol," NAR 29(22)4607-4616, 2001.
PCT Search Report, dated 2013.
CN Search Report, dated 2013.
Vater et al.,"Turning . . . therapeutics," Drug Disc Today 20:147-155, 2015.

(Continued)

*Primary Examiner* — Robert B Mondesi
*Assistant Examiner* — Todd M Epstein
(74) *Attorney, Agent, or Firm* — MDIP LLC

(57) ABSTRACT

The present invention is related to a method for adding one or more L-nucleotides to the 3' end of a first L-nucleic acid, wherein the method comprises the step of reacting the one or more L-nucleotides with the first L-nucleic acid in the presence of a protein comprising an enzymatic activity exhibiting moiety, wherein the enzymatic activity is capable of adding one or more L-nucleotides to the 3' end of the first L-nucleic acid.

18 Claims, 26 Drawing Sheets
Specification includes a Sequence Listing.

(56) References Cited

OTHER PUBLICATIONS

Keefe et al., "Aptamers as therapeutics," Nat Rev 9:537-550, 2010.
Pentelute et al., "X-ray . . . enantiomers," J Am Chem Soc 130:9695-9701, 2008.
Milton et al., "Total . . . HIV-1," Science 256(5062)1445-1448, 1992.

* cited by examiner

Fig. 1A

|  | SP-1 (15-mer) D(g1)P (17-mer) |
|---|---|
| Complex 1-gap-A (D) | 5'-GATCACAGTGAGTAC GTAAAACGACGGCCAGT-3'<br>3'-CTAGTGTCACTCATG*A*CATTTTGCTGCCGGTCA-5'<br>MJ_1_140_DD (33-mer) |

SP-1 (15-mer)   D(g1)P (17-mer)
Complex 1-gap-C (D) 5'-GATCACAGTGAGTAC GTAAAACGACGGCCAGT-3'
               3'-CTAGTGTCACTCATG*C*CATTTTGCTGCCGGTCA-5'
                       MJ_1_141_DD (33-mer)

SP-1 (15-mer)   D(g1)P (17-mer)
Complex 1-gap-G (D)   5'-GATCACAGTGAGTAC GTAAAACGACGGCCAGT-3'
               3'-CTAGTGTCACTCATG*G*CATTTTGCTGCCGGTCA-5'
                       MJ_1_142_DD (33-mer)

SP-1 (15-mer)   D(g1)P (17-mer)
Complex 1-gap-T (D) 5'-GATCACAGTGAGTAC GTAAAACGACGGCCAGT-3'
               3'-CTAGTGTCACTCATG*T*CATTTTGCTGCCGGTCA-5'
                       SP1c+18(g1) (33-mer)

Fig. 1B

SP-1 (15-mer)     D(g6)P (12-mer)
Complex 6-gap (D):   5'-GATCACAGTGAGTAC    ACGACGGCCAGT-3'
               3'-CTAGTGTCACTCATGTTATCTTGCTGCCGGTCA-5'
                       SP1c+18(g6) (33-mer)

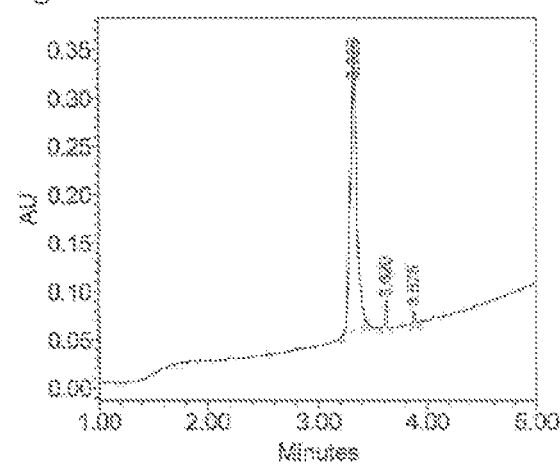

```
               MJ_1_58_MD (17-mer)  MJ_1_143_LD (17-mer)
Complex 1-gap-A (L) 5'-GG-GATCACAGTGAGTAC GTAAAACGACGGCCAGT-3'
                3'-    CTAGTGTCACTCATGACATTTTGCTGCCGGTCA-5'
                            MJ_1_145_LD (33-mer)

MJ_1_58_MD (17-mer)  MJ_1_143_LD (17-mer)
Complex 1-gap-C (L) 5'-GG-GATCACAGTGAGTAC GTAAAACGACGGCCAGT-3'
                3'-    CTAGTGTCACTCATGCCATTTTGCTGCCGGTCA-5'
                            MJ_1_146_LD (33-mer)

MJ_1_58_MD (17-mer)  MJ_1_143_LD (17-mer)
Complex 1-gap-G (L) 5'-GG-GATCACAGTGAGTAC GTAAAACGACGGCCAGT-3'
                3'-    CTAGTGTCACTCATGGCATTTTGCTGCCGGTCA-5'
                            MJ_1_147_LD (33-mer)

MJ_1_58_MD (17-mer)  MJ_1_143_LD (17-mer)
Complex 1-gap-T (L) 5'-GG-GATCACAGTGAGTAC GTAAAACGACGGCCAGT-3'
                3'-    CTAGTGTCACTCATGTCATTTTGCTGCCGGTCA-5'
                            MJ_1_144_LD (33-mer)
```

List of oligonucleotides for the 1-gap substrates:

| Name | nt | Configuration | Sequence (5'→3') |
|---|---|---|---|
| MJ_1_58_MD | 17 | first two G's = D, remainder = L | GG-GATCACAGTGAGTAC |
| MJ_1_143_LD | 17 | L | Phosphate-GTAAAACGACGGCCAGT |
| MJ_1_145_LD | 33 | L | ACTGGCCGTCGTTTTACAGTACTCACTGTGATC |
| MJ_1_146_LD | 33 | L | ACTGGCCGTCGTTTTACCGTACTCACTGTGATC |
| MJ_1_147_LD | 33 | L | ACTGGCCGTCGTTTTACGGTACTCACTGTGATC |
| MJ_1_144_LD | 33 | L | ACTGGCCGTCGTTTTACTGTACTCACTGTGATC |

Fig. 7

```
                    MJ_1_58_MD (17-mer)    MJ_1_59_LD (12-mer)
Complex 6-gap (L):  5'-GG-GATCACAGTGAGTAC    ACGACGGCCAGT-3'
                    3'- CTAGTGTCACTCATGTTATCTTGCTGCCGGTCA-5'
                                MJ_1_57_LD (33-mer)
```

List of oligonucleotides for the 6-gap substrates:

| Name | nt | Configuration | Sequence (5'→3') |
|---|---|---|---|
| MJ_1_58_MD | 17 | first two G's = D, remainder = L | GG-GATCACAGTGAGTAC |
| MJ_1_59_LD | 12 | L | Phosphate-ACGACGGCCAGT |
| MJ_1_57_LD | 33 | L | ACTGGCCGTCGTTCTATTGTACTCACTGTGATC |

Atto532---MJ_1_33_DD_19nt

MJ_1_1_DD_83nt 1 2 3 4 5 6 7 8 9

1: negative control (no polymerase)
2: positive control (Taq)
3: wild-type L-Polymerase X, 1.7 ng/µl
4: L-Pol-X V80G, 1.7 ng/µl
5: L-Pol-X V80G, 4 ng/µl
6: L-Pol-X V80G, 4 ng/µl (unpurified)
7: L-Pol-X V80A, 1.7 ng/µl
8: L-Pol-X V80A, 4 ng/µl
9: L-Pol-X V80A, 4 ng/µl (unpurified)

1: negative control (no polymerase)
2: wild-type L-Polymerase X, 5 thermal cycles
3: wild-type L-Polymerase X, 10 thermal cycles
4: wild-type L-Polymerase X, 15 thermal cycles
5: wild-type L-Polymerase X, 20 thermal cycles
6: wild-type L-Polymerase X, 25 thermal cycles
7: positive control (Taq)

Fig. 12A

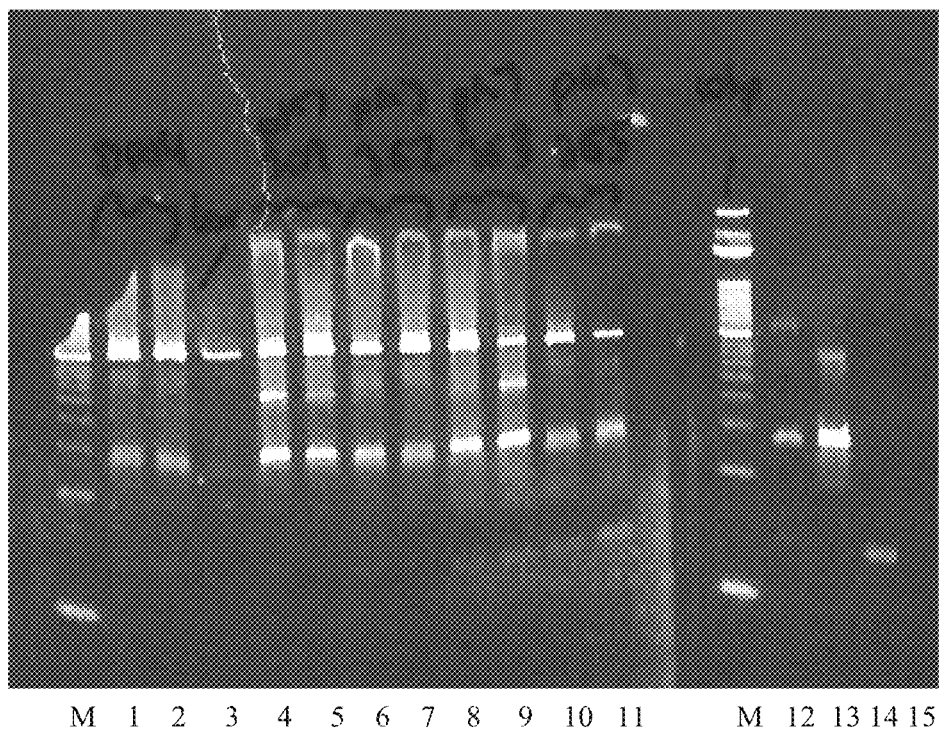

M  1  2  3  4  5  6  7  8  9  10  11    M  12  13  14  15

M: 10 bp DNA ladder (lowest visible band: 20 bp; 100 bp band more intense)
1: positive control, all-L-dpo4 from New England Biolabs (100 ng)
2: positive control, all-L-dpo4 from New England Biolabs (50 ng)
3: no sample loaded
4: all-L-polymerase dpo4 variant A155C (100 ng)
5: all-L-polymerase dpo4 variant A155C (50 ng)
6: all-L-polymerase dpo4 variant V203C (100 ng)
7: all-L-polymerase dpo4 variant V203C (50 ng)
8: all-L-polymerase dpo4 variant C31S (100 ng)
9: all-L-polymerase dpo4 variant C31S (50 ng)
10: all-L-polymerase dpo4 variant A155C/V203C (100 ng)
11: all-L-polymerase dpo4 variant A155C/V203C (50 ng)
12: negative control (template, fwd- and rev-primer)
13: fwd.-primer only
14: rev.-primer only
15: negative control (no template, no primers)

M: 50 bp DNA ladder (lowest band: 50 bp, then 100 bp)
1: negative control (without polymerase)
2: positive control; all-L-polymerase dpo4 (recombinant), 10 ng
3: all-L-polymerase dpo4 (synthetic), 10 ng
4: all-L-polymerase dpo4 (synthetic), 20 ng

SEQUENCE LISTING

<160> NUMBER OF SEQ ID NOS: 88

<210> SEQ ID NO 1
<211> LENGTH: 174
<212> TYPE: PRT

```
<213> ORGANISM: African swine fever virus
<220> FEATURE:
<221> NAME/KEY: MISC_FEATURE
<223> OTHER INFORMATION: Polymerase X

<400> SEQUENCE: 1

Met Leu Thr Leu Ile Gln Gly Lys Lys Ile Val Asn His Leu Arg Ser
1               5                   10                  15

Arg Leu Ala Phe Glu Tyr Asn Gly Gln Leu Ile Lys Ile Leu Ser Lys
            20                  25                  30

Asn Ile Val Ala Val Gly Ser Leu Arg Arg Glu Glu Lys Met Leu Asn
        35                  40                  45

Asp Val Asp Leu Leu Ile Ile Val Pro Glu Lys Lys Leu Leu Lys His
    50                  55                  60

Val Leu Pro Asn Ile Arg Ile Lys Gly Leu Ser Phe Ser Val Lys Val
65                  70                  75                  80

Cys Gly Glu Arg Lys Cys Val Leu Phe Ile Glu Trp Glu Lys Lys Thr
                85                  90                  95

Tyr Gln Leu Asp Leu Phe Thr Ala Leu Ala Glu Glu Lys Pro Tyr Ala
            100                 105                 110

Ile Phe His Phe Thr Gly Pro Val Ser Tyr Leu Ile Arg Ile Arg Ala
        115                 120                 125

Ala Leu Lys Lys Lys Asn Tyr Lys Leu Asn Gln Tyr Gly Leu Phe Lys
    130                 135                 140

Asn Gln Thr Leu Val Pro Leu Lys Ile Thr Thr Glu Lys Glu Leu Ile
145                 150                 155                 160

Lys Glu Leu Gly Phe Thr Tyr Arg Ile Pro Lys Lys Arg Leu
                165                 170

<210> SEQ ID NO 2
<211> LENGTH: 174
<212> TYPE: PRT
<213> ORGANISM: African swine fever virus
<220> FEATURE:
<221> NAME/KEY: MISC_FEATURE
<223> OTHER INFORMATION: Polymerase X variant

<400> SEQUENCE: 2

Met Leu Thr Leu Ile Gln Gly Lys Lys Ile Val Asn His Leu Arg Ser
1               5                   10                  15

Arg Leu Ala Phe Glu Tyr Asn Gly Gln Leu Ile Lys Ile Leu Ser Lys
            20                  25                  30

Asn Ile Val Ala Val Gly Ser Leu Arg Arg Glu Glu Lys Met Leu Asn
        35                  40                  45

Asp Val Asp Leu Leu Ile Ile Val Pro Glu Lys Lys Leu Leu Lys His
    50                  55                  60

Val Leu Pro Asn Ile Arg Ile Lys Gly Leu Ser Phe Ser Val Lys Gly
65                  70                  75                  80

Cys Gly Glu Arg Lys Cys Val Leu Phe Ile Glu Trp Glu Lys Lys Thr
                85                  90                  95

Tyr Gln Leu Asp Leu Phe Thr Ala Leu Ala Glu Glu Lys Pro Tyr Ala
            100                 105                 110

Ile Phe His Phe Thr Gly Pro Val Ser Tyr Leu Ile Arg Ile Arg Ala
        115                 120                 125

Ala Leu Lys Lys Lys Asn Tyr Lys Leu Asn Gln Tyr Gly Leu Phe Lys
    130                 135                 140

Asn Gln Thr Leu Val Pro Leu Lys Ile Thr Thr Glu Lys Glu Leu Ile
```

```
                    145                 150                 155                 160
Lys Glu Leu Gly Phe Thr Tyr Arg Ile Pro Lys Lys Arg Leu
                165                 170

<210> SEQ ID NO 3
<211> LENGTH: 174
<212> TYPE: PRT
<213> ORGANISM: African swine fever virus
<220> FEATURE:
<221> NAME/KEY: MISC_FEATURE
<223> OTHER INFORMATION: Polymerase X variant

<400> SEQUENCE: 3

Met Leu Thr Leu Ile Gln Gly Lys Lys Ile Val Asn His Leu Arg Ser
1               5                   10                  15

Arg Leu Ala Phe Glu Tyr Asn Gly Gln Leu Ile Lys Ile Leu Ser Lys
            20                  25                  30

Asn Ile Val Ala Val Gly Ser Leu Arg Arg Glu Glu Lys Met Leu Asn
        35                  40                  45

Asp Val Asp Leu Leu Ile Ile Val Pro Glu Lys Lys Leu Leu Lys His
    50                  55                  60

Val Leu Pro Asn Ile Arg Ile Lys Gly Leu Ser Phe Ser Val Lys Ala
65                  70                  75                  80

Cys Gly Glu Arg Lys Cys Val Leu Phe Ile Glu Trp Glu Lys Lys Thr
                85                  90                  95

Tyr Gln Leu Asp Leu Phe Thr Ala Leu Ala Glu Glu Lys Pro Tyr Ala
            100                 105                 110

Ile Phe His Phe Thr Gly Pro Val Ser Tyr Leu Ile Arg Ile Arg Ala
        115                 120                 125

Ala Leu Lys Lys Lys Asn Tyr Lys Leu Asn Gln Tyr Gly Leu Phe Lys
    130                 135                 140

Asn Gln Thr Leu Val Pro Leu Lys Ile Thr Thr Glu Lys Glu Leu Ile
145                 150                 155                 160

Lys Glu Leu Gly Phe Thr Tyr Arg Ile Pro Lys Lys Arg Leu
                165                 170

<210> SEQ ID NO 4
<211> LENGTH: 174
<212> TYPE: PRT
<213> ORGANISM: African swine fever virus
<220> FEATURE:
<221> NAME/KEY: MISC_FEATURE
<223> OTHER INFORMATION: Polymerase X variant

<400> SEQUENCE: 4

Met Leu Thr Leu Ile Gln Gly Lys Lys Ile Val Asn His Leu Arg Ser
1               5                   10                  15

Arg Leu Ala Phe Glu Tyr Asn Gly Gln Leu Ile Lys Ile Leu Ser Lys
            20                  25                  30

Asn Ile Val Ala Val Gly Ser Leu Arg Arg Glu Glu Lys Met Leu Asn
        35                  40                  45

Asp Val Asp Leu Leu Ile Ile Val Pro Glu Lys Lys Leu Leu Lys His
    50                  55                  60

Val Leu Pro Asn Ile Arg Ile Lys Gly Leu Ser Phe Ser Val Lys Val
65                  70                  75                  80

Cys Gly Glu Arg Lys Cys Val Leu Phe Ile Glu Trp Glu Lys Lys Thr
                85                  90                  95

Tyr Gln Leu Asp Leu Phe Thr Ala Leu Ala Glu Glu Lys Pro Tyr Ala
```

```
            100                 105                 110
Ile Phe His Phe Thr Gly Pro Val Ser Tyr Leu Gly Arg Ile Arg Ala
            115                 120                 125

Ala Leu Lys Lys Lys Asn Tyr Lys Leu Asn Gln Tyr Gly Leu Phe Lys
            130                 135             140

Asn Gln Thr Leu Val Pro Leu Lys Ile Thr Thr Glu Lys Glu Leu Ile
145                 150                 155                 160

Lys Glu Leu Gly Phe Thr Tyr Arg Ile Pro Lys Lys Arg Leu
                165                 170
```

<210> SEQ ID NO 5
<211> LENGTH: 174
<212> TYPE: PRT
<213> ORGANISM: African swine fever virus
<220> FEATURE:
<221> NAME/KEY: MISC_FEATURE
<223> OTHER INFORMATION: Polymerase X variant

<400> SEQUENCE: 5

```
Met Leu Thr Leu Ile Gln Gly Lys Lys Ile Val Asn His Leu Arg Ser
1               5                   10                  15

Arg Leu Ala Phe Glu Tyr Asn Gly Gln Leu Ile Lys Ile Leu Ser Lys
            20                  25                  30

Asn Ile Val Ala Val Gly Ser Leu Arg Arg Glu Glu Lys Met Leu Asn
        35                  40                  45

Asp Val Asp Leu Leu Ile Ile Val Pro Glu Lys Lys Leu Leu Lys His
    50                  55                  60

Val Leu Pro Asn Ile Arg Ile Lys Gly Leu Ser Phe Ser Val Lys Val
65                  70                  75                  80

Cys Gly Glu Arg Lys Ser Val Leu Phe Ile Glu Trp Glu Lys Lys Thr
                85                  90                  95

Tyr Gln Leu Asp Leu Phe Thr Ala Leu Ala Glu Glu Lys Pro Tyr Ala
            100                 105                 110

Ile Phe His Phe Thr Gly Pro Val Ser Tyr Leu Ile Arg Ile Arg Ala
            115                 120                 125

Ala Leu Lys Lys Lys Asn Tyr Lys Leu Asn Gln Tyr Gly Leu Phe Lys
            130                 135             140

Asn Gln Thr Leu Val Pro Leu Lys Ile Thr Thr Glu Lys Glu Leu Ile
145                 150                 155                 160

Lys Glu Leu Gly Phe Thr Tyr Arg Ile Pro Lys Lys Arg Leu
                165                 170
```

<210> SEQ ID NO 6
<211> LENGTH: 17
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(2)
<223> OTHER INFORMATION: D-nucleotides
<220> FEATURE:
<221> NAME/KEY: misc_feature
<222> LOCATION: (3)..(17)
<223> OTHER INFORMATION: L-nucleotides

<400> SEQUENCE: 6
gggatcacag tgagtac                                              17

```
<210> SEQ ID NO 7
<211> LENGTH: 17
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(17)
<223> OTHER INFORMATION: L-nucleotides
<220> FEATURE:
<221> NAME/KEY: misc_feature
<222> LOCATION: (1)..(1)
<223> OTHER INFORMATION: Phosphate attached

<400> SEQUENCE: 7
gtaaaacgac ggccagt                                                17

<210> SEQ ID NO 8
<211> LENGTH: 33
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(33)
<223> OTHER INFORMATION: L-nucleotides

<400> SEQUENCE: 8
actggccgtc gttttacagt actcactgtg atc                              33

<210> SEQ ID NO 9
<211> LENGTH: 33
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(33)
<223> OTHER INFORMATION: L-nucleotides

<400> SEQUENCE: 9
actggccgtc gttttaccgt actcactgtg atc                              33

<210> SEQ ID NO 10
<211> LENGTH: 33
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(33)
<223> OTHER INFORMATION: L-nucleotides

<400> SEQUENCE: 10
actggccgtc gttttacggt actcactgtg atc                              33

<210> SEQ ID NO 11
<211> LENGTH: 33
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(33)
<223> OTHER INFORMATION: L-nucleotides
```

```
<400> SEQUENCE: 11
actggccgtc gttttactgt actcactgtg atc                        33

<210> SEQ ID NO 12
<211> LENGTH: 17
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(2)
<223> OTHER INFORMATION: D-nucleotides
<220> FEATURE:
<221> NAME/KEY: misc_feature
<222> LOCATION: (3)..(17)
<223> OTHER INFORMATION: L-nucleotides

<400> SEQUENCE: 12
gggatcacag tgagtac                                          17

<210> SEQ ID NO 13
<211> LENGTH: 12
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(12)
<223> OTHER INFORMATION: L-nucleotides
<220> FEATURE:
<221> NAME/KEY: misc_feature
<222> LOCATION: (1)..(1)
<223> OTHER INFORMATION: Phosphate attached

<400> SEQUENCE: 13
acgacggcca gt                                               12

<210> SEQ ID NO 14
<211> LENGTH: 33
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(33)
<223> OTHER INFORMATION: L-nucleotides

<400> SEQUENCE: 14
actggccgtc gttctattgt actcactgtg atc                        33

<210> SEQ ID NO 15
<211> LENGTH: 352
<212> TYPE: PRT
<213> ORGANISM: Sulfolobus solfataricus
<220> FEATURE:
<221> NAME/KEY: MISC_FEATURE
<223> OTHER INFORMATION: Polymerase Dpo4

<400> SEQUENCE: 15

Met Ile Val Leu Phe Val Asp Phe Asp Tyr Phe Tyr Ala Gln Val Glu
 1               5                  10                  15

Glu Val Leu Asn Pro Ser Leu Lys Gly Lys Pro Val Val Val Cys Val
            20                  25                  30

Phe Ser Gly Arg Phe Glu Asp Ser Gly Ala Val Ala Thr Ala Asn Tyr
        35                  40                  45
```

```
Glu Ala Arg Lys Phe Gly Val Lys Ala Gly Ile Pro Ile Val Glu Ala
            50                  55                  60

Lys Lys Ile Leu Pro Asn Ala Val Tyr Leu Pro Met Arg Lys Glu Val
 65                  70                  75                  80

Tyr Gln Gln Val Ser Ser Arg Ile Met Asn Leu Leu Arg Glu Tyr Ser
                85                  90                  95

Glu Lys Ile Glu Ile Ala Ser Ile Asp Glu Ala Tyr Leu Asp Ile Ser
            100                 105                 110

Asp Lys Val Arg Asp Tyr Arg Glu Ala Tyr Asn Leu Gly Leu Glu Ile
            115                 120                 125

Lys Asn Lys Ile Leu Glu Lys Glu Lys Ile Thr Val Thr Val Gly Ile
130                 135                 140

Ser Lys Asn Lys Val Phe Ala Lys Ile Ala Ala Asp Met Ala Lys Pro
145                 150                 155                 160

Asn Gly Ile Lys Val Ile Asp Asp Glu Glu Val Lys Arg Leu Ile Arg
                165                 170                 175

Glu Leu Asp Ile Ala Asp Val Pro Gly Ile Gly Asn Ile Thr Ala Glu
            180                 185                 190

Lys Leu Lys Lys Leu Gly Ile Asn Lys Leu Val Asp Thr Leu Ser Ile
            195                 200                 205

Glu Phe Asp Lys Leu Lys Gly Met Ile Gly Glu Ala Lys Ala Lys Tyr
            210                 215                 220

Leu Ile Ser Leu Ala Arg Asp Glu Tyr Asn Glu Pro Ile Arg Thr Arg
225                 230                 235                 240

Val Arg Lys Ser Ile Gly Arg Ile Val Thr Met Lys Arg Asn Ser Arg
                245                 250                 255

Asn Leu Glu Glu Ile Lys Pro Tyr Leu Phe Arg Ala Ile Glu Glu Ser
            260                 265                 270

Tyr Tyr Lys Leu Asp Lys Arg Ile Pro Lys Ala Ile His Val Val Ala
            275                 280                 285

Val Thr Glu Asp Leu Asp Ile Val Ser Arg Gly Arg Thr Phe Pro His
            290                 295                 300

Gly Ile Ser Lys Glu Thr Ala Tyr Ser Glu Ser Val Lys Leu Leu Gln
305                 310                 315                 320

Lys Ile Leu Glu Glu Asp Glu Arg Lys Ile Arg Arg Ile Gly Val Arg
                325                 330                 335

Phe Ser Lys Phe Ile Glu Ala Ile Gly Leu Asp Lys Phe Phe Asp Thr
            340                 345                 350

<210> SEQ ID NO 16
<211> LENGTH: 352
<212> TYPE: PRT
<213> ORGANISM: Sulfolobus solfataricus
<220> FEATURE:
<221> NAME/KEY: MISC_FEATURE
<223> OTHER INFORMATION: Polymerase Dpo4 variant

<400> SEQUENCE: 16

Met Ile Val Leu Phe Val Asp Phe Asp Tyr Phe Tyr Ala Gln Val Glu
1               5                   10                  15

Glu Val Leu Asn Pro Ser Leu Lys Gly Lys Pro Val Val Val Cys Val
                20                  25                  30

Phe Ser Gly Arg Phe Glu Asp Ser Gly Ala Val Ala Thr Ala Asn Tyr
            35                  40                  45

Glu Ala Arg Lys Phe Gly Val Lys Ala Gly Ile Pro Ile Val Glu Ala
```

-continued

```
            50                  55                  60
Lys Lys Ile Leu Pro Asn Ala Val Tyr Leu Pro Met Arg Lys Glu Val
 65                  70                  75                  80

Tyr Gln Gln Val Ser Ser Arg Ile Met Asn Leu Leu Arg Glu Tyr Ser
                 85                  90                  95

Glu Lys Ile Glu Ile Ala Ser Ile Asp Glu Ala Tyr Leu Asp Ile Ser
                100                 105                 110

Asp Lys Val Arg Asp Tyr Arg Glu Ala Tyr Asn Leu Gly Leu Glu Ile
            115                 120                 125

Lys Asn Lys Ile Leu Glu Lys Glu Lys Ile Thr Val Thr Val Gly Ile
        130                 135                 140

Ser Lys Asn Lys Val Phe Ala Lys Ile Ala Cys Asp Met Ala Lys Pro
145                 150                 155                 160

Asn Gly Ile Lys Val Ile Asp Asp Glu Val Lys Arg Leu Ile Arg
                165                 170                 175

Glu Leu Asp Ile Ala Asp Val Pro Gly Ile Gly Asn Ile Thr Ala Glu
                180                 185                 190

Lys Leu Lys Lys Leu Gly Ile Asn Lys Leu Val Asp Thr Leu Ser Ile
            195                 200                 205

Glu Phe Asp Lys Leu Lys Gly Met Ile Gly Glu Ala Lys Ala Lys Tyr
210                 215                 220

Leu Ile Ser Leu Ala Arg Asp Glu Tyr Asn Glu Pro Ile Arg Thr Arg
225                 230                 235                 240

Val Arg Lys Ser Ile Gly Arg Ile Val Thr Met Lys Arg Asn Ser Arg
                245                 250                 255

Asn Leu Glu Glu Ile Lys Pro Tyr Leu Phe Arg Ala Ile Glu Glu Ser
                260                 265                 270

Tyr Tyr Lys Leu Asp Lys Arg Ile Pro Lys Ala Ile His Val Val Ala
            275                 280                 285

Val Thr Glu Asp Leu Asp Ile Val Ser Arg Gly Arg Thr Phe Pro His
        290                 295                 300

Gly Ile Ser Lys Glu Thr Ala Tyr Ser Glu Ser Val Lys Leu Leu Gln
305                 310                 315                 320

Lys Ile Leu Glu Glu Asp Glu Arg Lys Ile Arg Arg Ile Gly Val Arg
                325                 330                 335

Phe Ser Lys Phe Ile Glu Ala Ile Gly Leu Asp Lys Phe Phe Asp Thr
                340                 345                 350
```

<210> SEQ ID NO 17
<211> LENGTH: 352
<212> TYPE: PRT
<213> ORGANISM: Sulfolobus solfataricus
<220> FEATURE:
<221> NAME/KEY: MISC_FEATURE
<223> OTHER INFORMATION: Polmyerase Dpo4 variant

<400> SEQUENCE: 17

```
Met Ile Val Leu Phe Val Asp Phe Asp Tyr Phe Tyr Ala Gln Val Glu
 1               5                  10                  15

Glu Val Leu Asn Pro Ser Leu Lys Gly Lys Pro Val Val Val Cys Val
                20                  25                  30

Phe Ser Gly Arg Phe Glu Asp Ser Gly Ala Val Ala Thr Ala Asn Tyr
            35                  40                  45

Glu Ala Arg Lys Phe Gly Val Lys Ala Gly Ile Pro Ile Val Glu Ala
        50                  55                  60
```

-continued

```
Lys Lys Ile Leu Pro Asn Ala Val Tyr Leu Pro Met Arg Lys Glu Val
 65                  70                  75                  80

Tyr Gln Gln Val Ser Ser Arg Ile Met Asn Leu Leu Arg Glu Tyr Ser
                 85                  90                  95

Glu Lys Ile Glu Ile Ala Ser Ile Asp Glu Ala Tyr Leu Asp Ile Ser
            100                 105                 110

Asp Lys Val Arg Asp Tyr Arg Glu Ala Tyr Asn Leu Gly Leu Glu Ile
        115                 120                 125

Lys Asn Lys Ile Leu Glu Lys Glu Lys Ile Thr Val Thr Val Gly Ile
    130                 135                 140

Ser Lys Asn Lys Val Phe Ala Lys Ile Ala Ala Asp Met Ala Lys Pro
145                 150                 155                 160

Asn Gly Ile Lys Val Ile Asp Asp Glu Glu Val Lys Arg Leu Ile Arg
                165                 170                 175

Glu Leu Asp Ile Ala Asp Val Pro Gly Ile Gly Asn Ile Thr Ala Glu
            180                 185                 190

Lys Leu Lys Lys Leu Gly Ile Asn Lys Leu Cys Asp Thr Leu Ser Ile
        195                 200                 205

Glu Phe Asp Lys Leu Lys Gly Met Ile Gly Glu Ala Lys Ala Lys Tyr
    210                 215                 220

Leu Ile Ser Leu Ala Arg Asp Glu Tyr Asn Glu Pro Ile Arg Thr Arg
225                 230                 235                 240

Val Arg Lys Ser Ile Gly Arg Ile Val Thr Met Lys Arg Asn Ser Arg
                245                 250                 255

Asn Leu Glu Glu Ile Lys Pro Tyr Leu Phe Arg Ala Ile Glu Glu Ser
            260                 265                 270

Tyr Tyr Lys Leu Asp Lys Arg Ile Pro Lys Ala Ile His Val Val Ala
        275                 280                 285

Val Thr Glu Asp Leu Asp Ile Val Ser Arg Gly Arg Thr Phe Pro His
    290                 295                 300

Gly Ile Ser Lys Glu Thr Ala Tyr Ser Glu Ser Val Lys Leu Leu Gln
305                 310                 315                 320

Lys Ile Leu Glu Glu Asp Glu Arg Lys Ile Arg Arg Ile Gly Val Arg
                325                 330                 335

Phe Ser Lys Phe Ile Glu Ala Ile Gly Leu Asp Lys Phe Phe Asp Thr
            340                 345                 350

<210> SEQ ID NO 18
<211> LENGTH: 352
<212> TYPE: PRT
<213> ORGANISM: Sulfolobus solfataricus
<220> FEATURE:
<221> NAME/KEY: MISC_FEATURE
<223> OTHER INFORMATION: Polymerase Dpo4 variant

<400> SEQUENCE: 18

Met Ile Val Leu Phe Val Asp Phe Asp Tyr Phe Tyr Ala Gln Val Glu
  1               5                  10                  15

Glu Val Leu Asn Pro Ser Leu Lys Gly Lys Pro Val Val Val Cys Val
             20                  25                  30

Phe Ser Gly Arg Phe Glu Asp Ser Gly Ala Val Ala Thr Ala Asn Tyr
         35                  40                  45

Glu Ala Arg Lys Phe Gly Val Lys Ala Gly Ile Pro Ile Val Glu Ala
     50                  55                  60

Lys Lys Ile Leu Pro Asn Ala Val Tyr Leu Pro Met Arg Lys Glu Val
 65                  70                  75                  80
```

Tyr Gln Gln Val Ser Ser Arg Ile Met Asn Leu Leu Arg Glu Tyr Ser
                85                  90                  95

Glu Lys Ile Glu Ile Ala Ser Ile Asp Glu Ala Tyr Leu Asp Ile Ser
            100                 105                 110

Asp Lys Val Arg Asp Tyr Arg Glu Ala Tyr Asn Leu Gly Leu Glu Ile
        115                 120                 125

Lys Asn Lys Ile Leu Glu Lys Glu Lys Ile Thr Val Thr Val Gly Ile
    130                 135                 140

Ser Lys Asn Lys Val Phe Ala Lys Ile Ala Cys Asp Met Ala Lys Pro
145                 150                 155                 160

Asn Gly Ile Lys Val Ile Asp Asp Glu Val Lys Arg Leu Ile Arg
                165                 170                 175

Glu Leu Asp Ile Ala Asp Val Pro Gly Ile Gly Asn Ile Thr Ala Glu
            180                 185                 190

Lys Leu Lys Lys Leu Gly Ile Asn Lys Leu Cys Asp Thr Leu Ser Ile
    195                 200                 205

Glu Phe Asp Lys Leu Lys Gly Met Ile Gly Glu Ala Lys Ala Lys Tyr
210                 215                 220

Leu Ile Ser Leu Ala Arg Asp Glu Tyr Asn Glu Pro Ile Arg Thr Arg
225                 230                 235                 240

Val Arg Lys Ser Ile Gly Arg Ile Val Thr Met Lys Arg Asn Ser Arg
                245                 250                 255

Asn Leu Glu Glu Ile Lys Pro Tyr Leu Phe Arg Ala Ile Glu Glu Ser
            260                 265                 270

Tyr Tyr Lys Leu Asp Lys Arg Ile Pro Lys Ala Ile His Val Val Ala
        275                 280                 285

Val Thr Glu Asp Leu Asp Ile Val Ser Arg Gly Arg Thr Phe Pro His
    290                 295                 300

Gly Ile Ser Lys Glu Thr Ala Tyr Ser Glu Ser Val Lys Leu Leu Gln
305                 310                 315                 320

Lys Ile Leu Glu Glu Asp Glu Arg Lys Ile Arg Arg Ile Gly Val Arg
                325                 330                 335

Phe Ser Lys Phe Ile Glu Ala Ile Gly Leu Asp Lys Phe Asp Thr
            340                 345                 350

<210> SEQ ID NO 19
<211> LENGTH: 352
<212> TYPE: PRT
<213> ORGANISM: Sulfolobus solfataricus
<220> FEATURE:
<221> NAME/KEY: MISC_FEATURE
<223> OTHER INFORMATION: Polymerase Dpo4 variant

<400> SEQUENCE: 19

Met Ile Val Leu Phe Val Asp Phe Asp Tyr Phe Tyr Ala Gln Val Glu
1               5                   10                  15

Glu Val Leu Asn Pro Ser Leu Lys Gly Lys Pro Val Val Val Ser Val
            20                  25                  30

Phe Ser Gly Arg Phe Glu Asp Ser Gly Ala Val Ala Thr Ala Asn Tyr
        35                  40                  45

Glu Ala Arg Lys Phe Gly Val Lys Ala Gly Ile Pro Ile Val Glu Ala
    50                  55                  60

Lys Lys Ile Leu Pro Asn Ala Val Tyr Leu Pro Met Arg Lys Glu Val
65                  70                  75                  80

Tyr Gln Gln Val Ser Ser Arg Ile Met Asn Leu Leu Arg Glu Tyr Ser

```
            85                  90                  95
Glu Lys Ile Glu Ile Ala Ser Ile Asp Glu Ala Tyr Leu Asp Ile Ser
            100                 105                 110

Asp Lys Val Arg Asp Tyr Arg Glu Ala Tyr Asn Leu Gly Leu Glu Ile
            115                 120                 125

Lys Asn Lys Ile Leu Glu Lys Glu Lys Ile Thr Val Thr Val Gly Ile
            130                 135                 140

Ser Lys Asn Lys Val Phe Ala Lys Ile Ala Ala Asp Met Ala Lys Pro
145                 150                 155                 160

Asn Gly Ile Lys Val Ile Asp Asp Glu Glu Val Lys Arg Leu Ile Arg
            165                 170                 175

Glu Leu Asp Ile Ala Asp Val Pro Gly Ile Gly Asn Ile Thr Ala Glu
            180                 185                 190

Lys Leu Lys Lys Leu Gly Ile Asn Lys Leu Val Asp Thr Leu Ser Ile
            195                 200                 205

Glu Phe Asp Lys Leu Lys Gly Met Ile Gly Glu Ala Lys Ala Lys Tyr
            210                 215                 220

Leu Ile Ser Leu Ala Arg Asp Glu Tyr Asn Glu Pro Ile Arg Thr Arg
225                 230                 235                 240

Val Arg Lys Ser Ile Gly Arg Ile Val Thr Met Lys Arg Asn Ser Arg
            245                 250                 255

Asn Leu Glu Glu Ile Lys Pro Tyr Leu Phe Arg Ala Ile Glu Glu Ser
            260                 265                 270

Tyr Tyr Lys Leu Asp Lys Arg Ile Pro Lys Ala Ile His Val Val Ala
            275                 280                 285

Val Thr Glu Asp Leu Asp Ile Val Ser Arg Gly Arg Thr Phe Pro His
            290                 295                 300

Gly Ile Ser Lys Glu Thr Ala Tyr Ser Glu Ser Val Lys Leu Leu Gln
305                 310                 315                 320

Lys Ile Leu Glu Glu Asp Glu Arg Lys Ile Arg Arg Ile Gly Val Arg
            325                 330                 335

Phe Ser Lys Phe Ile Glu Ala Ile Gly Leu Asp Lys Phe Phe Asp Thr
            340                 345                 350

<210> SEQ ID NO 20
<211> LENGTH: 352
<212> TYPE: PRT
<213> ORGANISM: Sulfolobus solfataricus
<220> FEATURE:
<221> NAME/KEY: MISC_FEATURE
<223> OTHER INFORMATION: Polymerase Dpo4 variant

<400> SEQUENCE: 20

Met Ile Val Leu Phe Val Asp Phe Asp Tyr Phe Tyr Ala Gln Val Glu
1               5                   10                  15

Glu Val Leu Asn Pro Ser Leu Lys Gly Lys Pro Val Val Val Cys Val
            20                  25                  30

Phe Ser Gly Arg Phe Glu Asp Ser Gly Ala Val Ala Thr Ala Asn Tyr
            35                  40                  45

Glu Ala Arg Lys Phe Gly Val Lys Ala Gly Ile Pro Ile Val Glu Ala
            50                  55                  60

Lys Lys Ile Leu Pro Asn Ala Val Tyr Leu Pro Met Arg Lys Glu Val
65                  70                  75                  80

Tyr Gln Gln Val Cys Ser Arg Ile Met Asn Leu Leu Arg Glu Tyr Ser
            85                  90                  95
```

```
Glu Lys Ile Glu Ile Ala Ser Ile Asp Glu Ala Tyr Leu Asp Ile Ser
                100                 105                 110

Asp Lys Val Arg Asp Tyr Arg Glu Ala Tyr Asn Leu Gly Leu Glu Ile
            115                 120                 125

Lys Asn Lys Ile Leu Glu Lys Glu Lys Ile Thr Val Thr Val Gly Ile
        130                 135                 140

Ser Lys Asn Lys Val Phe Ala Lys Ile Ala Ala Asp Met Ala Lys Pro
145                 150                 155                 160

Asn Gly Ile Lys Val Ile Asp Asp Glu Val Lys Arg Leu Ile Arg
                165                 170                 175

Glu Leu Asp Ile Ala Asp Val Pro Gly Ile Gly Asn Ile Thr Ala Glu
            180                 185                 190

Lys Leu Lys Lys Leu Gly Ile Asn Lys Leu Val Asp Thr Leu Ser Ile
        195                 200                 205

Glu Phe Asp Lys Leu Lys Gly Met Ile Gly Glu Ala Lys Ala Lys Tyr
210                 215                 220

Leu Ile Ser Leu Ala Arg Asp Glu Tyr Asn Glu Pro Ile Arg Thr Arg
225                 230                 235                 240

Val Arg Lys Ser Ile Gly Arg Ile Val Thr Met Lys Arg Asn Ser Arg
                245                 250                 255

Asn Leu Glu Glu Ile Lys Pro Tyr Leu Phe Arg Ala Ile Glu Glu Ser
            260                 265                 270

Tyr Tyr Lys Leu Asp Lys Arg Ile Pro Lys Ala Ile His Val Val Ala
        275                 280                 285

Val Thr Glu Asp Leu Asp Ile Val Ser Arg Gly Arg Thr Phe Pro His
290                 295                 300

Gly Ile Ser Lys Glu Thr Ala Tyr Ser Glu Ser Val Lys Leu Leu Gln
305                 310                 315                 320

Lys Ile Leu Glu Glu Asp Glu Arg Lys Ile Arg Ile Gly Val Arg
                325                 330                 335

Phe Ser Lys Phe Ile Glu Ala Ile Gly Leu Asp Lys Phe Asp Thr
            340                 345                 350

<210> SEQ ID NO 21
<211> LENGTH: 352
<212> TYPE: PRT
<213> ORGANISM: Sulfolobus solfataricus
<220> FEATURE:
<221> NAME/KEY: MISC_FEATURE
<223> OTHER INFORMATION: Polymerase Dpo4 variant

<400> SEQUENCE: 21

Met Ile Val Leu Phe Val Asp Phe Asp Tyr Phe Tyr Ala Gln Val Glu
1               5                   10                  15

Glu Val Leu Asn Pro Ser Leu Lys Gly Lys Pro Val Val Val Cys Val
            20                  25                  30

Phe Ser Gly Arg Phe Glu Asp Ser Gly Ala Val Ala Thr Ala Asn Tyr
        35                  40                  45

Glu Ala Arg Lys Phe Gly Val Lys Ala Gly Ile Pro Ile Val Glu Ala
    50                  55                  60

Lys Lys Ile Leu Pro Asn Ala Val Tyr Leu Pro Met Arg Lys Glu Val
65                  70                  75                  80

Tyr Gln Gln Val Ser Cys Arg Ile Met Asn Leu Leu Arg Glu Tyr Ser
                85                  90                  95

Glu Lys Ile Glu Ile Ala Ser Ile Asp Glu Ala Tyr Leu Asp Ile Ser
                100                 105                 110
```

```
Asp Lys Val Arg Asp Tyr Arg Glu Ala Tyr Asn Leu Gly Leu Glu Ile
                115                 120                 125

Lys Asn Lys Ile Leu Glu Lys Glu Lys Ile Thr Val Thr Val Gly Ile
        130                 135                 140

Ser Lys Asn Lys Val Phe Ala Lys Ile Ala Ala Asp Met Ala Lys Pro
145                 150                 155                 160

Asn Gly Ile Lys Val Ile Asp Asp Glu Val Lys Arg Leu Ile Arg
                165                 170                 175

Glu Leu Asp Ile Ala Asp Val Pro Gly Ile Gly Asn Ile Thr Ala Glu
                180                 185                 190

Lys Leu Lys Lys Leu Gly Ile Asn Lys Leu Val Asp Thr Leu Ser Ile
        195                 200                 205

Glu Phe Asp Lys Leu Lys Gly Met Ile Gly Glu Ala Lys Ala Lys Tyr
210                 215                 220

Leu Ile Ser Leu Ala Arg Asp Glu Tyr Asn Glu Pro Ile Arg Thr Arg
225                 230                 235                 240

Val Arg Lys Ser Ile Gly Arg Ile Val Thr Met Lys Arg Asn Ser Arg
                245                 250                 255

Asn Leu Glu Glu Ile Lys Pro Tyr Leu Phe Arg Ala Ile Glu Glu Ser
                260                 265                 270

Tyr Tyr Lys Leu Asp Lys Arg Ile Pro Lys Ala Ile His Val Val Ala
        275                 280                 285

Val Thr Glu Asp Leu Asp Ile Val Ser Arg Gly Arg Thr Phe Pro His
        290                 295                 300

Gly Ile Ser Lys Glu Thr Ala Tyr Ser Glu Ser Val Lys Leu Leu Gln
305                 310                 315                 320

Lys Ile Leu Glu Glu Asp Glu Arg Lys Ile Arg Arg Ile Gly Val Arg
                325                 330                 335

Phe Ser Lys Phe Ile Glu Ala Ile Gly Leu Asp Lys Phe Phe Asp Thr
                340                 345                 350

<210> SEQ ID NO 22
<211> LENGTH: 352
<212> TYPE: PRT
<213> ORGANISM: Sulfolobus solfataricus
<220> FEATURE:
<221> NAME/KEY: MISC_FEATURE
<223> OTHER INFORMATION: Polymerase Dpo4 variant

<400> SEQUENCE: 22

Met Ile Val Leu Phe Val Asp Phe Asp Tyr Phe Tyr Ala Gln Val Glu
1               5                   10                  15

Glu Val Leu Asn Pro Ser Leu Lys Gly Lys Pro Val Val Val Cys Val
                20                  25                  30

Phe Ser Gly Arg Phe Glu Asp Ser Gly Ala Val Ala Thr Ala Asn Tyr
        35                  40                  45

Glu Ala Arg Lys Phe Gly Val Lys Ala Gly Ile Pro Ile Val Glu Ala
        50                  55                  60

Lys Lys Ile Leu Pro Asn Ala Val Tyr Leu Pro Met Arg Lys Glu Val
65                  70                  75                  80

Tyr Gln Gln Val Ser Ser Arg Ile Met Asn Leu Leu Arg Glu Tyr Cys
                85                  90                  95

Glu Lys Ile Glu Ile Ala Ser Ile Asp Glu Ala Tyr Leu Asp Ile Ser
                100                 105                 110

Asp Lys Val Arg Asp Tyr Arg Glu Ala Tyr Asn Leu Gly Leu Glu Ile
```

|     |     |     |     |     | 115 |     |     |     |     | 120 |     |     |     |     | 125 |     |
| --- | --- | --- | --- | --- | --- | --- | --- | --- | --- | --- | --- | --- | --- | --- | --- | --- |
Lys Asn Lys Ile Leu Glu Lys Glu Lys Ile Thr Val Thr Val Gly Ile
            130                    135                    140

Ser Lys Asn Lys Val Phe Ala Lys Ile Ala Ala Asp Met Ala Lys Pro
145                    150                    155                    160

Asn Gly Ile Lys Val Ile Asp Asp Glu Val Lys Arg Leu Ile Arg
            165                    170                    175

Glu Leu Asp Ile Ala Asp Val Pro Gly Ile Gly Asn Ile Thr Ala Glu
            180                    185                    190

Lys Leu Lys Lys Leu Gly Ile Asn Lys Leu Val Asp Thr Leu Ser Ile
            195                    200                    205

Glu Phe Asp Lys Leu Lys Gly Met Ile Gly Glu Ala Lys Ala Lys Tyr
210                    215                    220

Leu Ile Ser Leu Ala Arg Asp Glu Tyr Asn Glu Pro Ile Arg Thr Arg
225                    230                    235                    240

Val Arg Lys Ser Ile Gly Arg Ile Val Thr Met Lys Arg Asn Ser Arg
            245                    250                    255

Asn Leu Glu Glu Ile Lys Pro Tyr Leu Phe Arg Ala Ile Glu Glu Ser
            260                    265                    270

Tyr Tyr Lys Leu Asp Lys Arg Ile Pro Lys Ala Ile His Val Val Ala
            275                    280                    285

Val Thr Glu Asp Leu Asp Ile Val Ser Arg Gly Arg Thr Phe Pro His
290                    295                    300

Gly Ile Ser Lys Glu Thr Ala Tyr Ser Glu Ser Val Lys Leu Leu Gln
305                    310                    315                    320

Lys Ile Leu Glu Glu Asp Glu Arg Lys Ile Arg Ile Gly Val Arg
            325                    330                    335

Phe Ser Lys Phe Ile Glu Ala Ile Gly Leu Asp Lys Phe Phe Asp Thr
            340                    345                    350

<210> SEQ ID NO 23
<211> LENGTH: 83
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(83)
<223> OTHER INFORMATION: L-nucleotides

<400> SEQUENCE: 23
gtggaaccga caacttgtgc tgcgtccagc ataagaaagg agctccctca gaagaagctg    60
cgcagcgtgc cagtctgagc tcc    83

<210> SEQ ID NO 24
<211> LENGTH: 38
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(38)
<223> OTHER INFORMATION: L-nucleotides

<400> SEQUENCE: 24
tctaatacga ctcactatag gagctcagac tggcacgc    38

<210> SEQ ID NO 25
<211> LENGTH: 20
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(20)
<223> OTHER INFORMATION: L-nucleotides

<400> SEQUENCE: 25
gtggaaccga caacttgtgc                                              20

<210> SEQ ID NO 26
<211> LENGTH: 528
<212> TYPE: DNA
<213> ORGANISM: African swine fever virus
<220> FEATURE:
<221> NAME/KEY: misc_feature
<223> OTHER INFORMATION: Polymerase X, E.coli codon optimized

<400> SEQUENCE: 26
atgctgaccc tgattcaggg caaaaaaatc gtgaaccatc tgcgtagccg tctggccttt      60
gaatataacg gccagctgat taaaattctg agcaaaaaca ttgtggcggt gggcagcctg     120
cgtcgtgaag aaaaaatgct gaacgatgtg gatctgctga ttattgtgcc ggaaaaaaaa     180
ctgctgaaac atgtgctgcc gaacattcgt attaaaggcc tgagctttag cgtgaaagtg     240
tgcggcgaac gtaaatgcgt gctgtttatc gaatgggaaa aaaaaccta ccagctggac     300 ctgtttaccg cgctggccga agaaaaaccg tatgcgatct tcatttttac cggtccggtg     360
agctatctga ttcgtattcg tgcggcgctg aaaaaaaaaa actacaaact gaaccagtat     420
ggcctgttta aaaccagac cctggtgccg ctgaaaatta ccaccgaaaa agaactgatt     480
aaagaactgg gctttaccta tcgcattccg aaaaaacgcc tgtaataa              528

<210> SEQ ID NO 27
<211> LENGTH: 210
<212> TYPE: PRT
<213> ORGANISM: African swine fever virus
<220> FEATURE:
<221> NAME/KEY: MISC_FEATURE
<223> OTHER INFORMATION: Polymerase X, His-tagged

<400> SEQUENCE: 27

Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
            20                  25                  30

Arg Trp Gly Ser Met Leu Thr Leu Ile Gln Gly Lys Lys Ile Val Asn
        35                  40                  45

His Leu Arg Ser Arg Leu Ala Phe Glu Tyr Asn Gly Gln Leu Ile Lys
    50                  55                  60

Ile Leu Ser Lys Asn Ile Val Ala Val Gly Ser Leu Arg Arg Glu Glu
65                  70                  75                  80

Lys Met Leu Asn Asp Val Asp Leu Leu Ile Ile Val Pro Glu Lys Lys
                85                  90                  95

Leu Leu Lys His Val Leu Pro Asn Ile Arg Ile Lys Gly Leu Ser Phe
            100                 105                 110

Ser Val Lys Val Cys Gly Glu Arg Lys Cys Val Leu Phe Ile Glu Trp
        115                 120                 125

-continued

```
Glu Lys Lys Thr Tyr Gln Leu Asp Leu Phe Thr Ala Leu Ala Glu Glu
    130                 135                 140

Lys Pro Tyr Ala Ile Phe His Phe Thr Gly Pro Val Ser Tyr Leu Ile
145                 150                 155                 160

Arg Ile Arg Ala Ala Leu Lys Lys Lys Asn Tyr Lys Leu Asn Gln Tyr
                165                 170                 175

Gly Leu Phe Lys Asn Gln Thr Leu Val Pro Leu Lys Ile Thr Thr Glu
                180                 185                 190

Lys Glu Leu Ile Lys Glu Leu Gly Phe Thr Tyr Arg Ile Pro Lys Lys
            195                 200                 205

Arg Leu
    210

<210> SEQ ID NO 28
<211> LENGTH: 34
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: D-nucleotides

<400> SEQUENCE: 28
tccggtgagc tatctgggtc gtattcgtgc ggcg                                    34

<210> SEQ ID NO 29
<211> LENGTH: 34
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: D-nucleotides

<400> SEQUENCE: 29
cgccgcacga atacgaccca gatagctcac cgga                                    34

<210> SEQ ID NO 30
<211> LENGTH: 31
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: D-nucleotides

<400> SEQUENCE: 30
tgagctttag cgtgaaaggg tgcggcgaac g                                       31

<210> SEQ ID NO 31
<211> LENGTH: 31
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: D-nucleotides

<400> SEQUENCE: 31
cgttcgccgc acccttcac gctaaagctc a                                        31
```

```
<210> SEQ ID NO 32
<211> LENGTH: 31
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: D-nucleotides

<400> SEQUENCE: 32
tgagctttag cgtgaaagcg tgcggcgaac g                            31

<210> SEQ ID NO 33
<211> LENGTH: 31
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: D-nucleotides

<400> SEQUENCE: 33
cgttcgccgc acgctttcac gctaaagctc a                            31

<210> SEQ ID NO 34
<211> LENGTH: 36
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: D-nucleotides

<400> SEQUENCE: 34
tgaaagtgtg cggcgaacgt aaaagcgtgc tgttta                       36

<210> SEQ ID NO 35
<211> LENGTH: 36
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: D-nucleotides

<400> SEQUENCE: 35
taaacagcac gcttttacgt tcgccgcaca ctttca                       36

<210> SEQ ID NO 36
<211> LENGTH: 15
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: D-nucleotides

<400> SEQUENCE: 36
gatcacagtg agtac                                              15

<210> SEQ ID NO 37
<211> LENGTH: 17
<212> TYPE: DNA
<213> ORGANISM: Artificial
```

```
<220> FEATURE:
<223> OTHER INFORMATION: Synthetic
<220> FEATURE:
<221> NAME/KEY: misc_feature
<223> OTHER INFORMATION: D-nucleotides
<220> FEATURE:
<221> NAME/KEY: misc_feature
<222> LOCATION: (1)..(1)
<223> OTHER INFORMATION: Phosphate attached

<400> SEQUENCE: 37
gtaaaacgac ggccagt                                                    17

<210> SEQ ID NO 38
<211> LENGTH: 33
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: D-nucleotides

<400> SEQUENCE: 38
actggccgtc gttttacagt actcactgtg atc                                  33

<210> SEQ ID NO 39
<211> LENGTH: 33
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: D-nucleotides

<400> SEQUENCE: 39
actggccgtc gttttaccgt actcactgtg atc                                  33

<210> SEQ ID NO 40
<211> LENGTH: 33
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: D-nucleotides

<400> SEQUENCE: 40
actggccgtc gttttacggt actcactgtg atc                                  33

<210> SEQ ID NO 41
<211> LENGTH: 33
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: D-nucleotides

<400> SEQUENCE: 41
actggccgtc gttttactgt actcactgtg atc                                  33

<210> SEQ ID NO 42
<211> LENGTH: 12
<212> TYPE: DNA
<213> ORGANISM: Artificial
```

```
<220> FEATURE:
<223> OTHER INFORMATION: Synthetic
<220> FEATURE:
<221> NAME/KEY: misc_feature
<223> OTHER INFORMATION: D-nucleotides
<220> FEATURE:
<221> NAME/KEY: misc_feature
<222> LOCATION: (1)..(1)
<223> OTHER INFORMATION: Phosphate attached

<400> SEQUENCE: 42
acgacggcca gt                                                                     12

<210> SEQ ID NO 43
<211> LENGTH: 40
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<223> OTHER INFORMATION: All-D-peptide
<220> FEATURE:
<221> NAME/KEY: MISC_FEATURE
<222> LOCATION: (1)..(1)
<223> OTHER INFORMATION: A is AcM
<220> FEATURE:
<221> NAME/KEY: MISC_FEATURE
<222> LOCATION: (40)..(40)
<223> OTHER INFORMATION: L is L-OGp

<400> SEQUENCE: 43

Met Leu Thr Leu Ile Gln Gly Lys Lys Ile Val Asn His Leu Arg Ser
1               5                   10                  15

Arg Leu Ala Phe Glu Tyr Asn Gly Gln Leu Ile Lys Ile Leu Ser Lys
            20                  25                  30

Asn Ile Val Ala Val Gly Ser Leu
        35                  40

<210> SEQ ID NO 44
<211> LENGTH: 39
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<223> OTHER INFORMATION: All-D-peptide
<220> FEATURE:
<221> NAME/KEY: MISC_FEATURE
<222> LOCATION: (1)..(1)
<223> OTHER INFORMATION: R is H-R
<220> FEATURE:
<221> NAME/KEY: MISC_FEATURE
<222> LOCATION: (39)..(39)
<223> OTHER INFORMATION: A is A-SMe

<400> SEQUENCE: 44

Arg Arg Glu Glu Lys Leu Asn Asp Val Asp Leu Leu Ile Ile Val Pro
1               5                   10                  15

Glu Lys Lys Leu Leu Lys His Val Leu Pro Asn Ile Arg Ile Lys Gly
            20                  25                  30

Leu Ser Phe Ser Val Lys Ala
        35

<210> SEQ ID NO 45
<211> LENGTH: 94
<212> TYPE: PRT
<213> ORGANISM: Artificial
```

<220> FEATURE:
<223> OTHER INFORMATION: Synthetic
<220> FEATURE:
<221> NAME/KEY: MISC_FEATURE
<223> OTHER INFORMATION: All-D-peptide
<220> FEATURE:
<221> NAME/KEY: MISC_FEATURE
<222> LOCATION: (1)..(1)
<223> OTHER INFORMATION: C is H-C
<220> FEATURE:
<221> NAME/KEY: MISC_FEATURE
<222> LOCATION: (94)..(94)
<223> OTHER INFORMATION: L is L-OH

<400> SEQUENCE: 45

Cys Gly Glu Arg Lys Cys Val Leu Phe Ile Glu Trp Glu Lys Lys Thr
1               5                   10                  15

Tyr Gln Leu Asp Leu Phe Thr Ala Leu Ala Glu Glu Lys Pro Tyr Ala
            20                  25                  30

Ile Phe His Phe Thr Gly Pro Val Ser Tyr Leu Ile Arg Ile Arg Ala
        35                  40                  45

Ala Leu Lys Lys Lys Asn Tyr Lys Leu Asn Gln Tyr Gly Leu Phe Lys
    50                  55                  60

Asn Gln Thr Leu Val Pro Leu Lys Ile Thr Thr Glu Lys Glu Leu Ile
65                  70                  75                  80

Lys Glu Leu Gly Phe Thr Tyr Arg Ile Pro Lys Lys Arg Leu
                85                  90

<210> SEQ ID NO 46
<211> LENGTH: 80
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<223> OTHER INFORMATION: All-D-peptide
<220> FEATURE:
<221> NAME/KEY: MISC_FEATURE
<222> LOCATION: (1)..(1)
<223> OTHER INFORMATION: M is Ac-M
<220> FEATURE:
<221> NAME/KEY: MISC_FEATURE
<222> LOCATION: (80)..(80)
<223> OTHER INFORMATION: A is A-SMe

<400> SEQUENCE: 46

Met Leu Thr Leu Ile Gln Gly Lys Lys Ile Val Asn His Leu Arg Ser
1               5                   10                  15

Arg Leu Ala Phe Glu Tyr Asn Gly Gln Leu Ile Lys Ile Leu Ser Lys
            20                  25                  30

Asn Ile Val Ala Val Gly Ser Leu Arg Arg Glu Glu Lys Met Leu Asn
        35                  40                  45

Asp Val Asp Leu Leu Ile Ile Val Pro Glu Lys Lys Leu Leu Lys His
    50                  55                  60

Val Leu Pro Asn Ile Arg Ile Lys Gly Leu Ser Phe Ser Val Lys Ala
65                  70                  75                  80

<210> SEQ ID NO 47
<211> LENGTH: 19
<212> TYPE: DNA
<213> ORGANISM: Artificial
<220> FEATURE:
<223> OTHER INFORMATION: Synthetic
<220> FEATURE:
<221> NAME/KEY: misc_feature

```
<223> OTHER INFORMATION: D-nucleotides
<220> FEATURE:
<221> NAME/KEY: misc_feature
<222> LOCATION: (1)..(1)
<223> OTHER INFORMATION: Fluorescent dye Atto-532 attached

<400> SEQUENCE: 47
ggagctcaga ctggcacgc                                             19

<210> SEQ ID NO 48
<211> LENGTH: 83
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: D-nucleotides

<400> SEQUENCE: 48
gtggaaccga caacttgtgc tgcgtccagc ataagaaagg agctccctca gaagaagctg    60
cgcagcgtgc cagtctgagc tcc                                            83

<210> SEQ ID NO 49
<211> LENGTH: 21
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(2)
<223> OTHER INFORMATION: D-nucleotides
<220> FEATURE:
<221> NAME/KEY: misc_feature
<222> LOCATION: (3)..(21)
<223> OTHER INFORMATION: L-nucleotides

<400> SEQUENCE: 49
ggggagctca gactggcacg c                                          21

<210> SEQ ID NO 50
<211> LENGTH: 1056
<212> TYPE: DNA
<213> ORGANISM: Sulfolobus solfataricus
<220> FEATURE:
<221> NAME/KEY: misc_feature
<223> OTHER INFORMATION: D-nucleotides
<220> FEATURE:
<221> NAME/KEY: misc_feature
<223> OTHER INFORMATION: Polymerase Dpo4, E.coli codon optimized

<400> SEQUENCE: 50
atgattgtgc tgtttgtgga ttttgattat ttttatgccc aggtggaaga agttctgaat    60
ccgagcctga aggtaaaacc ggttgttgtt tgtgtttttta gcggtcgctt tgaagatagc   120
ggtgcagttg caaccgccaa ttatgaagcc cgtaaatttg gtgttaaagc cggtattccg   180
attgttgaag ccaaaaaaat tctgccgaat gcagtttatc tgccgatgcg caaagaagtt   240
tatcagcagg ttagcagccg tattatgaat ctgctgcgcg aatatagcga aaaaattgaa   300
attgccagca ttgatgaagc ctatctggat attagcgata agtgcgcga ttatcgcgaa    360 gcatataatc tgggcctgga aattaaaaat aaaatcctgg aaaaagaaaa aattaccgtg   420
accgtgggca ttagcaaaaa taaagtgttt gccaaaattg cagcagatat ggcaaaaccg   480
aatggcatta agtgattga tgatgaagaa gtgaaacgtc tgattcgcga actggatatt   540
```

-continued

```
gcagatgttc cgggtattgg caatattacc gcagaaaaac tgaaaaaact gggcattaat    600
aaactggttg ataccctgag cattgaattt gataaactga aaggcatgat tggtgaagcg    660
aaagccaaat atctgattag cctggcacgt gatgaatata tgaaccgat tcgtacccgt     720 gttcgtaaaa gcattggtcg tattgtgacc atgaaacgca atagccgtaa tctggaagaa    780
attaaaccgt acctgtttcg tgcaattgaa gaaagctatt ataaactgga taaacgcatt    840
ccgaaagcca ttcatgttgt tgcagttacc gaagatctgg atattgttag ccgtggtcgt    900
acctttccgc atggtattag caaagaaacc gcctatagcg aaagcgttaa actgctgcag    960
aaaatcctgg aagaagatga acgtaaaatt cgtcgtattg gtgtgcgctt tagcaaattt   1020
attgaagcca ttggcctgga taatttttt gatacc                              1056
```

<210> SEQ ID NO 51
<211> LENGTH: 368
<212> TYPE: PRT
<213> ORGANISM: Sulfolobus solfataricus
<220> FEATURE:
<221> NAME/KEY: MISC_FEATURE
<223> OTHER INFORMATION: Polymerase Dpo4, Strep-tagged

<400> SEQUENCE: 51

```
Met Ala Ser Ala Trp Ser His Pro Gln Phe Glu Lys Ser Gly Met Ile
1               5                   10                  15

Val Leu Phe Val Asp Phe Asp Tyr Phe Tyr Ala Gln Val Glu Glu Val
            20                  25                  30

Leu Asn Pro Ser Leu Lys Gly Lys Pro Val Val Val Cys Val Phe Ser
        35                  40                  45

Gly Arg Phe Glu Asp Ser Gly Ala Val Ala Thr Ala Asn Tyr Glu Ala
    50                  55                  60

Arg Lys Phe Gly Val Lys Ala Gly Ile Pro Ile Val Glu Ala Lys Lys
65                  70                  75                  80

Ile Leu Pro Asn Ala Val Tyr Leu Pro Met Arg Lys Glu Val Tyr Gln
                85                  90                  95

Gln Val Ser Ser Arg Ile Met Asn Leu Leu Arg Glu Tyr Ser Glu Lys
            100                 105                 110

Ile Glu Ile Ala Ser Ile Asp Glu Ala Tyr Leu Asp Ile Ser Asp Lys
        115                 120                 125

Val Arg Asp Tyr Arg Glu Ala Tyr Asn Leu Gly Leu Glu Ile Lys Asn
    130                 135                 140

Lys Ile Leu Glu Lys Glu Lys Ile Thr Val Thr Val Gly Ile Ser Lys
145                 150                 155                 160

Asn Lys Val Phe Ala Lys Ile Ala Ala Asp Met Ala Lys Pro Asn Gly
                165                 170                 175

Ile Lys Val Ile Asp Asp Glu Val Lys Arg Leu Ile Arg Glu Leu
            180                 185                 190

Asp Ile Ala Asp Val Pro Gly Ile Gly Asn Ile Thr Ala Glu Lys Leu
        195                 200                 205

Lys Lys Leu Gly Ile Asn Lys Leu Val Asp Thr Leu Ser Ile Glu Phe
    210                 215                 220

Asp Lys Leu Lys Gly Met Ile Gly Glu Ala Lys Ala Lys Tyr Leu Ile
225                 230                 235                 240

Ser Leu Ala Arg Asp Glu Tyr Asn Glu Pro Ile Arg Thr Arg Val Arg
                245                 250                 255

Lys Ser Ile Gly Arg Ile Val Thr Met Lys Arg Asn Ser Arg Asn Leu
            260                 265                 270
```

```
Glu Glu Ile Lys Pro Tyr Leu Phe Arg Ala Ile Glu Ser Tyr Tyr
        275                 280                 285

Lys Leu Asp Lys Arg Ile Pro Lys Ala Ile His Val Val Ala Val Thr
        290                 295                 300

Glu Asp Leu Asp Ile Val Ser Arg Gly Arg Thr Phe Pro His Gly Ile
305                 310                 315                 320

Ser Lys Glu Thr Ala Tyr Ser Glu Ser Val Lys Leu Leu Gln Lys Ile
                325                 330                 335

Leu Glu Glu Asp Glu Arg Lys Ile Arg Arg Ile Gly Val Arg Phe Ser
                340                 345                 350

Lys Phe Ile Glu Ala Ile Gly Leu Asp Lys Phe Phe Asp Thr Gly Ser
        355                 360                 365
```

<210> SEQ ID NO 52
<211> LENGTH: 59
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: D-nucleotides

<400> SEQUENCE: 52
caaaaataaa gtgtttgcca aaattgcatg cgatatggca aaaccgaatg gcattaaag    59

<210> SEQ ID NO 53
<211> LENGTH: 59
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: D-nucleotides

<400> SEQUENCE: 53
ctttaatgcc attcggtttt gccatatcgc atgcaatttt ggcaaacact ttattttg     59

<210> SEQ ID NO 54
<211> LENGTH: 51
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: D-nucleotides

<400> SEQUENCE: 54
tgaaaaaact gggcattaat aaactgtgtg ataccctgag cattgaattt g             51

<210> SEQ ID NO 55
<211> LENGTH: 51
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: D-nucleotides

<400> SEQUENCE: 55
caaattcaat gctcagggta tcacacagtt tattaatgcc cagttttttc a             51

```
<210> SEQ ID NO 56
<211> LENGTH: 39
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: D-nucleotides

<400> SEQUENCE: 56
tgaaaggtaa accggttgtt gtttctgttt ttagcggtc                          39

<210> SEQ ID NO 57
<211> LENGTH: 39
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: D-nucleotides

<400> SEQUENCE: 57
gaccgctaaa aacagaaaca acaaccggtt tacctttca                          39

<210> SEQ ID NO 58
<211> LENGTH: 46
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: D-nucleotides

<400> SEQUENCE: 58
atgcgcaaag aagtttatca gcaggtttgt agccgtatta tgaatc                  46

<210> SEQ ID NO 59
<211> LENGTH: 46
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: D-nucleotides

<400> SEQUENCE: 59
gattcataat acggctacaa acctgctgat aaacttcttt gcgcat                  46

<210> SEQ ID NO 60
<211> LENGTH: 43
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: D-nucleotides

<400> SEQUENCE: 60
aagtttatca gcaggttagc tgtcgtatta tgaatctgct gcg                     43

<210> SEQ ID NO 61
<211> LENGTH: 43
<212> TYPE: DNA
```

```
<213> ORGANISM: Artificial
<220> FEATURE:
<223> OTHER INFORMATION: Synthetic
<220> FEATURE:
<221> NAME/KEY: misc_feature
<223> OTHER INFORMATION: D-nucleotides

<400> SEQUENCE: 61
cgcagcagat tcataatacg acagctaacc tgctgataaa ctt          43

<210> SEQ ID NO 62
<211> LENGTH: 51
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: D-nucleotides

<400> SEQUENCE: 62
attatgaatc tgctgcgcga atattgtgaa aaaattgaaa ttgccagcat t    51

<210> SEQ ID NO 63
<211> LENGTH: 51
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: D-nucleotides

<400> SEQUENCE: 63
aatgctggca atttcaattt tttcacaata ttcgcgcagc agattcataa t    51

<210> SEQ ID NO 64
<211> LENGTH: 36
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: D-nucleotides
<220> FEATURE:
<221> NAME/KEY: misc_feature
<222> LOCATION: (1)..(1)
<223> OTHER INFORMATION: Phosphate attached

<400> SEQUENCE: 64
agcggctctt cgatgattgt gctgtttgtg gatttt                  36

<210> SEQ ID NO 65
<211> LENGTH: 36
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: D-nucleotides
<220> FEATURE:
<221> NAME/KEY: misc_feature
<222> LOCATION: (1)..(1)
<223> OTHER INFORMATION: Phosphate attached

<400> SEQUENCE: 65
agcggctctt cggcatgcaa ttttggcaaa cacttt                  36
```

```
<210> SEQ ID NO 66
<211> LENGTH: 27
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: D-nucleotides
<220> FEATURE:
<221> NAME/KEY: misc_feature
<222> LOCATION: (1)..(1)
<223> OTHER INFORMATION: Phosphate attached

<400> SEQUENCE: 66
agcggctctt cgtgcatcac gggagat                                            27

<210> SEQ ID NO 67
<211> LENGTH: 42
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: D-nucleotides
<220> FEATURE:
<221> NAME/KEY: misc_feature
<222> LOCATION: (1)..(1)
<223> OTHER INFORMATION: Phosphate attached

<400> SEQUENCE: 67
agcggctctt cgcccttgaa gctgccacaa ggcaggaacg tt                           42

<210> SEQ ID NO 68
<211> LENGTH: 154
<212> TYPE: PRT
<213> ORGANISM: Sulfolobus solfataricus
<220> FEATURE:
<221> NAME/KEY: MISC_FEATURE
<223> OTHER INFORMATION: Polymerase Dpo4, fragment 1-154

<400> SEQUENCE: 68

Met Ile Val Leu Phe Val Asp Phe Asp Tyr Phe Tyr Ala Gln Val Glu
1               5                   10                  15

Glu Val Leu Asn Pro Ser Leu Lys Gly Lys Pro Val Val Val Cys Val
            20                  25                  30

Phe Ser Gly Arg Phe Glu Asp Ser Gly Ala Val Ala Thr Ala Asn Tyr
        35                  40                  45

Glu Ala Arg Lys Phe Gly Val Lys Ala Gly Ile Pro Ile Val Glu Ala
    50                  55                  60

Lys Lys Ile Leu Pro Asn Ala Val Tyr Leu Pro Met Arg Lys Glu Val
65                  70                  75                  80

Tyr Gln Gln Val Ser Ser Arg Ile Met Asn Leu Leu Arg Glu Tyr Ser
                85                  90                  95

Glu Lys Ile Glu Ile Ala Ser Ile Asp Glu Ala Tyr Leu Asp Ile Ser
            100                 105                 110

Asp Lys Val Arg Asp Tyr Arg Glu Ala Tyr Asn Leu Gly Leu Glu Ile
        115                 120                 125

Lys Asn Lys Ile Leu Glu Lys Glu Lys Ile Thr Val Thr Val Gly Ile
    130                 135                 140

Ser Lys Asn Lys Val Phe Ala Lys Ile Ala
145                 150
```

<210> SEQ ID NO 69
<211> LENGTH: 36
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: D-nucleotides
<220> FEATURE:
<221> NAME/KEY: misc_feature
<222> LOCATION: (1)..(1)
<223> OTHER INFORMATION: Phosphate attached

<400> SEQUENCE: 69
agcggctctt cgatgggagg gaaatcaaac ggggaa                                  36

<210> SEQ ID NO 70
<211> LENGTH: 36
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: D-nucleotides
<220> FEATURE:
<221> NAME/KEY: misc_feature
<222> LOCATION: (1)..(1)
<223> OTHER INFORMATION: Phosphate attached

<400> SEQUENCE: 70
agcggctctt cggcacaaag ctttgaagag cttgtc                                  36

<210> SEQ ID NO 71
<211> LENGTH: 42
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: D-nucleotides
<220> FEATURE:
<221> NAME/KEY: misc_feature
<222> LOCATION: (1)..(1)
<223> OTHER INFORMATION: Phosphate attached

<400> SEQUENCE: 71
agcggctctt cgtgcgatat ggcaaaaccg aatggcatta aa                           42

<210> SEQ ID NO 72
<211> LENGTH: 40
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: D-nucleotides
<220> FEATURE:
<221> NAME/KEY: misc_feature
<222> LOCATION: (1)..(1)
<223> OTHER INFORMATION: Phosphate attached

<400> SEQUENCE: 72
agcggctctt cgcccttagg tatcaaaaaa tttatccagg                              40

<210> SEQ ID NO 73
<211> LENGTH: 198

<212> TYPE: PRT
<213> ORGANISM: Sulfolobus solfataricus
<220> FEATURE:
<221> NAME/KEY: MISC_FEATURE
<223> OTHER INFORMATION: Polymerase Dpo4, fragment 155-352

<400> SEQUENCE: 73

Cys Asp Met Ala Lys Pro Asn Gly Ile Lys Val Ile Asp Asp Glu Glu
1               5                   10                  15

Val Lys Arg Leu Ile Arg Glu Leu Asp Ile Ala Asp Val Pro Gly Ile
            20                  25                  30

Gly Asn Ile Thr Ala Glu Lys Leu Lys Lys Leu Gly Ile Asn Lys Leu
        35                  40                  45

Val Asp Thr Leu Ser Ile Glu Phe Asp Lys Leu Lys Gly Met Ile Gly
    50                  55                  60

Glu Ala Lys Ala Lys Tyr Leu Ile Ser Leu Ala Arg Asp Glu Tyr Asn
65                  70                  75                  80

Glu Pro Ile Arg Thr Arg Val Arg Lys Ser Ile Gly Arg Ile Val Thr
                85                  90                  95

Met Lys Arg Asn Ser Arg Asn Leu Glu Glu Ile Lys Pro Tyr Leu Phe
            100                 105                 110

Arg Ala Ile Glu Glu Ser Tyr Tyr Lys Leu Asp Lys Arg Ile Pro Lys
        115                 120                 125

Ala Ile His Val Val Ala Val Thr Glu Asp Leu Asp Ile Val Ser Arg
    130                 135                 140

Gly Arg Thr Phe Pro His Gly Ile Ser Lys Glu Thr Ala Tyr Ser Glu
145                 150                 155                 160

Ser Val Lys Leu Leu Gln Lys Ile Leu Glu Glu Asp Glu Arg Lys Ile
                165                 170                 175

Arg Arg Ile Gly Val Arg Phe Ser Lys Phe Ile Glu Ala Ile Gly Leu
            180                 185                 190

Asp Lys Phe Phe Asp Thr
        195

<210> SEQ ID NO 74
<211> LENGTH: 36
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: D-nucleotides
<220> FEATURE:
<221> NAME/KEY: misc_feature
<222> LOCATION: (1)..(1)
<223> OTHER INFORMATION: Phosphate attached

<400> SEQUENCE: 74
agcggctctt cgtgtgatac cctgagcatt gaattt                         36

<210> SEQ ID NO 75
<211> LENGTH: 150
<212> TYPE: PRT
<213> ORGANISM: Sulfolobus solfataricus
<220> FEATURE:
<221> NAME/KEY: MISC_FEATURE
<223> OTHER INFORMATION: Polymerase Dpo4, fragment 155-352

<400> SEQUENCE: 75

Cys Asp Thr Leu Ser Ile Glu Phe Asp Lys Leu Lys Gly Met Ile Gly
1               5                   10                  15

Glu Ala Lys Ala Lys Tyr Leu Ile Ser Leu Ala Arg Asp Glu Tyr Asn
            20                  25                  30

Glu Pro Ile Arg Thr Arg Val Arg Lys Ser Ile Gly Arg Ile Val Thr
        35                  40                  45

Met Lys Arg Asn Ser Arg Asn Leu Glu Glu Ile Lys Pro Tyr Leu Phe
 50                  55                  60

Arg Ala Ile Glu Glu Ser Tyr Tyr Lys Leu Asp Lys Arg Ile Pro Lys
 65                  70                  75                  80

Ala Ile His Val Val Ala Val Thr Glu Asp Leu Asp Ile Val Ser Arg
                85                  90                  95

Gly Arg Thr Phe Pro His Gly Ile Ser Lys Glu Thr Ala Tyr Ser Glu
            100                 105                 110

Ser Val Lys Leu Leu Gln Lys Ile Leu Glu Glu Asp Glu Arg Lys Ile
        115                 120                 125

Arg Arg Ile Gly Val Arg Phe Ser Lys Phe Ile Glu Ala Ile Gly Leu
    130                 135                 140

Asp Lys Phe Phe Asp Thr
145                 150

<210> SEQ ID NO 76
<211> LENGTH: 36
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: D-nucleotides
<220> FEATURE:
<221> NAME/KEY: misc_feature
<222> LOCATION: (1)..(1)
<223> OTHER INFORMATION: Phosphate attached

<400> SEQUENCE: 76
agcggctctt cgatggcaga tatggcaaaa ccgaat         36

<210> SEQ ID NO 77
<211> LENGTH: 36
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: D-nucleotides
<220> FEATURE:
<221> NAME/KEY: misc_feature
<222> LOCATION: (1)..(1)
<223> OTHER INFORMATION: Phosphate attached

<400> SEQUENCE: 77
agcggctctt cggcacagtt tattaatgcc cagttt         36

<210> SEQ ID NO 78
<211> LENGTH: 48
<212> TYPE: PRT
<213> ORGANISM: Sulfolobus solfataricus
<220> FEATURE:
<221> NAME/KEY: MISC_FEATURE
<223> OTHER INFORMATION: Polymerase Dpo4, fragment 155-202
<220> FEATURE:
<221> NAME/KEY: MISC_FEATURE
<222> LOCATION: (1)..(48)
<223> OTHER INFORMATION: L is L-thioester -continued

<400> SEQUENCE: 78

Ala Asp Met Ala Lys Pro Asn Gly Ile Lys Val Ile Asp Asp Glu Glu
1               5                   10                  15

Val Lys Arg Leu Ile Arg Glu Leu Asp Ile Ala Asp Val Pro Gly Ile
            20                  25                  30

Gly Asn Ile Thr Ala Glu Lys Leu Lys Lys Leu Gly Ile Asn Lys Leu
        35                  40                  45

<210> SEQ ID NO 79
<211> LENGTH: 38
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: D-nucleotides

<400> SEQUENCE: 79
tctaatacga ctcactatag gagctcagac tggcacgc                              38

<210> SEQ ID NO 80
<211> LENGTH: 20
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: D-nucleotides

<400> SEQUENCE: 80
gtggaaccga caacttgtgc                                                  20

<210> SEQ ID NO 81
<211> LENGTH: 53
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<223> OTHER INFORMATION: All-D-peptide
<220> FEATURE:
<221> NAME/KEY: MISC_FEATURE
<222> LOCATION: (1)..(1)
<223> OTHER INFORMATION: R is H-R
<220> FEATURE:
<221> NAME/KEY: MISC_FEATURE
<222> LOCATION: (53)..(53)
<223> OTHER INFORMATION: T is T-NH2

<400> SEQUENCE: 81

Arg Thr Phe Pro His Gly Ile Ser Lys Glu Thr Ala Tyr Ser Glu Ser
1               5                   10                  15

Val Lys Leu Leu Gln Lys Ile Leu Glu Glu Asp Glu Arg Lys Ile Arg
            20                  25                  30

Arg Ile Gly Val Arg Phe Ser Lys Phe Ile Glu Ala Ile Gly Leu Asp
        35                  40                  45

Lys Phe Phe Asp Thr
    50

<210> SEQ ID NO 82
<211> LENGTH: 97
<212> TYPE: PRT
<213> ORGANISM: Artificial

```
<220> FEATURE:
<223> OTHER INFORMATION: Synthetic
<220> FEATURE:
<221> NAME/KEY: MISC_FEATURE
<223> OTHER INFORMATION: All-D-peptide
<220> FEATURE:
<221> NAME/KEY: MISC_FEATURE
<222> LOCATION: (1)..(1)
<223> OTHER INFORMATION: V is Boc-V
<220> FEATURE:
<221> NAME/KEY: MISC_FEATURE
<222> LOCATION: (97)..(97)
<223> OTHER INFORMATION: G is G-OH

<400> SEQUENCE: 82

Val Asp Thr Leu Ser Ile Glu Phe Asp Lys Leu Lys Gly Met Ile Gly
1               5                   10                  15

Glu Ala Lys Ala Lys Tyr Leu Ile Ser Leu Ala Arg Asp Glu Tyr Asn
            20                  25                  30

Glu Pro Ile Arg Thr Arg Val Arg Lys Ser Ile Gly Arg Ile Val Thr
        35                  40                  45

Met Lys Arg Asn Ser Arg Asn Leu Glu Glu Ile Lys Pro Tyr Leu Phe
    50                  55                  60

Arg Ala Ile Glu Glu Ser Tyr Tyr Lys Leu Asp Lys Arg Ile Pro Lys
65                  70                  75                  80

Ala Ile His Val Val Ala Val Thr Glu Asp Leu Asp Ile Val Ser Arg
                85                  90                  95

Gly

<210> SEQ ID NO 83
<211> LENGTH: 150
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<223> OTHER INFORMATION: All-D-peptide
<220> FEATURE:
<221> NAME/KEY: MISC_FEATURE
<222> LOCATION: (1)..(1)
<223> OTHER INFORMATION: V is H-V
<220> FEATURE:
<221> NAME/KEY: MISC_FEATURE
<222> LOCATION: (150)..(150)
<223> OTHER INFORMATION: T is T-NH2

<400> SEQUENCE: 83

Val Asp Thr Leu Ser Ile Glu Phe Asp Lys Leu Lys Gly Met Ile Gly
1               5                   10                  15

Glu Ala Lys Ala Lys Tyr Leu Ile Ser Leu Ala Arg Asp Glu Tyr Asn
            20                  25                  30

Glu Pro Ile Arg Thr Arg Val Arg Lys Ser Ile Gly Arg Ile Val Thr
        35                  40                  45

Met Lys Arg Asn Ser Arg Asn Leu Glu Glu Ile Lys Pro Tyr Leu Phe
    50                  55                  60

Arg Ala Ile Glu Glu Ser Tyr Tyr Lys Leu Asp Lys Arg Ile Pro Lys
65                  70                  75                  80

Ala Ile His Val Val Ala Val Thr Glu Asp Leu Asp Ile Val Ser Arg
                85                  90                  95

Gly Arg Thr Phe Pro His Gly Ile Ser Lys Glu Thr Ala Tyr Ser Glu
                100                 105                 110

Ser Val Lys Leu Leu Gln Lys Ile Leu Glu Glu Asp Glu Arg Lys Ile
```

```
                  115                 120                 125
Arg Arg Ile Gly Val Arg Phe Ser Lys Phe Ile Glu Ala Ile Gly Leu
    130                 135                 140

Asp Lys Phe Phe Asp Thr
145                 150

<210> SEQ ID NO 84
<211> LENGTH: 48
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<223> OTHER INFORMATION: All-D-peptide
<220> FEATURE:
<221> NAME/KEY: MISC_FEATURE
<222> LOCATION: (1)..(1)
<223> OTHER INFORMATION: C is Z-C
<220> FEATURE:
<221> NAME/KEY: MISC_FEATURE
<222> LOCATION: (48)..(48)
<223> OTHER INFORMATION: L is L-benzyl-thioester

<400> SEQUENCE: 84

Cys Asp Met Ala Lys Pro Asn Gly Ile Lys Val Ile Asp Asp Glu Glu
1               5                   10                  15

Val Lys Arg Leu Ile Arg Glu Leu Asp Ile Ala Asp Val Pro Gly Ile
            20                  25                  30

Gly Asn Ile Thr Ala Glu Lys Leu Lys Lys Leu Gly Ile Asn Lys Leu
        35                  40                  45

<210> SEQ ID NO 85
<211> LENGTH: 78
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<223> OTHER INFORMATION: All-D-peptide
<220> FEATURE:
<221> NAME/KEY: MISC_FEATURE
<222> LOCATION: (1)..(1)
<223> OTHER INFORMATION: R is H-R
<220> FEATURE:
<221> NAME/KEY: MISC_FEATURE
<222> LOCATION: (78)..(78)
<223> OTHER INFORMATION: A is A-SMe

<400> SEQUENCE: 85

Arg Lys Glu Val Tyr Gln Gln Val Ser Ser Arg Ile Met Asn Leu Leu
1               5                   10                  15

Arg Glu Tyr Ser Glu Lys Ile Glu Ile Ala Ser Ile Asp Glu Ala Tyr
            20                  25                  30

Leu Asp Ile Ser Asp Lys Val Arg Asp Tyr Arg Glu Ala Tyr Asn Leu
        35                  40                  45

Gly Leu Glu Ile Lys Asn Lys Ile Leu Glu Lys Glu Lys Ile Thr Val
    50                  55                  60

Thr Val Gly Ile Ser Lys Asn Lys Val Phe Ala Lys Ile Ala
65                  70                  75

<210> SEQ ID NO 86
<211> LENGTH: 76
<212> TYPE: PRT
<213> ORGANISM: Artificial
```

```
<220> FEATURE:
<223> OTHER INFORMATION: Synthetic
<220> FEATURE:
<221> NAME/KEY: MISC_FEATURE
<223> OTHER INFORMATION: All-D-peptide
<220> FEATURE:
<221> NAME/KEY: MISC_FEATURE
<222> LOCATION: (1)..(1)
<223> OTHER INFORMATION: M is Ac-M
<220> FEATURE:
<221> NAME/KEY: MISC_FEATURE
<222> LOCATION: (76)..(76)
<223> OTHER INFORMATION: M is M-OGp

<400> SEQUENCE: 86
```

Met Ile Val Leu Phe Val Asp Phe Asp Tyr Phe Tyr Ala Gln Val Glu
1               5                   10                  15

Glu Val Leu Asn Pro Ser Leu Lys Gly Lys Pro Val Val Cys Val
            20                  25                  30

Phe Ser Gly Arg Phe Glu Asp Ser Gly Ala Val Ala Thr Ala Asn Tyr
            35                  40                  45

Glu Ala Arg Lys Phe Gly Val Lys Ala Gly Ile Pro Ile Val Glu Ala
    50                  55                  60

Lys Lys Ile Leu Pro Asn Ala Val Tyr Leu Pro Met
65                  70                  75

```
<210> SEQ ID NO 87
<211> LENGTH: 198
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<223> OTHER INFORMATION: All-D-peptide
<220> FEATURE:
<221> NAME/KEY: MISC_FEATURE
<222> LOCATION: (1)..(1)
<223> OTHER INFORMATION: C is H-C
<220> FEATURE:
<221> NAME/KEY: MISC_FEATURE
<222> LOCATION: (198)..(198)
<223> OTHER INFORMATION: T is T-OH

<400> SEQUENCE: 87
```

Cys Asp Met Ala Lys Pro Asn Gly Ile Lys Val Ile Asp Asp Glu Glu
1               5                   10                  15

Val Lys Arg Leu Ile Arg Glu Leu Asp Ile Ala Asp Val Pro Gly Ile
            20                  25                  30

Gly Asn Ile Thr Ala Glu Lys Leu Lys Lys Leu Gly Ile Asn Lys Leu
            35                  40                  45

Cys Asp Thr Leu Ser Ile Glu Phe Asp Lys Leu Lys Gly Met Ile Gly
    50                  55                  60

Glu Ala Lys Ala Lys Tyr Leu Ile Ser Leu Ala Arg Asp Glu Tyr Asn
65                  70                  75                  80

Glu Pro Ile Arg Thr Arg Val Arg Lys Ser Ile Gly Arg Ile Val Thr
                85                  90                  95

Met Lys Arg Asn Ser Arg Asn Leu Glu Glu Ile Lys Pro Tyr Leu Phe
            100                 105                 110

Arg Ala Ile Glu Glu Ser Tyr Tyr Lys Leu Asp Lys Arg Ile Pro Lys
            115                 120                 125

Ala Ile His Val Val Ala Val Thr Glu Asp Leu Asp Ile Val Ser Arg
    130                 135                 140

```
Gly Arg Thr Phe Pro His Gly Ile Ser Lys Glu Thr Ala Tyr Ser Glu
145                 150                 155                 160

Ser Val Lys Leu Leu Gln Lys Ile Leu Glu Glu Asp Glu Arg Lys Ile
                165                 170                 175

Arg Arg Ile Gly Val Arg Phe Ser Lys Phe Ile Glu Ala Ile Gly Leu
            180                 185                 190

Asp Lys Phe Phe Asp Thr
            195
```

```
<210> SEQ ID NO 88
<211> LENGTH: 154
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<223> OTHER INFORMATION: All-D-peptide
<220> FEATURE:
<221> NAME/KEY: MISC_FEATURE
<222> LOCATION: (1)..(1)
<223> OTHER INFORMATION: M is Ac-M
<220> FEATURE:
<221> NAME/KEY: MISC_FEATURE
<222> LOCATION: (154)..(154)
<223> OTHER INFORMATION: A is A-SMe

<400> SEQUENCE: 88

Met Ile Val Leu Phe Val Asp Phe Asp Tyr Phe Tyr Ala Gln Val Glu
1               5                   10                  15

Glu Val Leu Asn Pro Ser Leu Lys Gly Lys Pro Val Val Val Cys Val
                20                  25                  30

Phe Ser Gly Arg Phe Glu Asp Ser Gly Ala Val Ala Thr Ala Asn Tyr
            35                  40                  45

Glu Ala Arg Lys Phe Gly Val Lys Ala Gly Ile Pro Ile Val Glu Ala
        50                  55                  60

Lys Lys Ile Leu Pro Asn Ala Val Tyr Leu Pro Met Arg Lys Glu Val
65                  70                  75                  80

Tyr Gln Gln Val Ser Ser Arg Ile Met Asn Leu Leu Arg Glu Tyr Ser
                85                  90                  95

Glu Lys Ile Glu Ile Ala Ser Ile Asp Glu Ala Tyr Leu Asp Ile Ser
                100                 105                 110

Asp Lys Val Arg Asp Tyr Arg Glu Ala Tyr Asn Leu Gly Leu Glu Ile
            115                 120                 125

Lys Asn Lys Ile Leu Glu Lys Glu Lys Ile Thr Val Thr Val Gly Ile
        130                 135                 140

Ser Lys Asn Lys Val Phe Ala Lys Ile Ala
145                 150
```

ENZYMATIC SYNTHESIS OF L-NUCLEIC ACIDS

The present invention is related to a method for adding one or more L-nucleotides to the 3' end of a first L-nucleic acid, a method for amplifying a target L-nucleic acid, a protein comprising an enzymatic activity exhibiting moiety, polymerases comprising an amino acid sequence wherein the amino acid of the amino acid sequence are D-amino acids, a polymerase variant of a wild type polymerase, wherein the wild type polymerase consists of an amino acid sequence according to SEQ ID NO: 15, a polymerase variant of a wild type polymerase, wherein the wild type polymerase consists of an amino acid sequence according to SEQ ID NO: 1, use of a protein comprising an enzymatic activity exhibiting moiety in a method for adding one or more L-nucleotides, use of a protein comprising an enzymatic activity exhibiting moiety in a method for amplifying a target L-nucleic acid, a method for the identification of a target molecule binding L-nucleic acid molecule, a method for producing the protein and polymerase, respectively, and a method for ligating a first D-peptide or a first D-Protein and a second D-peptide or a second D-protein to each other.

The availability of gene technology in the broader sense contributed much to the progress made over the last decades in the fields of medicine and diagnosis as well as in basic research. Synthesis power provided by gene technology is going beyond the one of chemical synthesis. Gene technology and genetic engineering in particular allow the production of factually unlimited amounts of L-peptides and L-proteins making use of the enzymatic machinery of prokaryotic and eukaryotic cells. Enzymes and polymerases in particular, either wild type forms or variants of such wild type forms, allow the synthesis of D-nucleic acids linking the building blocks of such D-nucleic acids, i.e. D-nucleotides to a length which is, at least not with a reasonable yield, achievable by chemical synthesis.

Due to chiral specificity, the enzymes used in gene technology can only make use of building blocks and substrates, respectively, the chirality of which fits to their own chirality. Buildings blocks and substrates, respectively, of opposite chirality cannot be subject to the enzymes' activity. Due to the principle of chiral reciprocity, the processing of building blocks and substrates, respectively, of opposite chirality require the enzymes to have opposite chirality, too.

This principle of chiral reciprocity is, for example, intensively used in the generation of target binding L-nucleic acids which are also known and referred to as spiegelmers. To date spiegelmers are identified by a process that uses, in a first step, a D-nucleic acid library for in vitro selection against the enantiomeric form of the target molecule or target structure such as D-peptides or D-proteins. In a second step, the thus identified D-nucleic acids binding to the enantiomeric form of the target molecule or target structure are prepared as corresponding L-nucleic acids. As a result of the principle of chiral reciprocity these L-nucleic acids, i.e. spiegelmers, are able to bind to the true or actual target molecule such as L-peptides or L-proteins and not to the enantiomeric form thereof such as D-peptides or D-proteins used for the selection process. Preferably, such true or actual target molecule or target structure is the target molecule or target structure as present in a biological system such as a human or animal body. Methods for the preparation of such spiegelmers are described, for example, in described in 'The Aptamer Handbook' (eds. Klussmann, 2006).

One way of making the process of identifying spiegelmers easier, could be to redesign the process such that L-nucleic acids are directly selected from a L-nucleic acid library using the target molecule or target structure in that enantiomeric form exhibited by the true or actual target molecule or target structure. As part of the process is the amplification of those L-nucleic acids initially binding to the target molecule and target structure, respectively, a polymerase adding at least one nucleotide to an L-primer would be required. To date, no polymerase consisting of L-amino acids is known which is capable of doing so. Because of this, there is a need for a polymerase and similar enzymes consisting of D-amino acids. As gene technology cannot provide such functionally active polymerase consisting of D-amino acids, chemical synthesis is required. However, the synthesis of D-proteins or D-polypeptides is limited to comparatively small molecules. The largest D-protein synthesized so far is the D-protein form of the angiogenic protein vascular endothelial growth factor (abbr. VEGF-A) consisting of 102 D-amino acids (Mandal et al., 2012), Polymerases, however, typically consist of more than 300 amino acids.

Therefore, the problem underlying the present invention is the provision of a method which allow the adding of at least one nucleotide to an L-nucleic acid such as a primer. A further problem underlying the present invention is the provision of a method for amplifying a target L-nucleic acid making use of L-nucleotides. A still further problem underlying the present invention is the provision of means which allow the practicing of such methods.

These and other problems underlying the present invention are solved by the subject matter of the attached independent claims. Preferred embodiments may be taken from the attached dependent claims.

The problem underlying the instant application is also solved in a first aspect which is also the first embodiment of the first aspect, by a method for adding one or more L-nucleotides to the 3'end of a first L-nucleic acid, wherein the method comprises the step of reacting the one or more L-nucleotides with the first L-nucleic acid in the presence of a protein comprising an enzymatic activity exhibiting moiety, wherein the enzymatic activity is capable of adding one or more L-nucleotides to the 3' end of the first L-nucleic acid.

In a second embodiment of the first aspect which is also an embodiment of the first embodiment of the first aspect, the enzymatic activity exhibiting moiety consists of an amino acid sequence, wherein the amino acids of the amino acid sequence are D-amino acids.

In a third embodiment of the first aspect which is also an embodiment of the first and the second embodiment of the first aspect, the enzymatic activity exhibiting moiety is a polymerase activity exhibiting moiety.

In a fourth embodiment of the first aspect which is also an embodiment of the first, second and third embodiment of the first aspect, the enzymatic activity is a polymerase activity.

In a fifth embodiment of the first aspect which is also an embodiment of the fourth embodiment of the first aspect, the polymerase activity is a thermostable polymerase activity.

In a sixth embodiment of the first aspect which is also an embodiment of the third, fourth and fifth embodiment of the first aspect, the amino acid sequence of the polymerase activity exhibiting moiety comprises at least 300 amino acids.

In a seventh embodiment of the first aspect which is also an embodiment of the sixth embodiment of the first aspect, the amino acid sequence of the polymerase activity exhibiting moiety comprises between 300 and 900 amino acids, preferably 300 and 600 amino acids, more preferably between 300 and 360 amino acids, most preferably 340 to 360 amino acids.

In an eighth embodiment of the first aspect which is also an embodiment of the fourth, fifth sixth and seventh embodiment of the first aspect, the polymerase activity is a DNA-polymerase activity.

In a ninth embodiment of the first aspect which is also an embodiment of the eighth embodiment of the first aspect, the DNA-polymerase activity is a DNA-dependent DNA-polymerase activity.

In a tenth embodiment of the first aspect which is also an embodiment of the first, second, third, fourth, fifth, sixth, seventh, eighth and ninth embodiment of the first aspect, the enzymatic activity exhibiting moiety is an enzyme.

In an eleventh embodiment of the first aspect which is also an embodiment of the third, fourth, fifth, sixth, seventh, eighth and ninth embodiment of the first aspect, the polymerase activity exhibiting moiety is a polymerase.

In a twelfth embodiment of the first aspect which is also an embodiment of the first, second, third, fourth, eighth, ninth, tenth and eleventh embodiment of the first aspect, the polymerase activity exhibiting moiety is selected from the group of African Swine Fever Virus Polymerase X, *Thermus thermophilus* polymerase X core domain, rat Polymerase beta, eukaryotic Polymerase beta, Klenow Fragment, Klenow exo-polymerase, T4 DNA polymerase, Phi29 DNA polymerase, Sequenase, T7 DNA polymerase, SP6 polymerase, DNA polymerase I, polymerase lambda, and variants of each and any thereof, wherein preferably the polymerase activity exhibiting moiety is the African Swine Fever Virus Polymerase X or a variant thereof, consisting of an amino acid sequence selected of an amino acid sequence selected from the group consisting of amino acid sequence according to SEQ ID NO: 1, amino acid sequence according to SEQ ID NO: 2, amino acid sequence according to SEQ ID NO: 3 and amino acid sequence according to SEQ ID NO: 4.

In a 13$^{th}$ embodiment of the first aspect which is also an embodiment of the first, second, third, fourth, fifth, sixth, seventh, eighth, ninth, tenth and eleventh embodiment of the first aspect, the polymerase activity exhibiting moiety is selected from the group of polymerase DPO4, *Thermococcus litoralis* DNA polymerase, *Pyrococcus* sp. DNA polymerase, *Pyrococcus furiosus* DNA polymerase, Pfuturbo polymerase, *Sulfolobus solfataricus* DNA polymerase, *Thermococcus* gorgonarius DNA polymerase, KOD polymerase, Taq polymerase, Tth polymerase, Pyrobest polymerase, Pwo polymerase, Sac polymerase, Bst polymerase, Poc polymerase, Pab polymerase, Mth polymerase, Pho polymerase, ES4 polymerase, EX-Taq polymerase, LA-Taq polymerase, Expand polymerases, Platinum Taqpolymerases, Hi-Fi polymerase, Tbr polymerase, Tfl polymerase, Tru polymerase, Tac polymerase, Tne polymerase, Tma polymerase, Tih polymerase, Tfi polymerase, AmpliTaq, Stoffel Fragment, 9° Nm DNA Polymerase, Therminator, Therminator II, Phusion High Fidelity Polymerase, Paq5000, Pfx-50, Proofstart, FideliTaq, Elongase, and variants thereof, wherein preferably the polymerase activity exhibiting moiety is the Dpo4 polymerase or a variant thereof, consisting of an amino acid sequence selected of an amino acid sequence selected from the group consisting of amino acid sequence according to SEQ ID NO: 15, amino acid sequence according to SEQ ID NO: 16, amino acid sequence according to SEQ ID NO: 17, amino acid sequence according to SEQ ID NO: 18, amino acid sequence according to SEQ ID NO: 19, amino acid sequence according to SEQ ID NO: 20, amino acid sequence according to SEQ ID NO: 21 and amino acid sequence according to SEQ ID NO: 22.

In a 14$^{th}$ embodiment of the first, second, third, fourth, fifth, sixth, seventh, eighth, ninth, tenth, eleventh, twelfth and 13$^{th}$ embodiment of the first aspect, the step of reacting is carried out under conditions which allow the adding of the at least one or more L-nucleotides to the first L-nucleic acid, preferably allow the adding of 5 to 20,000 L-nucleotides, preferably 10 to 2,000 L-nucleotides, more preferably 50 to 500 L-nucleotides, most preferably 50 to 100 L-nucleotides.

In a 15$^{th}$ embodiment of the first aspect which is also an embodiment of the first, second, third, fourth, fifth, sixth, seventh, eighth, ninth, tenth, eleventh, twelfth, 13$^{th}$ and 14$^{th}$ embodiment of the first aspect, the adding of the at least one or more L-nucleotides to the first L-nucleic acid is covalent binding of the at least one or more L-nucleotides to the first L-nucleic acid, preferably by forming a 3'-5' phosphodiester linkage between the 3'OH of the first L-nucleic acid and the 5' phosphate of one of the at least one or more L-nucleotides.

In a 16$^{th}$ embodiment of the first aspect which is also an embodiment of the first, second, third, fourth, fifth, sixth, seventh, eighth, ninth, tenth, eleventh, twelfth, 13$^{th}$, 14$^{th}$ and 15$^{th}$ embodiment of the first aspect, the first L-nucleic acid is a primer consisting of DNA, RNA, modified DNA, modified RNA or combinations thereof.

In a 17$^{th}$ embodiment of the first aspect which is also an embodiment of the first, second, third, fourth, fifth, sixth, seventh, eighth, ninth, tenth, eleventh, twelfth, 13$^{th}$, 14$^{th}$, 15$^{th}$ and 16$^{th}$ embodiment of the first aspect, the first L-nucleic acid consists of L-nucleotides and optionally a modification.

In an 18$^{th}$ embodiment of the first aspect which is also an embodiment of the first, second, third, fourth, fifth, sixth, seventh, eighth, ninth, tenth, eleventh, twelfth, 13$^{th}$, 14$^{th}$, 15$^{th}$ and 16$^{th}$ and 17$^{th}$ embodiment of the first aspect, the first L-nucleic acid consists of L-nucleotides.

In a 19$^{th}$ embodiment of the first aspect which is also an embodiment of the first, second, third, fourth, fifth, sixth, seventh, eighth, ninth, tenth, eleventh, twelfth, 13$^{th}$, 14th, 15$^{th}$ and 16$^{th}$, 17$^{th}$ and 18$^{th}$ embodiment of the first aspect, the reaction further comprises a second L-nucleic acid, wherein one molecule of the first L-nucleic acid is hybridized to one molecule of the second L-nucleic acid, preferably through Watson-Crick base pairing.

In a 20$^{th}$ embodiment of the first aspect which is also an embodiment of the 19$^{th}$ embodiment of the first aspect, the polymerase activity exhibiting moiety synthesizes a third L-nucleic acid that is complementary to the second L-nucleic acid, wherein the third L-nucleic acid comprise the first L-nucleic acid and the L-nucleotides added to the 3'end of the first L-nucleic acid.

The problem underlying the instant application is also solved in a second aspect which is also the first embodiment of the second aspect, by a method for amplifying a target L-nucleic acid in the presence of L-nucleotides and a protein comprising an enzymatic activity exhibiting moiety, wherein the enzymatic activity is capable of amplifying the target L-nucleic acid.

In a second embodiment of the second aspect which is also an embodiment of the first embodiment of the second aspect, the enzymatic activity exhibiting moiety consists of an amino acid sequence, wherein the amino acids of the amino acid sequence are D-amino acids.

In a third embodiment of the second aspect which is also an embodiment of the first and the second embodiment of the second aspect, the enzymatic activity exhibiting moiety is a polymerase activity exhibiting moiety.

In a fourth embodiment of the second aspect which is also an embodiment of the first, second and third embodiment of the second aspect, the enzymatic activity is a polymerase activity.

In a fifth embodiment of the second aspect which is also an embodiment of the fourth embodiment of the second aspect, the polymerase activity is a thermostable polymerase activity.

In a sixth embodiment of the second aspect which is also an embodiment of the third, fourth and fifth embodiment of the second aspect, the amino acid sequence of the polymerase activity exhibiting moiety comprises at least 300 amino acids.

In a seventh embodiment of the second aspect which is also an embodiment of the sixth embodiment of the second aspect, the amino acid sequence of the polymerase activity exhibiting moiety comprises between 300 and 900 amino acids, preferably 300 and 600 amino acids, more preferably between 300 and 360 amino acids, most preferably between 340 and 360 amino acids.

In an eighth embodiment of the second aspect which is also an embodiment of the fourth, fifth and sixth embodiment of the second aspect, the polymerase activity is a DNA-polymerase activity.

In a ninth embodiment of the second aspect which is also an embodiment of the eighth embodiment of the second aspect, the DNA-polymerase activity is a DNA-dependent DNA-polymerase activity.

In a tenth embodiment of the second aspect which is also an embodiment of the first, second, third, fourth, fifth, sixth, seventh, eighth and ninth embodiment of the second aspect, the enzymatic activity exhibiting moiety is an enzyme.

In an eleventh embodiment of the second aspect which is also an embodiment of the third, fourth, fifth, sixth, seventh, eighth and ninth embodiment of the second aspect, the polymerase activity exhibiting moiety is a polymerase.

In a twelfth embodiment of the second aspect which is also an embodiment of the first, second, third, fourth, eighth, ninth, tenth and eleventh embodiment of the second aspect, the polymerase activity exhibiting moiety is selected from the group of African Swine Fever Virus Polymerase X, *Thermus thermophilus* polymerase X core domain, rat polymerase beta, eukaryotic olymerase beta, Klenow Fragment, Klenow exo-polymerase, T4 DNA polymerase, Phi29 DNA polymerase, Sequenase, T7 DNA polymerase, SP6 polymerase, DNA polymerase I, polymerase lambda and variants of each and any thereof, wherein preferably the polymerase activity exhibiting moiety is the African Swine Fever Virus Polymerase X or a variant thereof consisting of an amino acid sequence selected of an amino acid sequence selected from the group consisting of amino acid sequence according to SEQ ID NO: 1, amino acid sequence according to SEQ ID NO: 2, amino acid sequence according to SEQ ID NO: 3 and amino acid sequence according to SEQ ID NO: 4.

In a 13$^{th}$ embodiment of the second aspect which is also an embodiment of the first, second, third, fourth, fifth, sixth, seventh, eighth, ninth, tenth and eleventh embodiment of the second aspect, the polymerase activity exhibiting moiety is selected from the group of polymerase DPO4, *Thermococcus litoralis* DNA polymerase, *Pyrococcus* sp. DNA polymerase, *Pyrococcus furiosus* DNA polymerase, Pfuturbo polymerase, *Sulfolobus solfataricus* DNA polymerase, *Thermococcus gorgonarius* DNA polymerase, KOD polymerase, Taq polymerase, Tth polymerase, Pyrobest polymerase, Pwo polymerase, Sac polymerase, Bst polymerase, Poc polymerase, Pab polymerase, Mth polymerase, Pho polymerase, ES4 polymerase, EX-Taq polymerase, LA-Taq polymerase, Expand polymerases, Platinum Taqpolymerases, Hi-Fi polymerase, Tbr polymerase, Tfl polymerase, Tru polymerase, Tac polymerase, Tne polymerase, Tma polymerase, Tih polymerase, Tfi polymerase, AmpliTaq, Stoffel Fragment, 9° Nm DNA Polymerase, Therminator, Therminator II, Phusion High Fidelity Polymerase, Paq5000, Pfx-50, Proofstart, FideliTaq, Elongase and variants thereof, wherein preferably the polymerase activity exhibiting moiety is the Dpo4 polymerase or a variant thereof consisting of an amino acid sequence selected of an amino acid sequence selected from the group consisting of amino acid sequence according to SEQ ID NO: 15, amino acid sequence according to SEQ ID NO: 16, amino acid sequence according to SEQ ID NO: 17, amino acid sequence according to SEQ ID NO: 18, amino acid sequence according to SEQ ID NO: 19, amino acid sequence according to SEQ ID NO: 20, amino acid sequence according to SEQ ID NO: 21 and amino acid sequence according to SEQ ID NO: 22.

In a 14$^{th}$ embodiment of the second aspect which is also an embodiment of the first, second, third, fourth, fifth, sixth, seventh, eighth, ninth, tenth, eleventh, twelfth and 13$^{th}$ embodiment of the second aspect, the step of reacting is carried out under conditions which allow the amplification of the target L-nucleic acid.

In a 15$^{th}$ embodiment of the second aspect which is also an embodiment of the first, second, third, fourth, fifth, sixth, seventh, eighth, ninth, tenth, eleventh, twelfth, 13$^{th}$ and 14$^{th}$ embodiment of the second aspect, the method makes use of at least one primer, preferably two primers, wherein the at least one primer consists of L-nucleotides and optionally a modification.

In a 16$^{th}$ embodiment of the second aspect which is also an embodiment of the 15$^{th}$ embodiment of the second aspect, the primers consist of L-nucleotides.

In a 17$^{th}$ embodiment of the second aspect which is also an embodiment of the first, second, third, fourth, fifth, sixth, seventh, eighth, ninth, tenth, eleventh, twelfth, 13$^{th}$, 14$^{th}$, 15$^{th}$ and 16$^{th}$ embodiment of the second aspect, the target L-nucleic acid consists of L-nucleotides.

In a 18$^{th}$ embodiment of the second aspect which is also an embodiment of the first, second, third, fourth, fifth, sixth, seventh, eighth, ninth, tenth, eleventh, twelfth, 13$^{th}$, 14$^{th}$, 15$^{th}$, 16$^{th}$ and 17$^{th}$ embodiment of the second aspect, the method is a polymerase chain reaction.

In a 19$^{th}$ embodiment of the second aspect which is also an embodiment of the first, second, third, fourth, fifth, sixth, seventh, eighth, ninth, tenth, eleventh, twelfth, 13$^{th}$, 14$^{th}$, 15$^{th}$, 16$^{th}$, 17$^{th}$ and 18$^{th}$ embodiment of the second aspect, the target L-nucleic acid consists of L-DNA.

In a 10$^{th}$ embodiment of the second aspect which is also an embodiment of the first, second, third, fourth, fifth, sixth, seventh, eighth, ninth, tenth, eleventh, twelfth, 13$^{th}$, 14$^{th}$, 15$^{th}$, 16$^{th}$, 17$^{th}$, 18$^{th}$ and 19$^{th}$ embodiment of the second aspect, the target L-nucleic acid consists of 20 to 20,000 L-nucleotides, preferably 30 to 2,000 L-nucleotides, more preferably 40 to 500 L-nucleotides, most preferably 50 to 100 L-nucleotides.

The problem underlying the instant application is also solved in a third aspect which is also the first embodiment of the third aspect, by a protein comprising an enzymatic activity exhibiting moiety, wherein the enzymatic activity exhibiting moiety consists of an amino acid sequence, wherein the amino acids of the amino acid sequence are D-amino acids, wherein the enzymatic activity is capable of adding one or more L-nucleotides to the 3' end of the first L-nucleic acid.

In a second embodiment of the third aspect which is also an embodiment of the first embodiment of the third aspect, the enzymatic activity exhibiting moiety is a polymerase activity exhibiting moiety.

In a third embodiment of the third aspect which is also an embodiment of the first embodiment of the third aspect, the enzymatic activity is a polymerase activity.

In a fourth embodiment of the third aspect which is also an embodiment of the third embodiment of the third aspect, the polymerase activity is a thermostable polymerase activity.

In a fifth embodiment of the third aspect which is also an embodiment of the second, third and fourth embodiment of the third aspect, the amino acid sequence of the polymerase activity exhibiting moiety comprises at least 300 amino acids.

In a sixth embodiment of the third aspect which is also an embodiment of the fifth embodiment of the third aspect, the amino acid sequence of the polymerase activity exhibiting moiety comprises between 300 and 900 amino acids, preferably 300 and 600 amino acids, more preferably between 300 and 360 amino acids, most preferably between 340 and 360 amino acids.

In a seventh embodiment of the third aspect which is also an embodiment of the third, fourth, fifth and sixth embodiment of the third aspect, the polymerase activity is a DNA-polymerase activity.

In an eighth embodiment of the third aspect which is also an embodiment of the seventh embodiment of the third aspect, the DNA-polymerase activity is a DNA-dependent DNA-polymerase activity.

In a ninth embodiment of the third aspect which is also an embodiment of the first, second, third, fourth, fifth, sixth, seventh and eighth embodiment of the third aspect, the enzymatic activity exhibiting moiety is an enzyme.

In a tenth embodiment of the third aspect which is also an embodiment of the second, third, fourth, fifth, sixth, seventh and eighth embodiment of the third aspect, the polymerase activity exhibiting moiety is a polymerase.

In an eleventh embodiment of the third aspect which is also an embodiment of the first, second, third, seventh, eighth, ninth and tenth embodiment of the third aspect, the polymerase activity exhibiting moiety is selected from the group of African Swine Fever Virus Polymerase X, *Thermus thermophilus* polymerase X core domain, rat polymerase beta, eukaryotic polymerase beta, Klenow Fragment, Klenow exo-polymerase, T4 DNA polymerase, Phi29 DNA polymerase, Sequenase, T7 DNA polymerase, SP6 polymerase, DNA polymerase I, polymerase lambda, and variants of each and any thereof, wherein preferably the polymerase activity exhibiting moiety is the African Swine Fever Virus Polymerase X or a variant thereof, consisting of an amino acid sequence selected of an amino acid sequence selected from the group consisting of amino acid sequence according to SEQ ID NO: 1, amino acid sequence according to SEQ ID NO: 2, amino acid sequence according to SEQ ID NO: 3 and amino acid sequence according to SEQ ID NO: 4.

In a twelfth embodiment of the third aspect which is also an embodiment of the first, second, third, fourth, fifth, sixth, seventh, eighth, ninth and tenth embodiment of the third aspect, the polymerase activity exhibiting moiety is selected from the group of polymerase DPO4, *Thermococcus litoralis* DNA polymerase, *Pyrococcus* sp. DNA polymerase, *Pyrococcus furiosus* DNA polymerase, Pfuturbo polymerase, *Sulfolobus solfataricus* DNA polymerase, *Thermococcus gorgonarius* DNA polymerase, KOD polymerase, Taq polymerase, Tth polymerase, Pyrobest polymerase, Pwo polymerase, Sac polymerase, Bst polymerase, Poc polymerase, Pab polymerase, Mth polymerase, Pho polymerase, ES4 polymerase, EX-Taq polymerase, LA-Taq polymerase, Expand polymerases, Platinum Taqpolymerases, Hi-Fi polymerase, Tbr polymerase, Tfl polymerase, Tru polymerase, Tac polymerase, Tne polymerase, Tma polymerase, Tih polymerase, Tfi polymerase, AmpliTaq, Stoffel Fragment, 9° Nm DNA Polymerase, Therminator, Therminator II, Phusion High Fidelity Polymerase, Paq5000, Pfx-50, Proofstart, FideliTaq, Elongase, and variants thereof, wherein preferably the polymerase activity exhibiting moiety is the Dpo4 polymerase or a variant thereof, consisting of an amino acid sequence selected of an amino acid sequence selected from the group consisting of amino acid sequence according to SEQ ID NO: 15, amino acid sequence according to SEQ ID NO: 16, amino acid sequence according to SEQ ID NO: 17, amino acid sequence according to SEQ ID NO: 18, amino acid sequence according to SEQ ID NO: 19, amino acid sequence according to SEQ ID NO: 20, amino acid sequence according to SEQ ID NO: 21 and amino acid sequence according to SEQ ID NO: 22.

The problem underlying the instant application is also solved in a fourth aspect which is also the first embodiment of the fourth aspect, by a polymerase comprising an amino acid sequence according to SEQ ID NO: 15, wherein the amino acids of the amino acid sequence are D-amino acids.

The problem underlying the instant application is also solved in a fifth aspect which is also the first embodiment of the fifth aspect, by a polymerase comprising an amino acid sequence according to SEQ ID NO: 1, wherein the amino acids of the amino acid sequence are D-amino acids.

The problem underlying the instant application is also solved in a sixth aspect which is also the first embodiment of the sixth aspect, by a polymerase variant of a wild type polymerase, wherein the wild type polymerase consists of an amino acid sequence according to SEQ ID NO: 15, and wherein the polymerase variant has polymerase activity, preferably thermostable polymerase activity.

In a second embodiment of the sixth aspect which is also an embodiment of the first embodiment of the sixth aspect, the polymerase variant comprises an amino acid sequence, wherein the amino acid sequence of the polymerase variant differs from the amino acid sequence of the wild type polymerase at at least one amino acid position.

In a third embodiment of the sixth aspect which is also an embodiment of the first and the second embodiment of the sixth aspect, the amino acid sequence of the polymerase variant differs from the amino acid sequence of the wild type polymerase at one or two amino acid positions.

In a fourth embodiment of the sixth aspect which is also an embodiment of the first, second and third embodiment of the sixth aspect, the amino acid sequence of the polymerase variant differs from the amino acid sequence of the wild type polymerase at amino acid position 155 and/or 203 of the amino acid sequence according to SEQ ID NO: 15 or at an amino acid position corresponding thereto, wherein preferably the amino acid(s) at position 155 and/or 203 is/are substituted by a cysteine.

In a fifth embodiment of the sixth aspect which is also an embodiment of the first, second, third and fourth embodiment of the sixth aspect, the polymerase variant consists of an amino acid sequence selected from the group consisting of amino acid sequence according to SEQ ID NO: 16, amino acid sequence according to SEQ ID NO: 17 and amino acid sequence according to SEQ ID NO: 18.

In a sixth embodiment of the sixth aspect which is also an embodiment of the first, second, and third embodiment of the sixth aspect, the polymerase variant consists of an amino acid sequence selected from the group consisting of amino acid sequence according to SEQ ID NO: 19, amino acid sequence according to SEQ ID NO: 20, amino acid sequence according to SEQ ID NO: 21 and amino acid sequence according to SEQ ID NO: 22.

In a seventh embodiment of the sixth aspect which is also an embodiment of the first, second, third, fourth, fifth and sixth embodiment of the sixth aspect, the amino acids of the amino acid sequence of the polymerase variant are D-amino acids.

In an eighth embodiment of the sixth aspect which is also an embodiment of the first, second, third, fourth, fifth and sixth embodiment of the sixth aspect, the amino acids of the amino acid sequence of the polymerase variant are L-amino acids.

The problem underlying the instant application is also solved in a seventh aspect which is also the first embodiment of the seventh aspect, by a polymerase variant of a wild type polymerase, wherein the wild type polymerase consists of an amino acid sequence according to SEQ ID NO: 1, and wherein the polymerase variant has polymerase activity.

In a second embodiment of the seventh aspect which is also an embodiment of the first embodiment of the seventh aspect, the polymerase variant comprises an amino acid sequence, wherein the amino acid sequence of the polymerase variant differs from the amino acid sequence of the wild type polymerase at at least one amino acid position.

In a third embodiment of the seventh aspect which is also an embodiment of the first and the second embodiment of the seventh aspect, the amino acid sequence of the polymerase variant differs from the amino acid sequence of the wild type polymerase at one amino acid position.

In a fourth embodiment of the seventh aspect which is also an embodiment of the first, second and third embodiment of the seventh aspect, the amino acid sequence of the polymerase variant differs from the amino acid sequence of the wild type polymerase at at least one amino acid position, wherein the at least amino acid position is selected from amino acid position 80, amino acid position 86 and amino acid position 124, each of the amino acid sequence according to SEQ ID NO: 1 or at an amino acid position corresponding thereto.

In a fifth embodiment of the seventh aspect which is also an embodiment of the first, second, third and fourth embodiment of the seventh aspect, the polymerase variant consists of an amino acid sequence selected from the group consisting of amino acid sequence according to SEQ ID NO: 2, amino acid sequence according to SEQ ID NO: 3 and amino acid sequence according to SEQ ID NO: 4.

In a sixth embodiment of the seventh aspect which is also an embodiment of the first, second, third, fourth and fifth embodiment of the seventh aspect, the amino acids of the amino acid sequence of the polymerase variant are D-amino acids.

In a seventh embodiment of the seventh aspect which is also an embodiment of the first, second, third, fourth, fifth and sixth embodiment of the seventh aspect, the amino acids of the amino acid sequence of the polymerase variant are L-amino acids.

The problem underlying the instant application is also solved in an eighth aspect which is also the first embodiment of the eight aspect, by a the use of a protein comprising an enzymatic activity exhibiting moiety in a method for adding one or more L-nucleotides to the 3'end of an L-nucleic acid.

The problem underlying the instant application is also solved in a ninth aspect which is also the first embodiment of the ninth aspect, by the use of a protein comprising an enzymatic activity exhibiting moiety in a method for amplifying a target L-nucleic acid in the presence of L-nucleotides.

In a second embodiment of the ninth aspect which is also an embodiment of the first embodiment of the ninth aspect, the method for amplifying a target L-nucleic acid is a polymerase chain reaction.

In a second embodiment of the eighth aspect which is also an embodiment of the first embodiment of the eighth aspect and in a third embodiment of the ninth aspect, the protein is a protein according to any embodiment of the third, fourth, fifth, sixth and seventh aspect, wherein the protein consists of an amino acid sequence, wherein the amino acids of the amino acid sequence are D-amino acids.

The problem underlying the instant application is also solved in a tenth aspect which is also the first embodiment of the tenth aspect, by a method for the identification of a target molecule binding L-nucleic acid molecule comprising the following steps of
(a) generating a heterogeneous population of L-nucleic acid molecules;
(b) contacting the heterogeneous population of L-nucleic acid molecules of step (a) with the target molecule;
(c) separating the L-nucleic acid molecules which are not bound by the target molecule; and
(d) amplifying the L-nucleic acid molecules which are bound by the target molecule, wherein the step of amplification uses a protein according to any embodiment of the third, fourth, fifth, sixth and seventh aspect, wherein the protein consists of an amino acid sequence, wherein the amino acids of the amino acid sequence are D-amino acids.

In a second embodiment of the tenth aspect which is also an embodiment of the first embodiment of the tenth aspect, the method further comprises the step of
(e) sequencing the L-nucleic acid molecules which are bound by the target molecule; and
(f) synthesizing nucleic acid molecules the nucleotide sequence of which is identical to the nucleotide sequence of the L-nucleic acid molecules sequenced in step (e).

In a third embodiment of the tenth aspect which is also an embodiment of the first and the second embodiment of the tenth aspect, the nucleic acid molecules of the heterogeneous population of L-nucleic acid molecules of step (a) comprise at their 5' end and their 3' end a primer binding site and, respectively, a sequence which is complementary to a primer binding site which allow amplification of the L-nucleic acid molecules obtained in step (d) by a polymerase chain reaction, wherein the polymerase used in the polymerase chain reaction is a protein according to any embodiment of the third, fourth, fifth, sixth and seventh aspect, the primers used in the polymerase chain reaction consist of L-nucleotides, and the nucleotides used in the polymerase chain reaction are L-nucleotides.

In a fourth embodiment of the tenth aspect which is also an embodiment of the first, second and third embodiment of the tenth aspect, after step (d) the following step is introduced:

(da) contacting the amplified nucleic acid molecules with the target molecule, wherein step (b) and optionally steps (c) and/or (d) are carried out prior to step (e), wherein steps (da), (b), (c) and optionally (d) are carried out in this order one or several times.

In a fifth embodiment of the tenth aspect which is also an embodiment of the first, second, third and fourth embodiment of the tenth aspect, the target molecule binding L-nucleic acid is a DNA.

In a sixth embodiment of the tenth aspect which is also an embodiment of the first, second, third, fourth and fifth embodiment of the tenth aspect, the target molecule binding L-nucleic acid molecule consists of L-nucleotides.

The problem underlying the instant application is also solved in an eleventh aspect which is also the first embodiment of the eleventh aspect, by a method for producing a protein according to any embodiment of the third, fourth, fifth, sixth and seventh aspect, wherein a) two or more fragments of the protein according to any embodiment of the third, fourth, fifth, sixth and seventh aspect are chemically synthesized, whereby the fragments in their entirety form the amino acid sequence of the protein, preferably the fragments are synthesized by solid phase peptide synthesis, and b) the fragments of step a) are ligated to each other by segment condensation, native chemical ligation, enzymatic ligation or combinations thereof wherein the protein consists of an amino acid sequence, wherein the amino acids of the amino acid sequence are D-amino acids.

In a second embodiment of the eleventh aspect which is also an embodiment of the first embodiment of the eleventh aspect, the enzyme that is used in enzymatic ligation is Clostripain.

The problem underlying the instant application is also solved in a twelfth aspect which is also the first embodiment of the twelfth aspect, by a method for ligating a first D-peptide or a first D-Protein and a second D-peptide or a second D-protein to each other by enzymatic ligation, wherein the first D-peptide or the first D-Protein is protected at its N-terminus by a protection group and is protected at its C-terminus by a 4-guanidinophenylester group, and the second D-peptide or the second D-Protein comprises a free N-terminus and a thioalkylester or thioarylester group at its C-terminus.

In a second embodiment of the twelfth aspect which is also an embodiment of the first embodiment of the twelfth aspect, the enzyme that is used in the enzymatic ligation is Clostripain.

The present inventors have surprisingly found that it is possible to chemically synthesize proteins consisting of D-amino acids which are functionally active, whereby such proteins have a size as typically displayed by a polymerase. More specifically, the present inventors have perceived a method which allows the synthesis of such D-proteins and of D-polymerases, i.e. polymerases consisting of D-amino acids, which are active as polymerases. Based on this surprising finding, the proteins and enzymatic activities required for the enzymatic synthesis of L-nucleic acids and L-nucleic acid molecules are now available. Such enzymatic synthesis of L-nucleic acids and L-nucleic acid molecules comprises, but is not limited to, a method for adding one or more L-nucleotides to the 3'end of a first L-nucleic acid and a method for amplifying a target L-nucleic acid in the presence of L-nucleotides as an L-nucleic acid, i.e. the amplification product is an L-nucleic acid.

As these methods and enzymatic activities are part of an alternative process of identifying spiegelmers making use of, such alternative process of identifying spiegelmers can now be put into practice.

The present inventors have developed a method for adding one or more L-nucleotides to the 3'end of a first L-nucleic acid, wherein the method comprises the step of reacting the one or more L-nucleotides with the first L-nucleic acid in the presence of a protein comprising an enzymatic activity exhibiting moiety, wherein the enzymatic activity is capable of adding one or more L-nucleotides to the 3' end of the first L-nucleic acid.

In a preferred embodiment enzymatic activity is capable of adding of 5 to 20,000 L-nucleotides to the 3' end of the first L-nucleic acid, preferably 10 to 2,000 L-nucleotides, more preferably 50 to 500 L-nucleotides, most preferably 50 to 100 L-nucleotides.

The term adding as preferably used herein is covalent binding between to molecules, according the present invention the covalent binding of an L-nucleic acid and of the at least one or more L-nucleotides to the L-nucleic acid, preferably by forming a 3'-5' phosphodiester linkage between the 3' OH of the first L-nucleic acid and the 5' phosphate of one of the at least one or more L-nucleotides. According to the present invention the L-nucleotide added to the L-nucleic acid forms the 3' end of the L-nucleic acid prolonged by said L-nucleotide.

In a preferred embodiment the method for adding one or more L-nucleotides to the 3'end of a first L-nucleic acid, comprises a second L-nucleic acid, wherein one molecule of the first L-nucleic acid is hybridized to one molecule of the second L-nucleic acid, preferably through Watson-Crick base pairing. In a more preferred embodiment the method allows the synthesize of a third L-nucleic acid that is complementary to the second L-nucleic acid, wherein the third L-nucleic acid comprise the first L-nucleic acid and the L-nucleotides added to the 3'end of the first L-nucleic acid, i.e. to the first L-nucleic acid one or more L-nucleotides are added to 3'end of a first L-nucleic acid resulting in the third L-nucleic acid.

The protein comprising an enzymatic activity exhibiting moiety according to the present invention comprises proteins that soley have an enzymatic activity exhibiting moiety and proteins that have an enzymatic activity exhibiting moiety and other residues or parts, wherein other residues or parts of the protein have no enzymatic activity. According to the present invention the amino acid sequence of the enzymatic activity exhibiting moiety comprises between 300 and 900 amino acids, preferably 300 and 600 amino acids, more preferably between 300 and 360 amino acids, most preferably 340 to 360 amino acids.

The protein comprising an enzymatic activity exhibiting moiety according to the present invention is preferably a polymerase activity exhibiting moiety. The protein comprising a polymerase activity exhibiting moiety according to the present invention comprises polymerases that soley have a polymerase activity exhibiting moiety and polymerases that have an polymerase activity exhibiting moiety and other residues or parts, wherein other residues or parts of the polymerase have no polymerase activity. According to the present invention the amino acid sequence of the polymerase activity exhibiting moiety comprises between 300 and 900 amino acids, preferably 300 and 600 amino acids, more preferably between 300 and 360 amino acids, most preferably 340 to 360 amino acids.

The polymerase activity exhibiting moiety according to the present invention is preferably a thermostable polymerase activity exhibiting moiety, more preferably a thermostable DNA polymerase activity exhibiting moiety and most preferably a thermostable DNA-dependant DNA-polymerase activity exhibiting moiety.

The polymerase activity exhibiting moiety according to the present invention is preferably a DNA-polymerase activity exhibiting moiety, more preferably a DNA-dependant DNA-polymerase activity exhibiting moiety or a thermostable DNA-polymerase activity exhibiting moiety, most preferably a thermostable DNA-dependant DNA-polymerase activity exhibiting moiety.

The term enzymatic activity as used herein is catalyzation of a specific reaction, preferably adding one or more nucleotides to the 3'end of an nucleic acid, amplification of an nucleic acid and/or a polymerase activity, more preferably adding one or more L-nucleotides to the 3'end of an L-nucleic acid and amplification of an L-nucleic acid.

The term polymerase activity according to the present invention is capability of an enzyme the polymerisation of L-nucleotides and/or polymerisation of L-nucleotides to an L-nucleic acid, wherein preferably the L-nucleotides are L-nucleoside triphosphates.

The polymerase activity according to the present invention is preferably a thermostable polymerase activity, more preferably a thermostable DNA polymerase activity and most preferably a thermostable DNA-dependant DNA-polymerase activity.

The polymerase activity according to the present invention is preferably a DNA-polymerase activity, more preferably a DNA-dependant DNA-polymerase or a thermostable DNA-polymerase activity, most preferably a thermostable DNA-dependant DNA-polymerase activity.

Known polymerases are from natural sources or are optimized or mutated variants of polymerases from natural sources. The polymerases consists of chiral building blocks, i.e. L-amino acids. Consequently, the structure of polymerases is inherently chiral as well, resulting in stereospecific substrate recognition. Hence, these enzymes only accept substrate molecules in the adequate, i.e. corresponding chiral configuration. Therefore known polymerases polymerize D-nucleotides or D-nucleoside triphosphates, wherein they use as a template strand a D-nucleic acid consisting of D-nucleotides to synthesize a complementary D-nucleic acid strand consisting of D-nucleotides. Additionally to the template strand the polymerase optionally use a primer that is hybridized to the template strand and consists of D-nucleotides. Since naturally occurring nucleic acids are composed of D-nucleotides and can be processed, e.g. amplified, by proteins and enzymes in particular consisting of L-amino acids, an L-nucleic acid is not recognized by such proteins and enzymes, respectively, consisting of L-amino acids. Accordingly, L-nucleic acids that bind to a target molecule or target structure, also referred to as spiegelmers, cannot be directly obtained by an in vitro selection process using the naturally occurring from of such target molecule or target structure.

The present inventors have surprisingly found that it is possible to produce a polymerase that can add an L-nucleic acid nucleotide to a primer consisting of L-nucleotides that is hybridized to an L-nucleic acid template strand. Moreover, the present inventors have surprisingly found that is possible to produce a polymerase that can be used for the amplification of an L-nucleic acid, preferably in a process that is known as polymerase-chain-reaction (abbr. PCR).

A polymerase is an enzyme that polymerizes nucleoside triphosphates. A polymerases uses a template nucleic acid strand to synthesize a nucleic acid strand which is complementary to the template nucleic acid strand. In addition to the template nucleic acid strand, the polymerase optionally uses a primer that is hybridized based on base complementarity to the template nucleic acid strand. The template nucleic acid strand, the primer and the nucleic acid strand synthesized by the polymerase can independently be either DNA or RNA. A polymerase as preferably used herein includes a DNA polymerase and an RNA-polymerase, preferably a DNA-dependent DNA polymerase, an RNA-dependent DNA polymerase such as a reverse transcriptase, an RNA-dependent RNA polymerase and an RNA-dependent DNA polymerase. More preferably, the polymerase is a thermostable polymerase. A polymerase does not need not to contain all of the amino acids found in a corresponding native or wild type enzyme, but only those which are sufficient to allow the polymerase to carry out a desired catalytic activity. In an embodiment a polymerase activity is catalytic activity which is selected from the group comprising Catalytic activities include, for example, 5'-3' polymerization, 5'-3' exonuclease, and 3'-5' exonuclease activities.

The polymerases according to the present invention consist of D-amino acids and polymerize L-nucleotides or L-nucleoside triphosphates, wherein the polymerases according to the present invention use as a template strand an L-nucleic acid consisting of L-nucleotides to synthesize a complementary L-nucleic acid strand consisting of L-nucleotides. Additionally to the template strand the polymerases according to the present invention optionally use a primer that is hybridized to the template strand and consists of L-nucleotides. The template strand, the primer and synthesized nucleic acid strand can independently be either L-DNA or L-RNA. The polymerases according to the present invention include DNA polymerases consisting of D-amino acids and RNA-polymerases consisting of D-amino acids, preferably DNA-dependent DNA polymerases consisting of D-amino acids, RNA-dependent DNA polymerases such reverse transcriptases consisting of D-amino acids, RNA-dependent RNA polymerases consisting of D-amino acids and RNA-dependent DNA polymerases consisting of D-amino acids. More preferably the polymerase according to the present invention is a thermostable polymerase consisting of D-amino acids. A polymerase according to the present invention need not contain all of the amino acids found in a native enzyme, but only those which are sufficient to allow the polymerases according to the present invention to carry out a desired catalytic activity. Catalytic activities include, for example, 5'-3' polymerization, 5'-3' exonuclease, and 3'-5' exonuclease activities.

A polymerase solely consisting of L-amino acids is preferably referred herein as 'all-L polymerase.'

A polymerase solely consisting of D-amino acids is preferably referred herein as 'all-D polymerase.'

In a preferred embodiment the polymerase according to the present invention is selected from the group of African Swine Fever Virus Polymerase X, *Thermus thermophilus* polymerase X core domain, rat Polymerase beta, eukaryotic Polymerase beta, Klenow Fragment, Klenow exo-polymerase, T4 DNA polymerase, Phi29 DNA polymerase, Sequenase, T7 DNA polymerase, SP6 Polymerase, DNA polymerase I, polymerase lambda, polymerase DPO4, *Thermococcus litoralis* DNA polymerase, *Pyrococcus* sp. DNA polymerase, *Pyrococcus furiosus* DNA polymerase, Pfu-turbo™ polymerase, *Sulfolobus solfataricus* DNA polymerase, *Thermococcus gorgonarius* DNA polymerase, KOD polymerase, Taq polymerase, Tth polymerase, Pyrobest polymerase, Pwo polymerase, Sac polymerase, Bst polymerase, Poc polymerase, Pab polymerase, Mth polymerase, Pho polymerase, ES4 polymerase, EX-Taq™ polymerase, LA-Taq™ polymerase, Expand™ polymerase, Platinum™ Taqpolymerases, polymerase, Tbr polymerase, Tfl polymerase, Tru polymerase, Tac polymerase, Tne polymerase, Tma polymerase, Tih polymerase, Tfi polymerase, AmpliTaq™, Stoffel Fragment, 9° Nm™ DNA Polymerase, Therminator™, Therminator II™, Phusion High Fidelity™ Polymerase, Paq5000™, Pfx-50™, Proofstart™, FideliTaq™, Elongase™, and variants of each and any thereof.

In a more preferred embodiment the polymerase according to the present invention is the African Swine Fever Virus Polymerase X consisting of the amino acid sequence according to SEQ ID NO: 1. In another more preferred embodiment the polymerase according to the present invention is a variant of the African Swine Fever Virus Polymerase X, most preferably a variant of the African Swine Fever Virus Polymerase X of an amino acid sequence selected of an amino acid sequence selected from the group consisting of amino acid sequence according to SEQ ID NO: 2, amino acid sequence according to SEQ ID NO: 3 and amino acid sequence according to SEQ ID NO: 4.

In a more preferred embodiment the polymerase according to the present invention is the polymerase Dpo4 consisting of the amino acid sequence according to SEQ ID NO: 15. In another more preferred embodiment the polymerase according to the present invention is a variant of the polymerase Dpo4, most preferably a variant of the polymerase Dpo4 consisting of an amino acid sequence selected of an amino acid sequence selected from the group consisting of amino acid sequence according to SEQ ID NO: 16, amino acid sequence according to SEQ ID NO: 17, amino acid sequence according to SEQ ID NO: 18, amino acid sequence according to SEQ ID NO: 19, amino acid sequence according to SEQ ID NO: 20, amino acid sequence according to SEQ ID NO: 21 and amino acid sequence according to SEQ ID NO: 22.

A variant of a polymerase is a polymerase that differs from the amino acid sequence of the polymerase at one or more amino acid positions. The position of an amino acid in the amino acid sequence is preferably determined by its position to the N-terminus and the C-terminus of the polymerase and/or its position in respect to amino acids surrounding the amino acid, so that a) if the polymerase is truncated at the N-terminus the position of the amino acid is determined by its position to the C-terminus of the polymerase and in respect to amino acids surrounding the amino acid, b) if the polymerase is truncated at the C-terminus the position of the amino acid is determined by its position to the N-terminus of the polymerase and in respect to amino acids surrounding the amino acid, and b) if the polymerase is truncated at the N-terminus and the C-terminus the position of the amino acid is determined by its position in respect to amino acids surrounding the amino acid.

A polymerases according to the present invention that is thermostable is relatively unaffected by elevated temperatures. In one specific, non-limiting example, a polymerase with of thermostability is unaffected by a temperature of at least 50° C., for example, 50° C., 60° C., 75° C., 80° C., 82° C., 85° C., 88° C., 90° C., 92° C., 95° C., or even higher temperatures.

Within the process of polymerization of L-nucleoside triphosphates the polymerase adds one nucleoside triphosphate to another nucleoside triphosphate, preferably resulting in an oligonucleotide, also referred to as a nucleic acid.

In a preferred embodiment the polymerase adds only one nucleoside triphosphate to one nucleoside triphosphate or to the terminal nucleotide of a nucleic acid, e.g. if the nucleotide is chain terminator nucleotides such as a dideoxynucleotide. Such chain terminator nucleotides are used for sequencing nucleic acids and known by skilled in the art.

The process of polymerization of L-nucleoside triphosphates can be used for amplifying an L-nucleic acid, preferably a target L-nucleic acid.

Amplification is any process that increases the number of copies of a nucleic acid, preferably a target L-nucleic acid.

In a preferred embodiment the target L-nucleic acid consists of 20 to 20,000 L-nucleotides, preferably 30 to 2,000 L-nucleotides, more preferably 40 to 500 L-nucleotides, most preferably 50 to 100 L-nucleotides.

An example of amplification is in which a nucleic acid is contacted with a pair of primers, under conditions that allow for the hybridization of the primers to nucleic acid template. The primers are extended by the polymerase by adding one or more nucleoside triphosphates to the primer under suitable conditions, dissociated from the nucleic acid template, and then re-annealed, extended, and dissociated to amplify the number of copies of the nucleic acid molec. The product of in vitro amplification can be characterized by electrophoresis, restriction endonuclease cleavage patterns, oligonucleotide hybridization or ligation, and/or nucleic acid sequencing, using standard techniques.

Alternative in vitro amplification techniques are known by a person skilled in the art including transcription-free isothermal amplification, strand displacement amplification, and NASBA™ RNA transcription-free amplification.

Some of the amplifications method relies on thermal cycling, consisting of cycles of repeated heating and cooling of the reaction for melting of a nucleic acid, preferably a double-stranded nucleic acid, and enzymatic replication of the nucleic acid. These thermal cycling steps are necessary first to physically separate the two strands in of double stranded nucleic acid at a high temperature in a process called nucleic acid melting. At a lower temperature, each strand is then used as the template in nucleic acid synthesis by the polymerase to selectively amplify the target nucleic acid. Primers containing sequences complementary to the target region along with a polymerase (after which the method is named) are key components to enable selective and repeated amplification. As the amplification method based in thermal cycling progresses, the nucleic acid generated is itself used as a template for replication, setting in motion a chain reaction in which the nucleic acid template is exponentially amplified.

The most prominent amplification method by thermal amplification is the polymerase chain reaction (abbr. PCR).

Primers are short nucleic acid molecules consisting of DNA or RNA or combinations thereof, preferably DNA oligonucleotides 10 nucleotides or more in length. More preferably, longer primers can be about 15, 20, or 25 nucleotides or more in length. Primers can be annealed to a complementary target nucleic acid strand by nucleic acid hybridization to form a hybrid between the primer and the target nucleic acid strand, and then the primer extended along the target nucleic acid strand by a polymerase Primer pairs can be used for amplification of a nucleic acid, e.g., by the PCR or other nucleic-acid amplification methods known in the art.

The use the polymerase of the present invention consisting of D-amino acids makes is necessary that the primer and the complementary target nucleic acid strand consist of L-nucleotides. Preferably at least one primer consists of L-nucleotides and optionally a modification.

Methods for preparing and using nucleic acid primers and probes are described, for example, in Sambrook et al. (Sambrock et al., 1989). PCR primer pairs can be derived from a known sequence, for example, by using computer programs intended for that purpose such as Primer. One of ordinary skill in the art will appreciate that the specificity of a particular probe or primer increases with its length.

The polymerases according to the present invention consist of D-amino acids. Because of that the polymerases according to the present invention consisting of D-amino acids can not be isolated from natural sources and can not be produced by recombinant expression using bacteria, yeast, fungi, viruses or animal cells and has to be produced by a chemical process, preferably such as solid-phase peptide synthesis (abbr. SPPS) in combination with ligation methods.

Solid-phase peptide synthesis is the state-of-the-art for the synthesis of peptides or fragments of proteins: Small solid beads, insoluble yet porous, are treated with functional units ('linkers') on which peptide chains can be built. The peptide will remain covalently attached to the bead until cleaved from it by a reagent such as anhydrous hydrogen fluoride or trifluoroacetic acid. The peptide is thus 'immobilized' on the solid-phase and can be retained during a filtration process, whereas liquid-phase reagents and by-products of synthesis are flushed away. The general principle of SPPS is one of repeated cycles of coupling-wash-deprotection-wash. The free N-terminal amine of a solid-phase attached peptide is coupled (see below) to a single N-protected amino acid unit. This unit is then deprotected, revealing a new N-terminal amine to which a further amino acid may be attached. The superiority of this technique partially lies in the ability to perform wash cycles after each reaction, removing excess reagent with all of the growing peptide of interest remaining covalently attached to the insoluble resin. There are two majorly used forms of SPPS—Fmoc and Boc. The N-termini of amino acid monomers is protected by either of these two groups and added onto a deprotected amino acid chain. SPPS is limited by yields, and typically peptides and proteins in the range of 70 amino acids are pushing the limits of synthetic accessibility. Synthetic difficulty also is sequence dependent. Larger synthetic oligopeptides and proteins can be accessed by using ligation methods such as fragment condensation, native chemical ligation or enzymatic ligation to couple two peptides together. However, the largest D-protein synthesized so far is the D-protein form of the angiogenic protein vascular endothelial growth factor (abbr. VEGF-A) consisting of 102 D-amino acids (Mandal et al., 2012), Fragment condensation uses peptides wherein the side chains of the amino acids of the peptide are fully protected by chemical groups and the peptide are coupled in solution.

Native chemical ligation is carried out in aqueous solution. The challenge is the preparation of the necessary unprotected peptide-thioester building block. In native chemical ligation, the thiolate group of an N-terminal cysteine residue of an unprotected peptide 2 attacks the C-terminal thioester of a second unprotected peptide 1 in an aqueous buffer at pH 7.0, 20° C.<T<37° C. This reversible transthioesterification step is chemoselective and regioselective and leads to form a thioester intermediate 3. This intermediate rearranges by an intramolecular S,N-acyl shift that results in the formation of a native amide ('peptide') bond 4 at the ligation site.

As shown in the examples the inventors could surprisingly show that a C-terminal thioester that is necessary for native chemical ligation is stable under the conditions of enzymatic ligation, so that the native chemical ligation and enzymatic ligation can be used in combination.

Enzymatic ligation of D-peptides works by the use of proteases comprising the following steps: (a) preparation of an amino component, where said amino component is a uniquely D-peptide, (b) preparation of the carboxy component, where said carboxy component comprises a leaving group and is a uniquely D-peptide and (c) reaction of the amino component and the carboxy component in the presence of a protease to form a peptide bond between the amino component and the carboxy component with cleavage of the leaving group to give the uniquely D-polypeptide (see WO2003047743). Preferably the protease is Clostripain.

A polymerase of the present invention shall also comprise a polymerase which is essentially homologous to the polymerase of the present invention and in particular to the particular sequence(s) disclosed herein. The term substantially homologous shall be understood such as the homology is at least 75%, preferably 85%, more preferably 90% and most preferably more that 95%, 96%, 97%, 98% or 99%.

A polymerase activity exhibiting moiety of the present invention shall also comprise a polymerase activity exhibiting moiety which is essentially homologous to the polymerase activity exhibiting moiety of the present invention and in particular to the particular sequence(s) disclosed herein. The term substantially homologous shall be understood such as the homology is at least 75%, preferably 85%, more preferably 90% and most preferably more that 95%, 96%, 97%, 98% or 99%.

The actual percentage of homologous amino acids present in the polymerase of the present invention or polymerase activity exhibiting moiety of the present invention invention will depend on the total number of amino acids present in the polymerase or polymerase activity exhibiting moiety. The percent modification can be based upon the total number of amino acids present in the polymerase or polymerase activity exhibiting moiety.

The homology between two polymerases or two polymerase activity exhibiting moieties can be determined as known to the person skilled in the art. More specifically, a sequence comparison algorithm may be used for calculating the percent sequence homology for the test sequence(s) relative to the reference sequence, based on the designated program parameters. The test sequence is preferably the polymerase or polymerase activity exhibiting moiety which is said to be homologous or to be tested whether it is homologous, and if so, to what extent, to a different polymerase or polymerase activity exhibiting moiety, whereby such different polymerase or polymerase activity exhibiting moiety is also referred to as the homology reference sequence. Optimal alignment of amino acid sequences of the polymerase for comparison can be conducted, e.g., by the local homology algorithm of Smith & Waterman (Smith & Waterman, 1981) by the homology alignment algorithm of Needleman & Wunsch (Needleman & Wunsch, 1970) by the search for similarity method of Pearson & Lipman (Pearson & Lipman, 1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection.

One example of an algorithm that is suitable for determining percent sequence identity is the algorithm used in the basic local alignment search tool (hereinafter "BLAST"), see, e.g. Altschul et al (Altschul et al. 1990 and Altschul et al, 1997). Software for performing BLAST analyses is publicly available through the National Center for Biotechnology Information (hereinafter "NCBI"). The default parameters used in determining sequence identity using the software available from NCBI, e.g., BLASTN (for nucleotide sequences) and BLASTP (for amino acid sequences) are described in McGinnis et al (McGinnis et al, 2004).

A polymerase of the present invention shall also comprise polymerase which has a certain degree of identity relative to polymerase of the present invention and in particular to the particular polymerase of the present invention disclosed herein and defined by their amino acid sequence. More preferably, the instant invention also comprises those polymerases which have an identity of at least 75%, preferably 85%, more preferably 90% and most preferably more than 95%, 96%, 97%, 98% or 99% relative to the polymerase of the present invention and in particular to the particular polymerase of the present invention disclosed herein and defined by their amino acid sequence or a part thereof.

A polymerase activity exhibiting moiety of the present invention shall also comprise polymerase activity exhibiting moiety which has a certain degree of identity relative to polymerase activity exhibiting moiety of the present invention and in particular to the particular polymerase activity exhibiting moiety of the present invention disclosed herein and defined by their amino acid sequence. More preferably, the instant invention also comprises those polymerase activity exhibiting moieties which have an identity of at least 75%, preferably 85%, more preferably 90% and most preferably more than 95%, 96%, 97%, 98% or 99% relative to the polymerase activity exhibiting moiety of the present invention and in particular to the particular polymerase activity exhibiting moiety of the present invention disclosed herein and defined by their amino acid sequence or a part thereof.

In connection with the instant application the terms nucleic acid molecule and nucleic acid are used in an interchangeable manner if not explicitly indicated to the contrary.

As preferably used herein "nucleic acid" and "nucleic acid" refer to polynucleotides or oligonucleotides such as deoxyribonucleic acid (abbr. DNA) and ribonucleic acid (abbr. RNA). Moreover, the term "a nucleic acid" includes a plurality of nucleic acids. The terms "nucleic acid" and "nucleic acids" should also be understood to include, as equivalents, variants and analogs of either RNA or DNA made from nucleotide analogs, single (sense or antisense) and double-stranded polynucleotides or oligonucleotides. Deoxyribonucleotides include deoxyadenosine, deoxycytidine, deoxyguanosine and deoxythymidine. Ribonucleotides include adenosine, cytidine, guanosine and uridine. Reference to a nucleic acid molecule as a "polynucleotide" is used in its broadest sense to mean two or more nucleotides or nucleotide analogs linked by a covalent bond, including single stranded or double stranded molecules. The term "oligonucleotide" also is used herein to mean two or more nucleotides or nucleotide analogs linked by a covalent bond, although as defined herein oligonucleotides comprise less one hundred nucleotides.

The nucleic acid is characterized in that all of the consecutive nucleotides forming the nucleic acid are linked with or connected to each other by one or more than one covalent bond. More specifically, each of such nucleotides is linked with or connected to two other nucleotides, preferably through phosphodiester bonds or other bonds, forming a stretch of consecutive nucleotides. In such arrangement, however, the two terminal nucleotides, i.e. preferably the nucleotide at the 5' end and at the 3' end, are each linked to a single nucleotide only under the proviso that such arrangement is a linear and not a circular arrangement and thus a linear rather than a circular molecule.

In another embodiment of the present application the nucleic acid comprises at least two groups of consecutive nucleotides, whereby within each group of consecutive nucleotides each nucleotide is linked with or connected to two other nucleotides, preferably through phosphodiester bonds or other bonds, forming a stretch of consecutive nucleotides. In such arrangement, however, the two terminal nucleotides, i.e. preferably the nucleotide at the 5' end and at the 3' end, are each linked to a single nucleotide only. In such embodiment, the two groups of consecutive nucleotides, however, are not linked with or connected to each other through a covalent bond which links one nucleotide of one group and one nucleotide of another or the other group through a covalent bond, preferably a covalent bond formed between a sugar moiety of one of said two nucleotides and a phosphor moiety of the other of said two nucleotides or nucleosides. In an alternative embodiment, the two groups of consecutive nucleotides, however, are linked with or connected to each other through a covalent bond which links one nucleotide of one group and one nucleotide of another or the other group through a covalent bond, preferably a covalent bond formed between a sugar moiety of one of said two nucleotides and a phosphor moiety of the other of said two nucleotides or nucleosides. Preferably, the at least two groups of consecutive nucleotides are not linked through any covalent bond. In another preferred embodiment, the at least two groups are linked through a covalent bond which is different from a phosphodiester bond.

The term nucleic acid preferably also encompasses either a D-nucleic acid or a L-nucleic acid. Preferably, the nucleic acid is L-nucleic acid 1. In addition it is possible that one or several parts of the nucleic acid is present as a D-nucleic acid and at least one or several parts of the nucleic acid is an L-nucleic acid. The term "part" of the nucleic acid shall mean as little as one nucleotide. Such nucleic acid is generally referred to herein as D- and L-nucleic acid, respectively. Therefore, in a preferred embodiment, the nucleic acid according to the present invention consist of L-nucleotides and comprise at least one D-nucleotide. Preferably, such D-nucleotide is attached at a terminus of any of the stretches and of any nucleic acid.

L-nucleic acid as used herein is a nucleic acid consisting of L-nucleotides, preferably consisting completely of L-nucleotides.

D-nucleic acid as used herein is nucleic acid consisting of D-nucleotides, preferably consisting completely of D-nucleotides.

Also, if not indicated to the contrary, any nucleotide sequence is set forth herein in 5'→3' direction.

Irrespective of whether the nucleic acid consists of D-nucleotides, L-nucleotides or a combination of both with the combination being e.g. a random combination or a defined sequence of stretches consisting of at least one L-nucleotide and at least one D-nucleic acid, the nucleic acid molecule may consist of desoxyribonucleotide(s), ribonucleotide(s) or combinations thereof.

Regardless of whether the nucleic acid is a D-nucleic acid, an L-nucleic acid, a mixture thereof, a DNA, or an RNA, or each and any combination thereof, the term nucleic acid as preferably used herein shall also encompass single-stranded nucleic acid and double-stranded nucleic acid, whereby preferably the nucleic acid molecule as subjected to the method according to the present invention is a single-stranded nucleic acid.

The term nucleic acid as preferably used herein, shall also encompass a modified nucleic acid. The modified nucleic acid can be a nucleotide-modified RNA or a nucleotide-modified DNA molecule, whereby the RNA or DNA molecules are extensively modified at the individual nucleotides to enhance stability by modification with nuclease resistant groups, for example, 2'-amino, 2'-C-allyl, 2'-fluoro, 2'-O-methyl, 2'-H (for a review see Usman & Cedergren, 1992).

The term nucleic acid as preferably used herein, shall also encompass a fully closed nucleic acid. A fully closed, i.e. circular structure for the nucleic acid is realized if the nucleic acid the nucleotide sequence of which is to be determined according to the present invention, is closed, preferably through a covalent linkage, whereby more preferably such covalent linkage is made between the 5' end and the 3' end of the nucleic acid molecules sequences as disclosed herein.

The term nucleic acid as preferably used shall also encompass any nucleic acid molecule which comprises a non-nucleic acid molecule moiety. Such non-nucleic acid molecule moiety may be selected from a group comprising peptides, oligopeptides, polypeptides, proteins, carbohydrates, various groups as will be outlined in more detail in the following. The term nucleic acid e shall thus also encompass conjugates and/or complexes comprising at least one nucleic acid moiety and at least one further moiety that can be used to facilitate delivery of nucleic acid molecules into a biological system, such as a cell. The conjugates and complexes provided can impart therapeutic activity by transferring therapeutic compounds across cellular membranes, altering the pharmacokinetics, and/or modulating the localization of nucleic acid of the invention. These kinds of conjugates and complexes are preferably suitable for the delivery of molecules, including, but not limited to, small molecules, lipids, phospholipids, nucleosides, nucleotides, nucleic acids, antibodies, toxins, negatively charged polymers and other polymers, for example proteins, peptides, hormones, carbohydrates, polyethylene glycols, or polyamines, across cellular membranes. In general, the transporters described are designed to be used either individually or as part of a multi-component system, with or without degradable linkers. These compounds are expected to improve delivery and/or localization of nucleic acid molecules into a number of cell types originating from different tissues, in the presence or absence of serum (see U.S. Pat. No. 5,854,038). Conjugates of the molecules described herein can be attached to biologically active molecules via linkers that are biodegradable, such as biodegradable nucleic acid linker molecules.

As will be detailed in the following in connection with the nucleic acid the sequence of which is to be determined, the non-nucleic acid moiety may be a PEG moiety, i.e. a poly(ethylene glycol) moiety, or a HES moiety, i.e. a hydroxyethyl starch moiety.

The non-nucleic acid moiety and preferably the PEG and/or HES moiety can be attached to the nucleic acid molecule either directly or through a linker. It is also within the present invention that the nucleic acid molecule comprises one or more modifications, preferably one or more PEG and/or HES moiety. In an embodiment the individual linker molecule attaches more than one PEG moiety or HES moiety to a nucleic acid molecule. The linker used in connection with the present invention can itself be either linear or branched. These kind of linkers are known to the ones skilled in the art and are further described in the patent applications WO 2005/074993 and WO 2003/035665.

In a preferred embodiment the linker is a biodegradable linker. The biodegradable linker allows to modify the characteristics of the nucleic acid molecules in terms of, among other, residence time in the animal body, preferably in the human body, due to release of the modification from the nucleic acid molecules. Usage of a biodegradable linker may allow a better control of the residence time of the nucleic acid molecules. A preferred embodiment of such biodegradable linkers are biodegradable linkers such as those described in but not restricted to the international patent applications WO 2006/052790, WO 2008/034122, WO 2004/092191 and WO 2005/099768, whereby in the international patent applications WO 2004/092191 and WO 2005/099768, the linker is part of a polymeric oligonucleotide prodrug, that consists of one or two modifications as described herein, a nucleic acid molecule and the biodegradable linker in between.

As preferably used herein, "nucleotides" include, but are not limited to, the naturally occurring DNA nucleoside mono-, di-, and triphosphates: deoxyadenosine mono-, di- and triphosphate; deoxyguanosine mono-, di- and triphosphate; deoxythymidine mono-, di- and triphosphate; and deoxycytidine mono-, di- and triphosphate. (referred to herein as dA, dG, dT and dC or A, G, T and C, respectively). The term nucleotides also includes the naturally occurring RNA nucleoside mono-, di-, and triphosphates: adenosine mono-, di- and triphosphate; guanine mono-, di- and triphosphate; uridine mono-, di- and triphosphate; and cytidine mono-, di- and triphosphate (referred to herein as A, G, U and C, respectively) refers to a base-sugar-phosphate combination that is the monomeric unit of a nucleic acid molecule, i. e., a DNA molecule and an RNA molecule. However, in other words, the term "nucleotides" refers to any compound containing a cyclic furanoside-type sugar (p-D/L-ribose in RNA and P-D/L-2'-deoxyribose in DNA), which is phosphorylated at the 5' position and has either a purine or pyrimidine-type base attached at the C-1'sugar position via a glycosol C1'-linkage. The nucleotides may be natural or synthetic, including a nucleotide that has been mass-modified including, inter alia, nucleotides having modified nucleosides with modified bases (e. g., 5-methyl cytosine) and modified sugar groups (e. g., 2'-O-methyl ribosyl, 2'-O-methoxyethyl ribosyl, 2'-fluoro ribosyl, 2'-amino ribosyl, and the like).

The term "nucleobase" covers the naturally occurring nucleobases adenine (A), guanine (G), cytosine (C), thymine (T) and uracil (U) as well as non-naturally occurring nucleobases such as xanthine, diaminopurine, 8-oxo-N6-methyladenine, 7-deazaxanthine, 7-deazaguanine, N4,N4-ethanocytosin, N6,N6-ethano-2,6-diaminopurine, 5-methylcytosine, 5~(C3-C6)-alkynyl-cytosine, 5-fluorouracil, 5-bromouracil, pseudoisocytosine, 2-hydroxy-5-methyl-4-triazolopyridin, isocytosine, isoguanine, inosine and the "non-naturally occurring" nucleobases described in the U.S. Pat. No. 5,432,272, in the publication of Freier & Altmann (Freier & Altmann, 1997). The term "nucleobase" thus includes not only the known purine and pyrimidine heterocycles, but also heterocyclic analogues and tautomers thereof.

It is within the present invention that the single-stranded nucleic acid can form distinct and stable three-dimensional structures and specifically bind to a target molecule like antibodies. Such nucleic acid molecules composed of D-nucleotides are called aptamers. Aptamers can be identified against several target molecules, e.g. small molecules, proteins, nucleic acids, and even cells, tissues and organisms and can inhibit the in vitro and/or in vivo function of the specific target molecule. Aptamers are usually identified by a target-directed selection process, called in vitro selection or Systematic Evolution of Ligands by Exponential Enrichment (abbr. SELEX) (Bock et al, 1992; Ellington & Szostak, 1990; Tuerk & Gold, 1990). Non-modified aptamers are cleared rapidly from the bloodstream, with a half-life of minutes to hours, mainly due to nuclease degradation and clearance from the body by the kidneys, a result of the aptamer's inherently low molecular weight. Hence, in order to use aptamers therapeutically they have to be modified at the 2' position of the sugar (e.g. ribose) backbone (Burmester et al, 2006).

The omnipresent nucleases which account for the instability of aptamers consist of chiral building blocks, i.e. L-amino acids. Consequently, the structure of nucleases is inherently chiral as well, resulting in stereospecific substrate recognition. Hence, these enzymes only accept substrate molecules in the adequate chiral configuration. Since aptamers and naturally occurring nucleic acid molecules are composed of D-nucleotides, an L-oligonucleotide should escape from enzymatic recognition and subsequent degradation. Due to the same principle, unfortunately in this case, nature developed no enzymatic activity to amplify such mirror-image nucleic acids. Accordingly, L-nucleic acid aptamers cannot be directly obtained employing the SELEX process. The principles of stereochemistry, though, reveal a detour which eventually leads to the desired functional L-nucleic acid aptamers.

If an in vitro selected (D−)aptamer binds its natural target, the structural mirror-image of this aptamer binds with the same characteristics the mirror-image of the natural target. Here, both interaction partners have the same (unnatural) chirality. Due to the homochirality of life and most biochemical compounds, such enantio-RNA ligands, of course, would be of limited practical use. If, on the other hand, the SELEX process is carried out against an (unnatural) mirror-image target, an aptamer recognizing this (unnatural) target will be obtained. The corresponding mirror-image configuration of said aptamer—the desired L-aptamer—in turn recognizes the natural target. This mirror-image selection process for the generation of biostable nucleic acid molecule was published first in 1996 (Klussmann et al, 1996; Nolte et al, 1996) and results in the generation of functional mirror-image nucleic acid molecule ligands that display not only high affinity and specificity for a given target molecule, but at the same time also biological stability. It is within the present invention that the single-stranded nucleic acid molecule is such a ligand-binding L-nucleic acid that is referred as 'spiegelmer' (from the German word 'Spiegel', mirror) (see 'The Aptamer Handbook'; eds. Klussmann, 2006)

Among others, the nucleic acids according to the present invention may comprise a modification, which preferably allows the detection of the nucleic acids according to the present invention. Such a modification is preferably selected from the group comprising radioactive, enzymatic and fluorescent labels. Such modification is also selected from D-nucleotides that itself can by modified by a modification selected from the group comprising radioactive, enzymatic and fluorescent labels.

The various SEQ.ID.Nos., the chemical nature of the nucleic acids, peptides, oligopetides and protein as used herein, the actual sequence thereof and the internal reference number is summarized in the following table.

TABLE 1 (A)

SEQUENCES REFERRED TO IN THIS APPLICATION

| SEQ ID NO: | Type | Sequence | Internal Reference |
|---|---|---|---|
| 1 | Protein | MLTLIQGKKIVNHLRSRLAFEYNGQLIKILSKNIVAVGSLRREEKMLNDVDLLIIVPEKK LLKHVLPNIRIKGLSFSVKVCGERKCVLFIEWEKKTYQLDLFTALAEEKPYAIFHFTGPV SYLIRIRAALKKKNYKLNQYGLFKNQTLVPLKITTEKELIKELGFTYRIPKKRL | Pol-X, polymerase X |
| 2 | Protein | MLTLIQGKKIVNHLRSRLAFEYNGQLIKILSKNIVAVGSLRREEKMLNDVDLLIIVPEKK LLKHVLPNIRIKGLSFSVKGCGERKCVLFIEWEKKTYQLDLFTALAEEKPYAIFHFTGPV SYLIRIRAALKKKNYKLNQYGLFKNQTLVPLKITTEKELIKELGFTYRIPKKRL | Pol-X V80G, polymerase X variant V80G |
| 3 | Protein | MLTLIQGKKIVNHLRSRLAFEYNGQLIKILSKNIVAVGSLRREEKMLNDVDLLIIVPEKK LLKHVLPNIRIKGLSFSVKACGERKCVLFIEWEKKTYQLDLFTALAEEKPYAIFHFTGPV SYLIRIRAALKKKNYKLNQYGLFKNQTLVPLKITTEKELIKELGFTYRIPKKRL | Pol-X V80A, polymerase X variant V80A |
| 4 | Protein | MLTLIQGKKIVNHLRSRLAFEYNGQLIKILSKNIVAVGSLRREEKMLNDVDLLIIVPEKK LLKHVLPNIRIKGLSFSVKVCGERKCVLFIEWEKKTYQLDLFTALAEEKPYAIFHFTGPV SYLGRIRAALKKKNYKLNQYGLFKNQTLVPLKITTEKELIKELGFTYRIPKKRL | Pol-X I124G, polymerase X variant I124G |
| 5 | Protein | MLTLIQGKKIVNHLRSRLAFEYNGQLIKILSKNIVAVGSLRREEKMLNDVDLLIIVPEKK LLKHVLPNIRIKGLSFSVKVCGERKSVLFIEWEKKTYQLDLFTALAEEKPYAIFHFTGPV SYLIRIRAALKKKNYKLNQYGLFKNQTLVPLKITTEKELIKELGFTYRIPKKRL | Pol-X C86S, polymerase X variant C86S |
| 6 | D/L-DNA | D(GG)-L(GATCACAGTGAGTAC) | MJ_1_58_MD |
| 7 | L-DNA | Phosphate-GTAAAACGACGGCCAGT | MJ_1_143_LD |
| 8 | L-DNA | ACTGGCCGTCGTTTTACAGTACTCACTGTGATC | MJ_1_145_LD |
| 9 | L-DNA | ACTGGCCGTCGTTTTACCGTACTCACTGTGATC | MJ_1_146_LD |
| 10 | L-DNA | ACTGGCCGTCGTTTTACGGTACTCACTGTGATC | MJ_1_147_LD |
| 11 | L-DNA | ACTGGCCGTCGTTTTACTGTACTCACTGTGATC | MJ_1_144_LD |
| 12 | D/L-DNA | D(GG)-L(GATCACAGTGAGTAC) | MJ_1_58_MD |

TABLE 1 (A)-continued

SEQUENCES REFERRED TO IN THIS APPLICATION

| SEQ ID NO: | Type | Sequence | Internal Reference |
|---|---|---|---|
| 13 | L-DNA | Phosphate-ACGACGGCCAGT | MJ_1_59_LD |
| 14 | L-DNA | ACTGGCCGTCGTTCTATTGTACTCACTGTGATC | MJ_1_57_LD |
| 15 | Protein | MIVLFVDFDYFYAQVEEVLNPSLKGKPVVVCVFSGRFEDSGAVATANYEARKFGVKA<br>GIPIVEAKKILPNAVYLPMRKEVYQQVSSRIMNLLREYSEKIEIASIDEAYLDISDKVRD<br>YREAYNLGLEIKNKILEKEKITVTVGISKNKVFAKIAADMAKPNGIKVIDDEEVKRLIRE<br>LDIADVPGIGNITAEKLKKLGINKLVDTLSIEFDKLKGMIGEAKAKYLISLARDEYNEPI<br>RTRVRKSIGRIVTMKRNSRNLEEIKPYLFRAIEESYYKLDKRIPKAIHVVAVTEDLDIVS<br>RGRTFPHGISKETAYSESVKLLQKILEEDERKIRRIGVRFSKFIEAIGLDKFFDT | Dpo4, polymerase Dpo4 |
| 16 | Protein | MIVLFVDFDYFYAQVEEVLNPSLKGKPVVVCVFSGRFEDSGAVATANYEARKFGVKA<br>GIPIVEAKKILPNAVYLPMRKEVYQQVSSRIMNLLREYSEKIEIASIDEAYLDISDKVRD<br>YREAYNLGLEIKNKILEKEKITVTVGISKNKVFAKIA<u>C</u>DMAKPNGIKVIDDEEVKRLIRE<br>LDIADVPGIGNITAEKLKKLGINKLVDTLSIEFDKLKGMIGEAKAKYLISLARDEYNEPI<br>RTRVRKSIGRIVTMKRNSRNLEEIKPYLFRAIEESYYKLDKRIPKAIHVVAVTEDLDIVS<br>RGRTFPHGISKETAYSESVKLLQKILEEDERKIRRIGVRFSKFIEAIGLDKFFDT | Dpo44 A155C, polymerase Dpo4 variant A155C |
| 17 | Protein | MIVLFVDFDYFYAQVEEVLNPSLKGKPVVVCVFSGRFEDSGAVATANYEARKFGVKA<br>GIPIVEAKKILPNAVYLPMRKEVYQQVSSRIMNLLREYSEKIEIASIDEAYLDISDKVRD<br>YREAYNLGLEIKNKILEKEKITVTVGISKNKVFAKIAADMAKPNGIKVIDDEEVKRLIRE<br>LDIADVPGIGNITAEKLKKLGINKL<u>C</u>DTLSIEFDKLKGMIGEAKAKYLISLARDEYNEPI<br>RTRVRKSIGRIVTMKRNSRNLEEIKPYLFRAIEESYYKLDKRIPKAIHVVAVTEDLDIVS<br>RGRTFPHGISKETAYSESVKLLQKILEEDERKIRRIGVRFSKFIEAIGLDKFFDT | Dpo4 V203C, polymerase Dpo4 variant V203C, |
| 18 | Protein | MIVLFVDFDYFYAQVEEVLNPSLKGKPVVVCVFSGRFEDSGAVATANYEARKFGVKA<br>GIPIVEAKKILPNAVYLPMRKEVYQQVSSRIMNLLREYSEKIEIASIDEAYLDISDKVRD<br>YREAYNLGLEIKNKILEKEKITVTVGISKNKVFAKIA<u>C</u>DMAKPNGIKVIDDEEVKRLIRE<br>LDIADVPGIGNITAEKLKKLGINKL<u>C</u>DTLSIEFDKLKGMIGEAKAKYLISLARDEYNEPI<br>RTRVRKSIGRIVTMKRNSRNLEEIKPYLFRAIEESYYKLDKRIPKAIHVVAVTEDLDIVS<br>RGRTFPHGISKETAYSESVKLLQKILEEDERKIRRIGVRFSKFIEAIGLDKFFDT | Dpo4 A155C/V203C, polymerase Dpo4 variant A155C/V203C, |
| 19 | Protein | MIVLFVDFDYFYAQVEEVLNPSLKGKPVVV<u>S</u>VFSGRFEDSGAVATANYEARKFGVKA<br>GIPIVEAKKILPNAVYLPMRKEVYQQVSSRIMNLLREYSEKIEIASIDEAYLDISDKVRD<br>YREAYNLGLEIKNKILEKEKITVTVGISKNKVFAKIAADMAKPNGIKVIDDEEVKRLIRE<br>LDIADVPGIGNITAEKLKKLGINKLVDTLSIEFDKLKGMIGEAKAKYLISLARDEYNEPI<br>RTRVRKSIGRIVTMKRNSRNLEEIKPYLFRAIEESYYKLDKRIPKAIHVVAVTEDLDIVS<br>RGRTFPHGISKETAYSESVKLLQKILEEDERKIRRIGVRFSKFIEAIGLDKFFDT | Dpo4 C31S, polymerase Dpo4 variant C31S, |
| 20 | Protein | MIVLFVDFDYFYAQVEEVLNPSLKGKPVVVCVFSGRFEDSGAVATANYEARKFGVKA<br>GIPIVEAKKILPNAVYLPMRKEVYQQV<u>C</u>SRIMNLLREYSEKIEIASIDEAYLDISDKVRD<br>YREAYNLGLEIKNKILEKEKITVTVGISKNKVFAKIAADMAKPNGIKVIDDEEVKRLIRE<br>LDIADVPGIGNITAEKLKKLGINKLVDTLSIEFDKLKGMIGEAKAKYLISLARDEYNEPI<br>RTRVRKSIGRIVTMKRNSRNLEEIKPYLFRAIEESYYKLDKRIPKAIHVVAVTEDLDIVS<br>RGRTFPHGISKETAYSESVKLLQKILEEDERKIRRIGVRFSKFIEAIGLDKFFDT | Dpo4 S85C, polymerase Dpo4 variant S85C |
| 21 | Protein | MIVLFVDFDYFYAQVEEVLNPSLKGKPVVVCVFSGRFEDSGAVATANYEARKFGVKA<br>GIPIVEAKKILPNAVYLPMRKEVYQQVS<u>C</u>RIMNLLREYSEKIEIASIDEAYLDISDKVRD<br>YREAYNLGLEIKNKILEKEKITVTVGISKNKVFAKIAADMAKPNGIKVIDDEEVKRLIRE<br>LDIADVPGIGNITAEKLKKLGINKLVDTLSIEFDKLKGMIGEAKAKYLISLARDEYNEPI<br>RTRVRKSIGRIVTMKRNSRNLEEIKPYLFRAIEESYYKLDKRIPKAIHVVAVTEDLDIVS<br>RGRTFPHGISKETAYSESVKLLQKILEEDERKIRRIGVRFSKFIEAIGLDKFFDT | Dpo4 S86C, polymerase Dpo4 variant S86C |
| 22 | Protein | MIVLFVDFDYFYAQVEEVLNPSLKGKPVVVCVFSGRFEDSGAVATANYEARKFGVKA<br>GIPIVEAKKILPNAVYLPMRKEVYQQVSSRIMNLLREY<u>C</u>EKIEIASIDEAYLDISDKVRD<br>YREAYNLGLEIKNKILEKEKITVTVGISKNKVFAKIAADMAKPNGIKVIDDEEVKRLIRE<br>LDIADVPGIGNITAEKLKKLGINKLVDTLSIEFDKLKGMIGEAKAKYLISLARDEYNEPI<br>RTRVRKSIGRIVTMKRNSRNLEEIKPYLFRAIEESYYKLDKRIPKAIHVVAVTEDLDIVS<br>RGRTFPHGISKETAYSESVKLLQKILEEDERKIRRIGVRFSKFIEAIGLDKFFDT | Dpo4 S96C, polymerase Dpo4 variant S96C, |
| 23 | L-DNA | GTGGAACCGACAACTTGTGCTGCGTCCAGCATAAGAAAGGAGCTCCCTCAGAAGA<br>AGCTGCGCAGCGTGCCAGTCTGAGCTCC | MJ_1_105_LD |
| 24 | L-DNA | TCTAATACGACTCACTATAGGAGCTCAGACTGGCACGC | MJ_oligo_187_LD |
| 25 | L-DNA | GTGGAACCGACAACTTGTGC | MJ_oligo_189_LD |
| 26 | D-DNA | ATGCTGACCCTGATTCAGGGCAAAAAAATCGTGAACCATCTGCGTAGCCGTCTGG<br>CCTTTGAATATAACGGCTGATGATTAAAAATTCTGAGCAAAAACATTGTGCGGT<br>GGGCAGCCTGCGTCGTGAAGAAAAAATGCTGAACGATGTGGATCTGCTGATTATT<br>GTGCCGGAAAAAAAACTGCTGAAACATGTGCTGCCGAACATTCGTATTAAAGGCC<br>TGAGCTTTAGCGTGAAAGTGTGCGGCAACGTAAATGCTGCTGTTTATCGAATG<br>GGAAAAAAAACCTACCAGCTGGACCTGTTTACCGCGCTGGCCGAAGAAAAAACC<br>GTATGCGATCTTTCATTTTACCGGTCCGGTGAGCTATCTGATTCGTATTCGTGCGG | ASFV Pol-X ORF E. coli codon optimized |

TABLE 1 (A)-continued

SEQUENCES REFERRED TO IN THIS APPLICATION

| SEQ ID NO: | Type | Sequence | Internal Reference |
|---|---|---|---|
| | | CGCTGAAAAAAAAAAACTACAAACTGAACCAGTATGGCCTGTTTAAAAACCAGAC CCTGGTGCCGCTGAAAATTACCACCGAAAAAGAACTGATTAAAGAACTGGGCTTT ACCTATCGCATTCCGAAAAAACGCCTGTAATAA | |
| 27 | Protein | MRGSHHHHHHGMASMTGGQQMGRDLYDDDDKDRWGSMLTLIQGKKIVNHLRSRL AFEYNGQLIKILSKNIVAVGSLRREEKMLNDVDLLIIVPEKKLLKHVLPNIRIKGLSFSV KVCGERKCVLFIEWEKKTYQLDLFTALAEEEKPYAIFHFTGPVSYLIRIRAALKKKNYKL NQYGLFKNQTLVPLKITTEKELIKELGFTYRIPKKRL | His-tagged Pol-X protein sequence as encoded in pMJ14 |
| 28 | D-DNA | TCCGGTGAGCTATCTGGGTCGTATTCGTGCGGCG | QC10_up |
| 29 | D-DNA | CGCCGCACGAATACGACCCAGATAGCTCACCGGA | QC10_low |
| 30 | D-DNA | TGAGCTTTAGCGTGAAAGGGTGCGGCGAACG | QC26_up |
| 31 | D-DNA | CGTTCGCCGCACCCTTTCACGCTAAAGCTCA | QC26_low |
| 32 | D-DNA | TGAGCTTTAGCGTGAAAGCGTGCGGCGAACG | QC27_up |
| 33 | D-DNA | CGTTCGCCGCACGCTTTCACGCTAAAGCTCA | QC27_low |
| 34 | D-DNA | TGAAAGTGTGCGGCGAACGTAAAAGCGTGCTGTTTA | QC31_up |
| 35 | D-DNA | TAAACAGCACGCTTTTACGTTCGCCGCACACTTTCA | QC31_low |
| 36 | D-DNA | GATCACAGTGAGTAC | SP-1 |
| 37 | D-DNA | Phosphate-GTAAAACGACGGCCAGT | D(g1)P |
| 38 | D-DNA | ACTGGCCGTCGTTTTACAGTACTCACTGTGATC | MJ_1_140_DD |
| 39 | D-DNA | ACTGGCCGTCGTTTTACCGTACTCACTGTGATC | MJ_1_141_DD |
| 40 | D-DNA | ACTGGCCGTCGTTTTACGGTACTCACTGTGATC | MJ_1_142_DD |
| 41 | D-DNA | ACTGGCCGTCGTTTTAC→GTACTCACTGTGATC | SP1c + 18(g1) |
| 42 | D-DNA | Phosphate-ACGACGGCCAGT | D(g6)P |
| 43 | Protein | AcMLTLIQGKKIVNHLRSRLAFEYNGQLIKILSKNIVAVGSL-OGp | example 3 product (1) |
| 44 | Protein | H-RREEKLNDVDLLIIVPEKKL LKHVLPNIRIKGLSFSVKA-SMe | example 3 product (2) |
| 45 | Protein | H-CGERKCVLFIEWEKKTYQLDLFTALAEEKPYAIFHFTGPVSYLIRIRAALKKKNYKL NQYGLFKNQTLVPLKITTEKELI KELGFTYRIPKKRL-OH | example 3 product (3) |
| 46 | Protein | Ac-MLTLIQGKKIVNHLRSRLAFEYNGQLIKILSKNIVAVGSLRREEKMLNDVDLLIIVPE KKLLKHVLPNIRIKGLSFSVKA-SMe | example 4 product (4) |
| 47 | D-DNA | Atto532-GGAGCTCAGACTGGCACGC | MJ_1_33_DD |
| 48 | D-DNA | GTGGAACCGACAACTTGTGCTGCGTCCAGCATAAGAAAGGAGCTCCCTCAGAAGA AGCTGCGCAGCGTGCCAGTCTGAGCTCC | MJ_1_1_DD |
| 49 | D/L-DNA | D(GG)-L(GGAGCTCAGACTGGCACGC) | MJ_1_109_MD |
| 50 | D-DNA | ATGATTGTGCTGTTTGTGGATTTTGATTATTTTTATGCCCAGGTGGAAGAAGTTCT GAATCCGAGCCTGAAAGGTAAACCGGTTGTTGTTTGTGTTTTTAGCGGTCGCTTTG AAGATAGCGGTGCAGTTGCAACCGCCAATTATGAAGCCCGTAAATTGGTGTTAA AGCCGGTATTCCGATTGTTGAAGCCAAAAAAATTCTGCCGAATGCAGTTTATCTGC CGATGCGCAAAGAAGTTTATCAGCAGGTTAGCAGCCGTATTATGAATCTGCTGCG CGAATATAGCGAAAAAATTGAAATTGCCAGCATTGATGAAGCCTATCTGGATATT AGCGATAAAGTGCGCGATTATCGCGAAGCATATAATCTGGGCCTGGAAATTAAA ATAAAATCCTGAAAAAGAAAAAATTACCGTGACCGTGGGCATTAGCAAAAATA AAGTGTTTGCCAAAATTGCAGCAGATATGGCAAAACCGAATGGCATTAAAGTGAT TGATGATGAAGAAGTGAAACGTCTGATTCGCGAACTGGATATTGCAGATGTTCCG GGTATTGGCAATATTACCGCAGAAAAACTGAAAAAACTGGGCATTAATAAACTGG TTGATACCCTGAGCATTGAATTTGATAAACTGAAAGGCATGATTGGTGAAGCGAA AGCCAAATATCTGATTAGCCTGGCACGTGATGAATATAATGAACCGATTCGTACC CGTGTTCGTAAAAGCATTGGTCGTATTGTGACCATGAAACGCAATAGCCGTAATCT GGAAGAAATTAAACCGTACCTGTTTCGTGCAATTGAAAAGCTATTATAAACTG GATAACGCATTCCGAAAGCCATTCATGTTGTTGCAGTTACCGAAGATCTGGATAT TGTTAGCCGTGGTCGTACCTTTCCGCATGGTATTAGCAAAGAAACCGCCTATAGCG | Sso Dpo4 ORF E. coli codon optimized |

TABLE 1 (A)-continued

SEQUENCES REFERRED TO IN THIS APPLICATION

| SEQ ID NO: | Type | Sequence | Internal Reference |
|---|---|---|---|
| | | AAAGCGTTAAACTGCTGCAGAAAATCCTGGAAGAAGATGAACGTAAAATTCGTCG TATTGGTGTGCGCTTTAGCAAATTTATTGAAGCCATTGGCCTGGATAAATTTTTTG ATACC | |
| 51 | Protein | MASAWSHPQFEKSGMIVLFVDFDYFYAQVEEVLNPSLKGKPVVVCVFSGRFEDSGAV ATANYEARKFGVKAGIPIVEAKKILPNAVYLPMRKEVYQQVSSRIMNLLREYSEKIEIA SIDEAYLDISDKVRDYREAYNLGLEIKNKILEKEKITVTVGISKNKVFAKIAADMAKPN GIKVIDDEEVKRLIRELDIADVPGIGNITAEKLKKLGINKLVDTLSIEFDKLKGMIGEAKA KYLISLARDEYNEPIRTRVRKSIGRIVTMKRNSRNLEEIKPYLFRAIEESYYKLDKRIPKA IHVVAVTEDLDIVSRGRTFPHGISKETAYSESVKLLQKILEEDERKIRRIGVRFSKFIEAIG LDKFFDTGS | Strep-tagged Dpo4 protein sequence as encoded in pMJ343 |
| 52 | D-DNA | CAAAAATAAAGTGTTTGCCAAAATTGCATGCGATATGGCAAAACCG AATGGCATTAAAG | QC_28_up |
| 53 | D-DNA | CTTTAATGCCATTCGGTTTTGCCATATCGCATGCAATTTTGGCAAA CACTTTATTTTTG | QC_28_low |
| 54 | D-DNA | TGAAAAAACTGGGCATTAATAAACTGTGTGATACCCTGAGCATTGAATTTG | QC_29_up |
| 55 | D-DNA | CAAATTCAATGCTCAGGGTATCACACAGTTTATTAATGCCCAGTTTTTTCA | QC_29_low |
| 56 | D-DNA | TGAAAGGTAAACCGGTTGTTGTTTCTGTTTTTAGCGGTC | QC_30_up |
| 57 | D-DNA | GACCGCTAAAAACAGAAACAACAACCGGTTTACCTTTCA | QC_30_low |
| 58 | D-DNA | ATGCGCAAAGAAGTTTATCAGCAGGTTTGTAGCCGTATTATGAATC | QC_38_up |
| 59 | D-DNA | GATTCATAATACGGCTACAAACCTGCTGATAAACTTCTTTGCGCAT | QC_38_low |
| 60 | D-NA | AAGTTTATCAGCAGGTTAGCTGTCGTATTATGAATCTGCTGCG | QC_39_up |
| 61 | D-DNA | CGCAGCAGATTCATAATACGACAGCTAACCTGCTGATAAACTT | QC_39_low |
| 62 | D-DNA | ATTATGAATCTGCTGCGCGAATATTGTGAAAAATTGAAATTGCCAGCATT | QC_40_up |
| 63 | D-DNA | AATGCTGGCAATTTCAATTTTTTCACAATATTCGCGCAGCAGATTCATAAT | QC_40_low |
| 64 | D-DNA | Phosphate-AGCGGCTCTTCGATGATTGTGCTGTTTGTGGATTTT | MJ_1_90_DD |
| 65 | D-DNA | Phosphate-AGCGGCTCTTCGGCATGCAATTTTGGCAAACACTTT | MJ_1_91_DD |
| 66 | D-DNA | Phosphate-AGCGGCTCTTCGTGCATCACGGGAGAT | MJ_1_72_DD |
| 67 | D-DNA | Phosphate-AGCGGCTCTTCGCCCTTGAAGCTGCCACAAGGCAGGAACGTT | MJ_1_73_DD |
| 68 | Protein | MIVLFVDFDYFYAQVEEVLNPSLKGKPVVVCVFSGRFEDSGAVATANYEARKFGVKA GIPIVEAKKILPNAVYLPMRKEVYQQVSSRIMNLLREYSEKIEIASIDEAYLDISDKVRD YREAYNLGLEIKNKILEKEKITVTVGISKNKVFAKIA-thioester | Dpo4 fragment 1-154 |
| 69 | D-DNA | Phosphate-AGCGGCTCTTCGATGGGAGGGAAATCAAACGGGGAA | MJ_1_99_DD |
| 70 | D-DNA | Phosphate-AGCGGCTCTTCGGCACAAAGCTTTGAAGAGCTTGTC | MJ_1_100_DD |
| 71 | D-DNA | Phosphate-AGCGGCTCTTCGTGCGATATGGCAAAACCGAATGGCATTAAA | MJ_1_96_DD |
| 72 | D-DNA | Phosphate-AGCGGCTCTTCGCCCTTAGGTATCAAAAAATTTATCCAGG | MJ_1_97_DD |
| 73 | Protein | *C*DMAKPNGIKVIDDEEVKRLIRELDIADVPGIGNITAEKLKKLGINKLVDTLSIEFDKLK GMIGEAKAKYLISLARDEYNEPIRTRVRKSIGRIVTMKRNSRNLEEIKPYLFRAIEESYY KLDKRIPKAIHVVAVTEDLDIVSRGRTFPHGISKETAYSESVKLLQKILEEDERKIRRIGV RFSKFIEAIGLDKFFDT | Dpo4 A155C fragment 155-352 |
| 74 | D-DNA | Phosphate-AGCGGCTCTTCGTGTGATACCCTGAGCATTGAATTT | MJ_1_98_DD |
| 75 | Protein | *C*DTLSIEFDKLKGMIGEAKAKYLISLARDEYNEPIRTRVRKSIGRIVTMKRNSRNLEEIK PYLFRAIEESYYKLDKRIPKAIHVVAVTEDLDIVSRGRTFPHGISKETAYSESVKLLQKIL EEDERKIRRIGVRFSKFIEAIGLDKFFDT | Dpo4 V203C fragment 203-352 |
| 76 | D-DNA | Phosphate-AGCGGCTCTTCGATGGCAGATATGGCAAAACCGAAT | MJ_1_101_DD |
| 77 | D-DNA | Phosphate-AGCGGCTCTTCGGCACAGTTTATTAATGCCCAGTTT | MJ_1_102_DD |
| 78 | Protein | ADMAKPNGIKVIDDEEVKRLIRELDIADVPGIGNITAEKLKKLGINKL-thioester | Dpo4 fragment 155-202 |

TABLE 1 (A)-continued

SEQUENCES REFERRED TO IN THIS APPLICATION

| SEQ ID NO: | Type | Sequence | Internal Reference |
|---|---|---|---|
| 79 | D-DNA | TCTAATACGACTCACTATAGGAGCTCAGACTGGCACGC | DE4.40T7 |
| 80 | D-DNA | GTGGAACCGACAACTTGTGC | DE4.40R |
| 81 | Protein | H-RTFPHGISKETAYSESVKLLQKILEEDERKIRRIGVRFSKFIEAIGLDKFFDT-NH$_2$ | example 10 product (1) |
| 82 | Protein | Boc-VDTLSIEFDKLKGMIGEAKAKYLISLARDEYNEPIRTRVRKSIGRIVTMKRNSRNLE EIKPYLFRAIEESYYKLDKRIPKAIHVVAVTEDLDIVSRG-OH | example 10 product (2) |
| 83 | Protein | H-VDTLSIEFDKLKGMIGEAKAKYLISLARDEYNEPIRTRVRKSIGRIVTMKRNSRNLEE IKPYLFRAIEESYYKLDKRIPKAIHVVAVTEDLDIVSRGRTFPHGISKETAYSESVKLLQ KILEEDERKIRRIGVRFSKFIEAIGLDKFFDT-NH$_2$ | example 10 product (3) |
| 84 | Protein | Z-CDMAKPNGIKVIDDEEVKRLIRELDIADVPGIGNITAEKLKKLGINKL-benzyl-thioester | example 10 product (4) |
| 85 | Protein | H-RKEVYQQVSSRIMNLLREYSEKIEIASIDEAYLDISDKVRDYREAYNLGLEIKNKILE KEKITVTVGISKNKVFAKIA-SMe | example 10 product (7) |
| 86 | Protein | Ac-MIVLFVDFDYFYAQVEEVLNPSLKGKPVVVCVFSGRFEDSGAVATANYEARKFGV KAGIPIVEAKKILPNAVYLPM-OGp | example 10 product (6) |
| 87 | Protein | H-CDMAKPNGIKVIDDEEVKRLIRELDIADVPGIGNITAEKLKKLGINKLCDTLSIEFDKL KGMIGEAKAKYLISLARDEYNEPIRTRVRKSIGRIVTMKRNSRNLEEIKPYLFRAIEESY YKLDKRIPKAIHVVAVTEDLDIVSRGRTFPHGISKETAYSESVKLLQKILEEDERKIRRIG VRFSKFIEAIGLDKFFDT-OH | example 10 product (5) |
| 88 | Protein | Ac-MIVLFVDFDYFYAQVEEVLNPSLKGKPVVVCVFSGRFEDSGAVATANYEARKFGV KAGIPIVEAKKILPNAVYLPMRKEVYQQVSSRIMNLLREYSEKIEIASIDEAYLDISDKV RDYREAYNLGLEIKNKILEKEKITVTVGISKNKVFAKIA-SMe | example 10 product (8) |

It will be understood that the above is a representation of the molecules as they were used in connection with the instant invention. The attached sequence listing does only reflect the mere amino acid or nucleotide sequence thereof and not any further feature of said molecules as indicated in the above table.

The present invention is further illustrated by the figures, examples and the sequence listing from which further features, embodiments and advantages may be taken, wherein FIG. 1A shows composition of 1-gap D-DNA templates for activity test of L-polymerase X;

FIG. 1B shows composition of 6-gap D-DNA templates for activity test of L-polymerase X;

FIG. 2 A-B shows analytics of synthesized D-polypeptide product Ac-MLTLIQGKKIVNHLRSRLAFEYNGQLIKIL-SKNIVAVGSL-OGp (1) by UPLC (A) and mass spectrometry (B);

FIG. 3 A-B shows analytics of synthesized D-polypeptide product H-RREEKLNDVDLLIIV-PEKKLLKHVLPNIRIKGLSFSVKA-SMe (2) by UPLC (A) and mass spectrometry (B);

FIG. 4 A-B shows analytics of synthesized D-polypeptide product H-CGERKCVLFIEWEKKTYQLDLFTA-LAEEKPYAIFHFTGPV SYLIRIRAALKK-KNYKLNQYGLFKNQTLVPLKITTEKELI KELGFTYR-IPKKRL-OH (3) by UPLC (A) and mass spectrometry (B);

FIG. 5 A-B shows analytics of synthesized D-polypeptide product Ac-MLTLIQGKKIVNHLRSRLAFEYNGQLIKIL-SKNIVAVGSLRREEK MLNDVDLLIIV-PEKKLLKHVLPNIRIKGLSFSVKA-SMe (4) by UPLC (A) and mass spectrometry (B);

FIG. 6 A-B shows analytics of native chemical ligation D-polypeptide product Ac-MLTLIQGKKIVNHLRSR-LAFEYNGQLIKILSkNIVAVGSLRREEK MLNDVDL-LIIVPEKKLLKHVLPNIRIKGLSFSVKACGERKCVLFIE WEKKTYQLDLFTALAEEKPYAIFHFTGPVSYLIRI-RAALKKKNY KLNQYGLFKNQTLVPLKITTEKE-LIKELGFTYRIPKKRL-OH (5) by SDS-PAGE (A) and mass spectrometry (B);

FIG. 7 shows composition of 1-gap L-DNA templates for activity test of D-polymerase X;

Figure 11A:
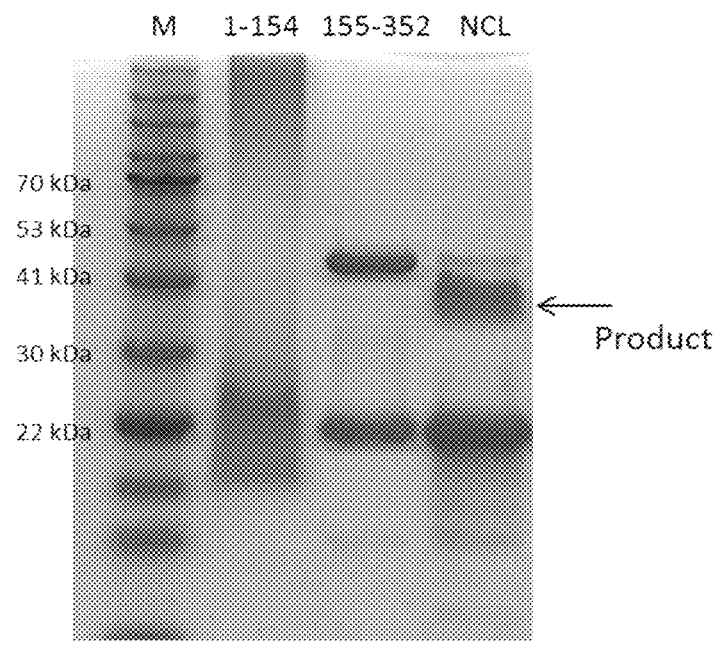
Figure 11B:
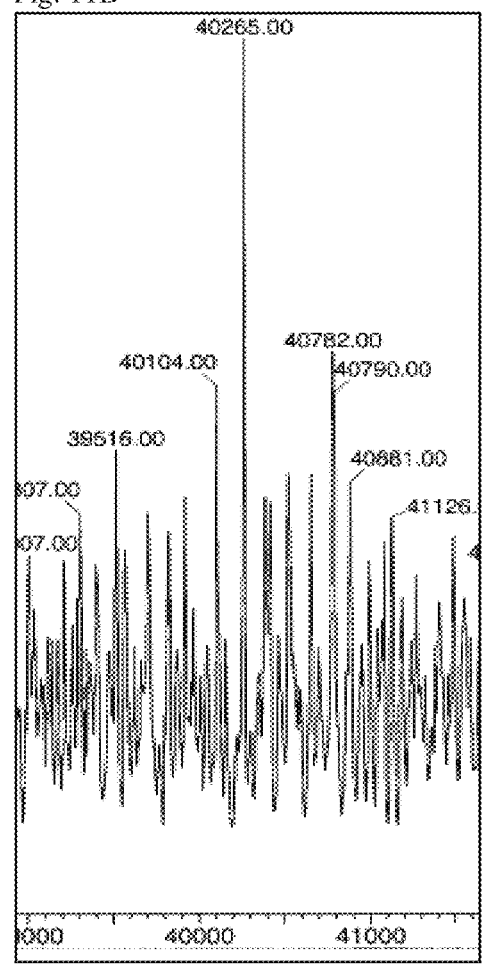
Figure 13:
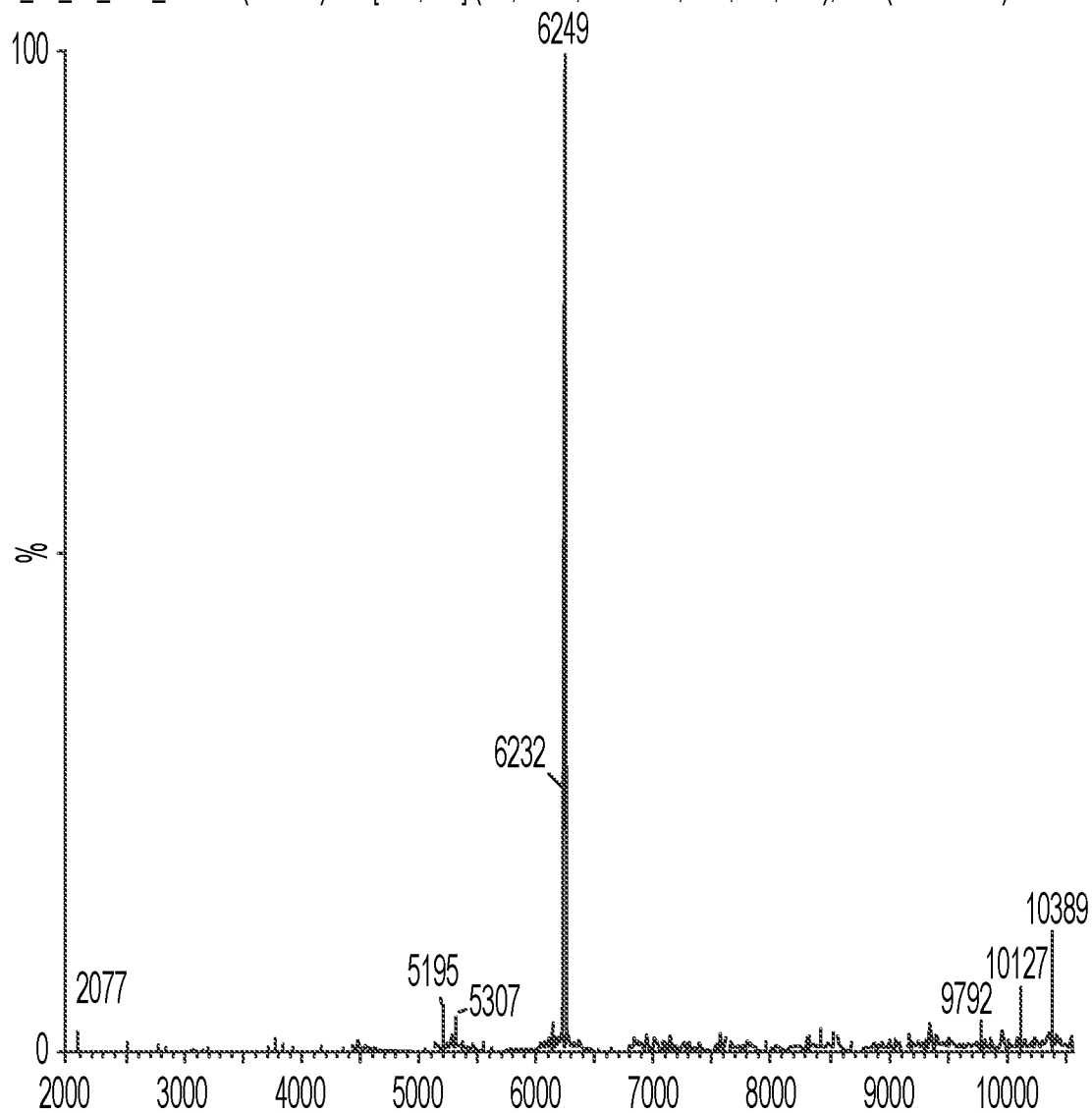
Figure 14:
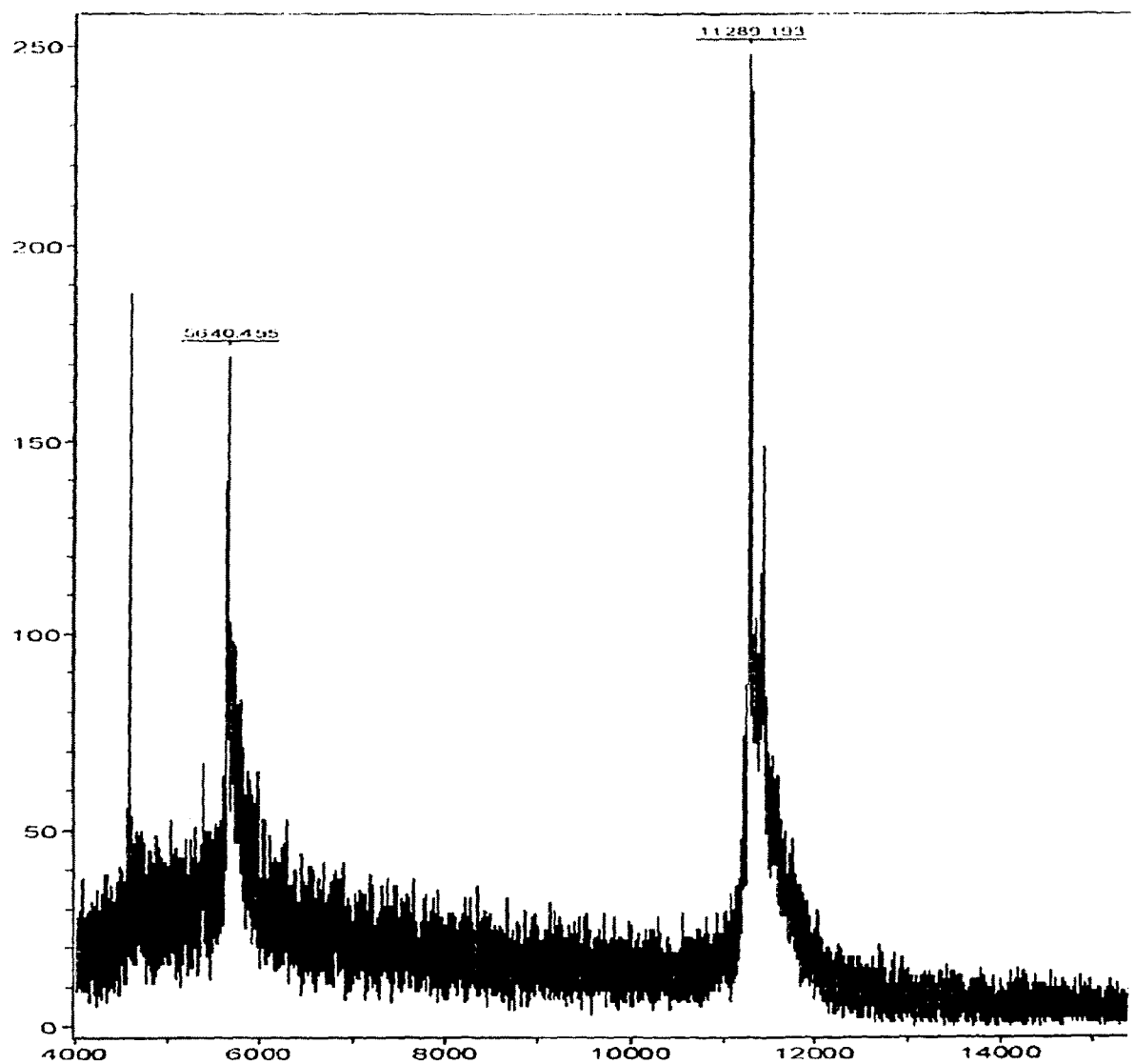
Figure 15:
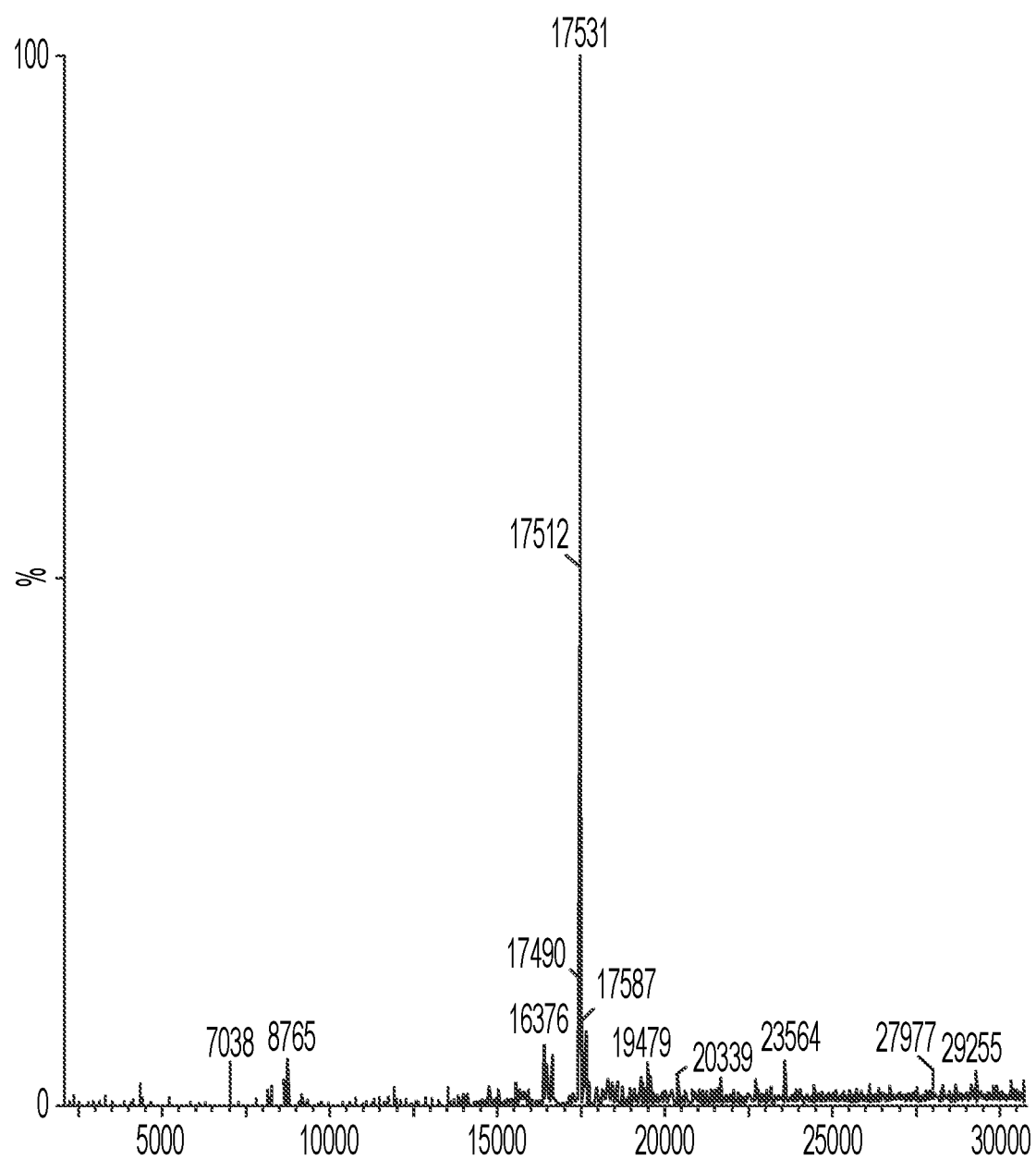
Figure 16A:
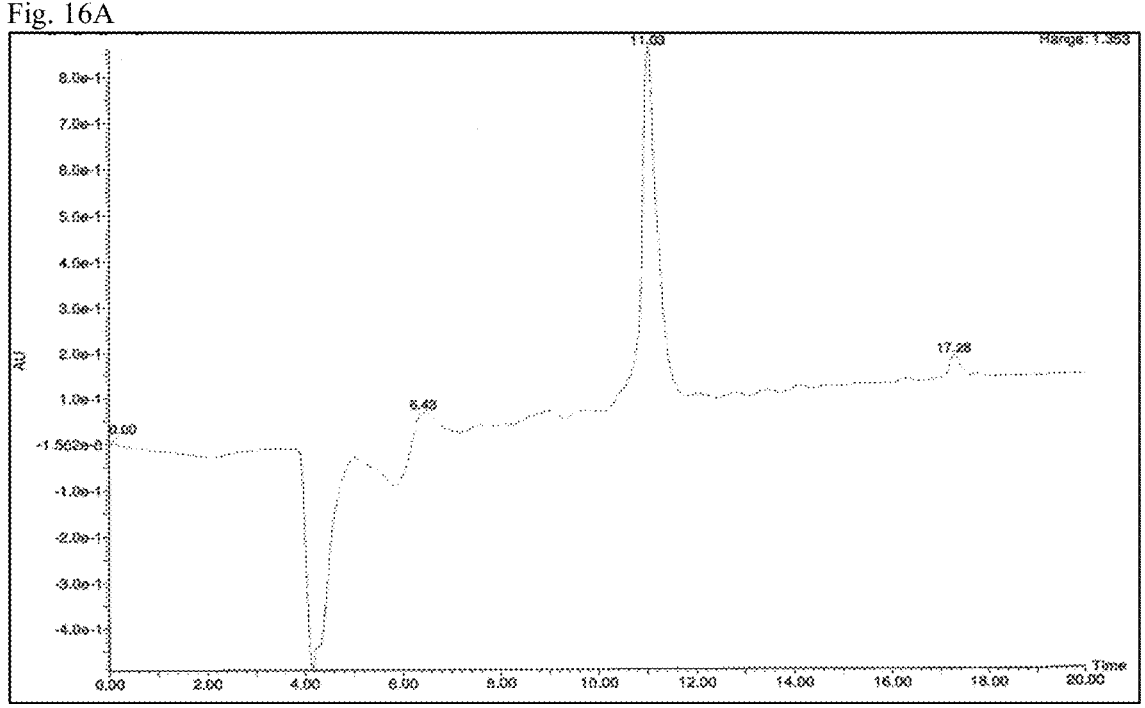
Figure 17A:
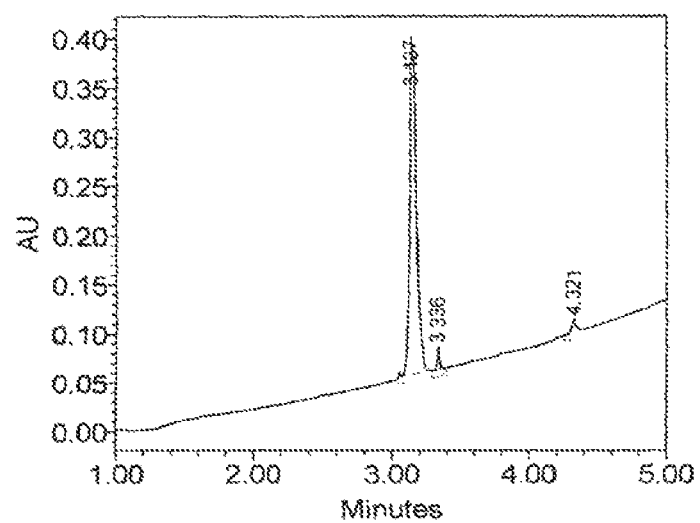
Figure 18A:
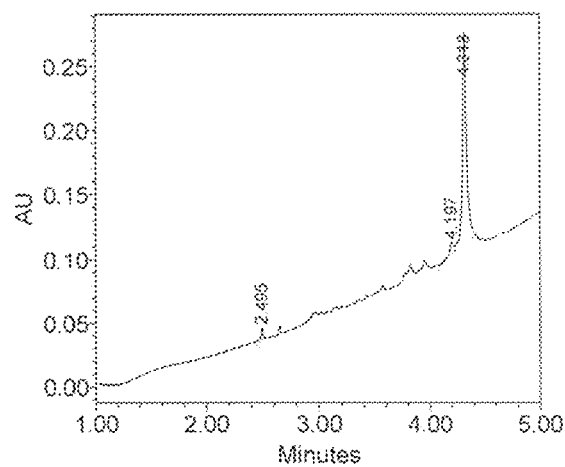
Figure 19A:
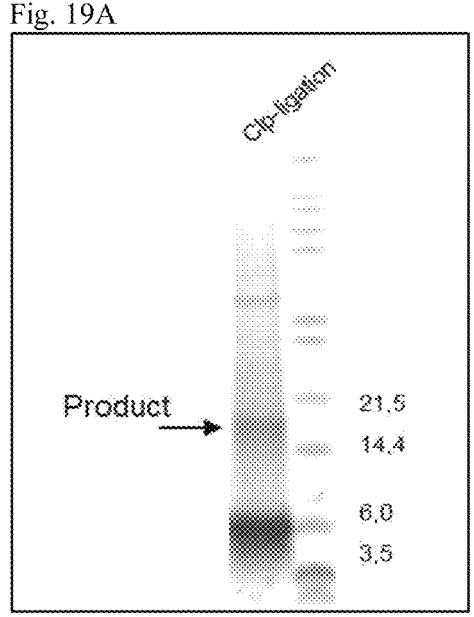
Figure 20A:
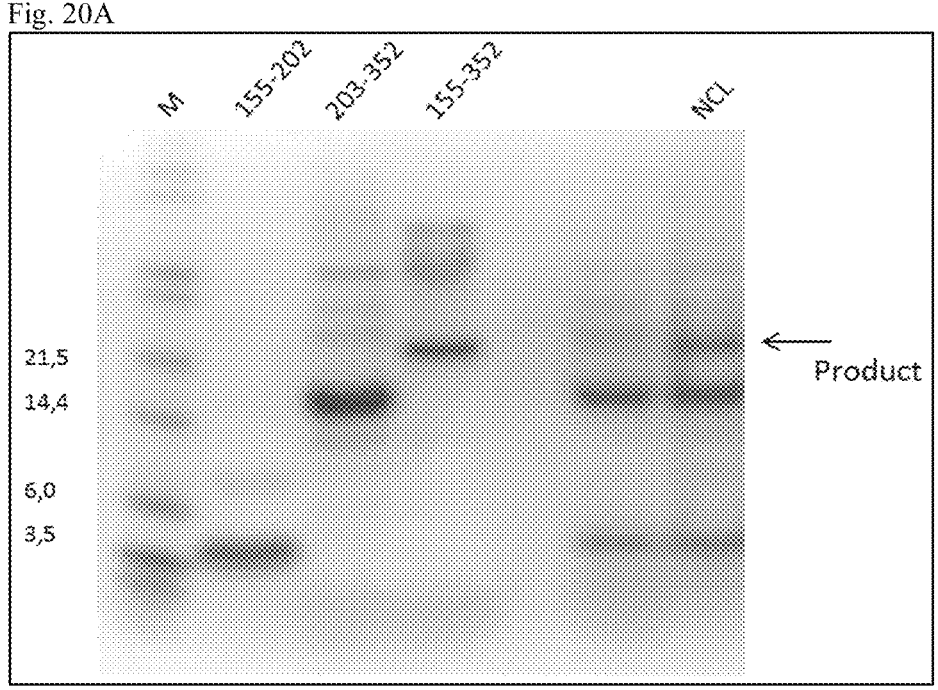
Figure 20B:
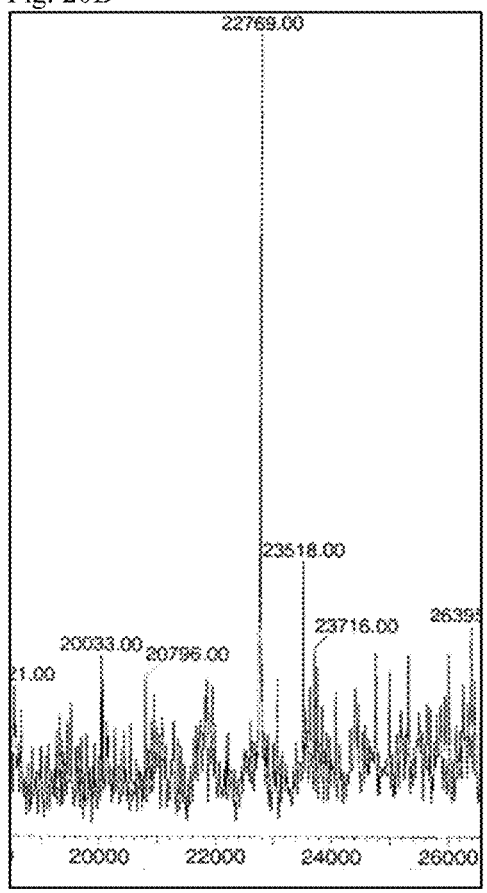

FIG. 11 A-B shows analytics of synthetic all-L-polymerase dpo4 variant A155C by SDS-PAGE (A) and LC-ESI mass spectometry (B);

FIG. 12 A shows gel electrophoresis of D-DNA PCR activity assays of L-polymerase dpo4 variants A155C, V203C, C31S and A155C/V203C FIG. 12 B shows gel electrophoresis of D-DNA PCR activity assays of recombinant and synthetic L-polymerase dpo4;

FIG. 13 shows analytics of synthesized D-polypeptide product H-RTFPHGISKETAYSESVKLLQKI-LEEDERKIRRIGVRFSKFIEAIGL DKFFDT-NH2 (1) by mass spectrometry;

FIG. 14 shows analytics of synthesized D-polypeptide product Boc-VDTLSIEFDKLKGMIGEAKAKYLIS-LARDEYNEPIRTRVRKSIGRI VTMKRNSRNLEE-IKPYLFRAIEESYYKLDKRIPKAIHVVAVTEDL DIVSRG-OH (2) by mass spectrometry;

FIG. 15 shows analytics of fragment condensation D-polypeptide product H-VDTLSIEFDKLKGMIGEAKA-KYLISLARDEYNEPIRTRVRKSIG RIVTMKRNSRN-LEEIKPYLFRAIEESYYKLDKRIPKAIHVVAVTE DLDIVSRGRTFPHGISKETAYSESVKLLQKI-LEEDERKIRRIGVRFS KFIEAIGLDKFFDT-NH$_2$ (3) by mass spectrometry;

FIG. 16 A-B shows analytics of synthesized D-polypeptide product Z-CDMAKPNGIKVIDDEEVKRLIRE-LDIADVPGIGNITAEKLKKLG INKL-benzyl-thioester (4) by RP-HPLC (A) and mass spectrometry (B);

FIG. 17 A-B shows analytics of synthesized D-polypeptide product H-RKEVYQQVSSRIMNLLREYSEKIE-IASIDEAYLDISDKVRDYREA YNL-GLEIKNKILEKEKITVTVGISKNKVFAKIA-SMe (7) by UPLC (A) and mass spectrometry (B);

FIG. 18 A-B shows analytics of synthesized D-polypeptide product Ac-MIVLFVDFDYFYAQVEEVLNPSLKGKPVVVCVFS-GRFEDSGAV ATANYEARKFGVKAGIPIVEAKKILP-NAVYLPM-OGp (6) by UPLC (A) and mass spectrometry (B);

FIG. 19 A-B shows analytics of clostripain mediated D-polypeptide ligation product Ac-MIVLFVDFDYFYAQVEEVLNPSLKGKPVVVCVFS-GRFEDSG AVATANYEARKFGVKAGIPIVEAKKILP-NAVYLPMRKEVYQQV SSRIMNLLREYSEKIEIASIDE-AYLDISDKVRDYREAYNLGLEIKN KILEKEKITVTVGISKNKVFAKIA-SMe (8) by SDS-PAGE (A) and ESI mass spectrometry (B):

FIG. 20 A-B shows analytics of native chemical ligation product of all-L-polymerase dpo4 fragment 155-352 (V203C) by SDS-PAGE (A) and LC-ESI mass spectometry (B).

EXAMPLES

Abbreviation as used in the examples.
ACN acetonitrile (Sigma-Aldrich Chemie GmbH, Schnelldorf, Deutschland)
DCM dichloromethane (Sigma-Aldrich Chemie GmbH, Schnelldorf, Deutschland)
DIPEA N,N-diisipropylamine (Sigma-Aldrich Chemie GmbH, Schnelldorf, Deutschland)
EDT (Sigma-Aldrich Chemie GmbH, Schnelldorf, Deutschland)
Fmoc 9-Fluorenyl-methoxycarbonyl-
HATU (2-(7-Aza-1H-benzotriazole-1-yl)-1,1,3,3-tetramethyluronium hexafluorophosphate) (CreoSalus, Louisville Ky., USA)
HFIP 1,1,1,3,3,3-hexafluorophosphate (Sigma-Aldrich Chemie GmbH, Schnelldorf, Deutschland)
HPLC High-performance liquid chromatography (sometimes referred to as high-pressure liquid chromatography)
MeIm methyl imidazole (Sigma-Aldrich Chemie GmbH, Schnelldorf, Deutschland)
MeOH methanol (Sigma-Aldrich Chemie GmbH, Schnelldorf, Deutschland)
MSNT 1-(Mesitylene-2-sulfonyl)-3-nitro-1,2,4-triazole (Merck KGaA, Darmstadt, Germany)
NMP N-methyl-pyrrolidone (Iris Biotech GmbH, Marktredwitz, Deutschland)
PyBOP (Benzotriazol-1-yloxy)tripyrrolidinophosphoniumhexafluorophosphat (MERCK KGAA, DARMSTADT, GERMANY)
SDS Sodium dodecyl sulfate (Sigma-Aldrich Chemie GmbH, Schnelldorf, Deutschland)
TBTU O-(Benzotriazol-1-yl)-N,N,N',N'-tetramethyluroniumtetrafluoroborat (Merck KGaA, Darmstadt, Germany)
tBu (tert.-Butyl-)
TFA trifluoroacetic acid (Sigma-Aldrich Chemie GmbH, Schnelldorf, Deutschland)
TFE 1,1,1-trifluoroethanol (Sigma-Aldrich Chemie GmbH, Schnelldorf, Deutschland)
THF (Sigma-Aldrich Chemie GmbH, Schnelldorf, Deutschland)
TIS (Sigma-Aldrich Chemie GmbH, Schnelldorf, Deutschland)
TLC Thin layer chromatography
Tris Tris(hydroxymethyl)aminomethane (Sigma-Aldrich Chemie GmbH, Schnelldorf, Deutschland)
UPLC Ultra-performance liquid chromatography Example 1—Recombinant Expression and Purification of Wild-Type and Variants of Polymerase X Polymerase X from African swine fever virus (abbr. ASFV) was described and characterized by Oliveros et al in 1997. The wild-type gene of the polymerase X has an open reading frame (abbr. ORF) of only 525 base pairs including start codon and stop codon (Oliveros et al, 1997). The encoded protein has a length of only 174 amino acids. This example describes how polymerase X as well as variants thereof have been expressed in *E. coli* and been purified using a His$_6$-Tag.

1.1 Expression Constructs

Since the codon usage of ASFV differs from *E. coli*, an *E. coli*-codon-optimized synthetic gene for polymerase X was purchased from GeneArt AG (Regensburg, Germany). The synthetic gene sequence was provided in pCR4-Blunt-TOPO vector (originator company: Invitrogen, Karlsruhe, Germany). The codon-optimized open reading frame including start codon and two stop codons had the following sequence:

```
ATGCTGACCCTGATTCAGGGCAAAAAAATCGTGAACCATCTGCGTAGCCG
TCTGGCCTTTGAATATAACGGCCAGCTGATTAAAATTCTGAGCAAAAACA
TTGTGGCGGTGGGCAGCCTGCGTCGTGAAGAAAAATGCTGAACGATGTG
GATCTGCTGATTATTGTGCCGGAAAAAAAACTGCTGAAACATGTGCTGCC
GAACATTCGTATTAAAGGCCTGAGCTTTAGCGTGAAAGTGTGCGGCGAAC
GTAAATGCGTGCTGTTTATCGAATGGGAAAAAAAAACCTACCAGCTGGAC
CTGTTTACCGCGCTGGCCGAAGAAAAACCGTATGCGATCTTTCATTTTAC
CGGTCCGGTGAGCTATCTGATTCGTATTCGTGCGGCGCTGAAAAAAAAAA
ACTACAAACTGAACCAGTATGGCCTGTTTAAAAACCAGACCCTGGTGCCG
CTGAAAATTACCACCGAAAAAGAACTGATTAAAGAACTGGGCTTTACCTA
TCGCATTCCGAAAAAACGCCTGTAATAA.
```

In order to obtain an expression construct for polymerase X, also referred to as all-L polymerase X, the gene of the polymerase X was cut out from pCR4-Blunt-TOPO with BamHI and PstI and subcloned in pRSET-A vector (Invitrogen, Karlsruhe, Germany). Subcloning added a His$_6$-Tag to the N-terminus, and brought the gene under control of the T7 promoter. The construct was named pMJ14 and was used for expression of all-L polymerase X in *E. coli*. The protein polymerase X expressed from pMJ14 had the following sequence of 210 amino acids:

MRGSHHHHHHGMASMTGGQQMGRDLYDDDDKDRWGSMLTLIQGKKIVNHL

RSRLAFEYNGQLIKILSKNIVAVGSLRREEKMLNDVDLLIIVPEKKLLKH

VLPNIRIKGLSFSVKVCGERKCVLFIEWEKKTYQLDLFTALAEEKPYAIF

HFTGPVSYLIRIRAALKKKNYKLNQYGLFKNQTLVPLKITTEKELIKELG

FTYRIPKKRL.

The initial 36 amino acids represented the His$_6$-Tag including a few spacer amino acids and some other sequence tags (T7 Gene 10 leader, Anti-Express Epitope). The final 174 amino acid part was identical to the polymerase X protein sequence as found in ASFV.

Expression constructs for variants of all-L polymerase X were made using the commercially available QuikChange kit (Stratagene GmbH, Waldbronn, Germany) according to manufacturer's protocol. Plasmid pMJ14 served as template. Oligonucleotides needed for QuikChange were either synthesized at the NOXXON facility (QC10_up, QC10_low) or purchased from Purimex (Grebenstein, Germany) (QC26_up, QC26_low, QC27_up, QC27_low, QC31_up, QC31_low). The following variant expression constructs were made and used for expression of the variants of the all-L polymerase in *E. coli*:

| variant | expression construct | oligonucleotides used for QuikChange mutagenesis procedure |
|---|---|---|
| I124G | pMJ130 | QC10_up (5'-TCCGGTGAGCTATCTGGGTCGTATTCGTGCGGCG-3') QC10_low (5'-CGCCGCACGAATACGACCCAGATAGCTCACCGGA-3') |
| V80G | pMJ356 | QC26_up (5'-TGAGCTTTAGCGTGAAAGGGTGCGGCGAACG-3') QC26_low (5'-CGTTCGCCGCACCCTTTCACGCTAAAGCTCA-3') |
| V80A | pMJ357 | QC27_up (5'-TGAGCTTTAGCGTGAAAGCGTGCGGCGAACG-3') QC27_low (5'-CGTTCGCCGCACGCTTTCACGCTAAAGCTCA-3') |
| C86S | pMJ412 | QC31_up (5'-TGAAAGTGTGCGGCGAACGTAAAAGCGTGCTGTTTA-3') QC31_low (5'-TAAACAGCACGCTTTTACGTTCGCCGCACACTTTCA-3') |

1.2 Protein Expression in *E. coli*

All-L-polymerase X was expressed in *E. coli* using expression construct pMJ14. Variants of the all-L-polymerase X were expressed from pMJ130, pMJ356, pMJ357 or pMJ412. For expression, the appropriate expression construct was transformed in competent *E. coli* strain 'BL-21 (DE3) pLysS' (Novagen/VWR, Dresden, Germany) and maintained with the antibiotic Ampicillin. The culture was grown at 37° C. in 2YT medium until the optical density at 600 nm reached approx. 0.6. Then protein expression was induced by adding Isopropyl beta-D-1-thiogalactopyranoside (abbr. IPTG) to a final concentration of 0.4 mM. Expression was performed for 4 hours at 30° C. Cells were harvested by centrifugation and either stored at −80° C. or immediately processed.

1.3 Protein Purification

Fresh or frozen *E. coli* cells were resuspended on ice in 'lyse and bind buffer' (50 mM Na-Phosphate, pH 7.5, 500 mM NaCl, 40 mM Imidazole) and lysed using a 'French Press' (G. Heinemann, Schwäbisch Gmünd, Germany) cell disrupter. Purification was done at 4° C. using 'Ni-NTA Superflow' material (Qiagen, Hilden, Germany). Step elution was done with elution buffer (50 mM Na-Phosphate, pH 7.5, 500 mM NaCl, 200 mM Imidazole). Fractions were analyzed using SDS-PAGE (Invitrogen, Karlsruhe, Germany), pooled and, if required, further purified with anion-ion-exchange chromatography on an 'ÄKTA purifier' system using 'Q Sepharose fast flow' material (GE healthcare, Freiburg, Germany). Protein identity was confirmed by MALDI mass spectometry and correct fractions were pooled, concentrated and re-buffered. Purified protein was stored at −20° C. in a buffer consisting of 25 mM Na-Phosphate, pH 7.5, 250 mM NaCl, 50% glycerol. Protein concentrations were estimated by BCA-protein assay (Pierce/Perbio Science, Bonn, Germany) using a bovine serum albumin (abbr. BSA) standard.

Example 2—Activity Confirmation of Polymerase X and Variants of Polymerase X

The activity assays for the all-L-polymerase X and variants of all-L-polymerase X (see Example 1) were done with different types of substrate complexes formed by oligonucleotides, wherein the substrates and oligonucleotides consists of D-DNA-nucleotides.

2.1 Activity Assays on Substrates with 1-Nucleotide Gap

List of oligonucleotides for the 1-gap substrates:

| Name | Length, nt | Sequence (5'→3') |
|---|---|---|
| SP-1 | 15 | GATCACAGTGAGTAC |
| D(g1)P | 17 | Phosphate-GTAAAACGACGGCCAGT |
| MJ_1_140_DD | 33 | ACTGGCCGTCGTTTTACAGTACTCACTGTGATC |

-continued

| Name | Length, nt | Sequence (5'→3') |
|---|---|---|
| MJ_1_141_DD | 33 | ACTGGCCGTCGTTTTACCGTACTCACTGTGATC |
| MJ_1_142_DD | 33 | ACTGGCCGTCGTTTTACGGTACTCACTGTGATC |
| SP1c + 18(g1) | 33 | ACTGGCCGTCGTTTTACTGTACTCACTGTGATC |

Substrate complexes were made by annealing a template strand of a DNA oligonucleotide consisting of 33 nucleotides (also referred to as lower strand) with two different DNA oligonucleotides consisting of 15 and 17 nucleotides, respectively, which hybridized to the template strand at its 5'-end and 3'end, respectively, resulting in a gap of one nucleotide in the upper strand. The complexes contained either A, C, G or T at the template position within the gap. Before annealing, oligonucleotide SP-1 consisting of 15 nucleotides was radioactively labeled at its 5'-end with $^{32}$P by a standard kinase reaction employing Gamma-$^{32}$P-Adenosine-Triphosphate (ATP) and T4 polynucleotide kinase. Annealing was done in 10 mM Tris-HCl, 5 mM MgCl$_2$, pH 8.0 by heating 10 min at 65° C. and slowly cooling down. Unincorporated gamma-$^{32}$P-ATP was removed by purification over NAP-columns (GE healthcare).

In the activity assay, all-L-polymerase X and the variants thereof were combined with D-configurated 1-gap substrate complexes (see FIG. 1A). As a negative control, each substrate was also incubated without all-L-polymerase X and variants thereof and D-desoxy-nucleotide-triphosphates (dNTP's). Depending on the template base within the 1-gap complex only the corresponding D-dNTP was added during the assay. A typical 6 µl assay contained 50 nM substrate complex, 1.7 ng/µl L-all-L-polymerase X or variants thereof, 8 µM of one D-dNTP and buffer (50 mM Tris-HCl, 10 mM MgCl$_2$, 4% glycerol, 0.1 mg/ml bovine serum albumin (BSA), pH 7.5). D-dNTP's were purchased from Rovalab (Teltow, Germany). The incubation time was 30 minutes at 37° C. The whole assay volume was mixed with sample buffer/dye, loaded on a denaturing sequencing gel a separated for 4 hours. The gel was exposed to Kodak K screen overnight at −80° C. and read out using BioRad Fx phosphoimager system.

All-L-polymerase X and the variants I124G, V80A and V80G were active under these conditions and filled the 1 nucleotide gap between the two upper strand DNA oligonucleotides.

2.2 Activity Assay on a Substrate with 6-Nucleotide Gap
List of oligonucleotides for the 6-gap substrate:

| Name | Length, nt | Sequence (5'→3') |
|---|---|---|
| SP-1 | 15 | GATCACAGTGAGTAC |
| D(g6)P | 12 | Phosphate-ACGACGGCCAGT |
| SP1c + 18(g6) | 33 | ACTGGCCGTCGTTCTATTGTACTCACTGTGATC |

Substrate complexes were made by annealing a template strand of a DNA oligonucleotide consisting of 33 nucleotides (referred to as lower strand) with two different DNA oligonucleotides consisting of 15 and 12 nucleotides, respectively, which hybridized to the template strand at its 5'-end and 3'end, respectively, resulting in a gap of six nucleotides in the upper strand. Before annealing, oligonucleotide SP-1 consisting of 15 nucleotides was radioactively labeled at its 5'-end with $^{32}$P by a standard kinase reaction employing Gamma-$^{32}$P-Adenosine-Triphosphate (ATP) and T4 polynucleotide kinase. Annealing was done in 10 mM Tris-HCl, 5 mM MgCl$_2$, pH 8.0 by heating 10 min at 65° C. and slowly cooling down. Unincorporated gamma-$^{32}$P-ATP was removed by purification over NAP-columns (GE healthcare, Freiburg, Germany).

In the activity assay, all-L-polymerase X and variants thereof were combined with D-configurated 6-gap substrate complex (FIG. 1B). As a negative control, the substrate was also incubated without all-L-polymerase X or variants thereof and desoxy-nucleotide-triphosphates (D-dNTP's). A typical 6 µl assay contained 50 nM substrate complex, up to 1.3 ng/µl all-L-polymerase X or variants thereof, 8 µM each of the D-dNTP's and buffer (50 mM Tris-HCl, 10 mM MgCl2, 4% glycerol, 0.1 mg/ml bovine serum albumin (BSA), pH 7.5). D-dNTP's were purchased from Rovalab (Teltow, Germany) A typical incubation time was 30 minutes at 37° C. The whole assay volume was mixed with sample buffer/dye, loaded on a denaturing sequencing gel a separated for 4 hours. The gel was exposed to Kodak K screen overnight at −80° C. and read out using BioRad Fx phosphoimager system.

All-L-polymerase X and the variants (except C86S) were active under these conditions and filled the 6 nucleotide gap between the two upper strand DNA oligonucleotides.

Example 3—Synthesis of a Variant of Polymerase Pol X Consisting of D-Amino Acids Within the example the synthesis of the all-D polymerase X variant V80A is described. The amino acid sequence of the all-D polymerase X variant V80A is Ac-

MLTLIQGKKIVNHLRSRLAFEYNGQLIKILSKNIVAVGSLRREEKMLNDV

DLLIIVPEKKLLKHVLPNIRIKGLSFSVKACGERKCVLFIEWEKKTYQLD

LFTALAEEKPYAIFHFTGPVSYLIRIRAALKKKNYKLNQYGLFKNQTLVP

LKITTEKELIKELGFTYRIPKKRL-OH.

All amino acids used are protected according to the Solid-phase peptide synthesis Fmoc/tBu-strategy requirements (Eric Atherton et al., 1981). All amino acids used are D-amino acids (Bachem, Bubendorf, Switzerland).

3.1 Synthesis of HO-Gp(Boc)$_2$

The tert-butyloxycarbonyl-protected 4-guanidinophenol was synthesized in analogy to Sekizaki et al. (Sekizaki et al., 1996). According to this 40 mmole N,N'-Bis-(tert-butyloxycarbonyl)-S-methylisothiourea (Sigma-Aldrich Chemie GmbH, Schnelldorf, Deutschland) and 60 mmole 4-aminophenol (Sigma-Aldrich Chemie GmbH, Schnelldorf, Deutschland) were dissolved in 250 ml THF in a 500 ml bottom round flask. Following this the solution was argon flushed for 10 min and kept stirring for 120 hours while sealed with a CaCl$_2$ tube.

After evaporating the solvent the residue was precipitated with ice cold methanol. The precipitate was dried under vacuum over P$_4$O$_{10}$. Finally the product was purified using flash chromatography with DCM. Product containing fractions were combined and the solvent was evaporated under reduced pressure. TLC, reversed phase HPLC, mass spectrometry and NMR were used for analytics. The experimentally determined mass corresponds to the calculated mass of 351 Da.

3.2 Synthesis of H-D-Leu-OGp(Boc)$_2$ 1 mmole Z-D-Leu-OH (Bachem, Bubendorf, Switzerland), 0.9 eq. TBTU and 0.9 eq. HO-Gp(Boc)$_2$ were dissolved in 10 ml DMF. After addition of 2 eq. DIPEA the solution was stirred for 2 hours. After evaporating the solvent the raw product was purified with flash chromatography using DCM. Pure fractions of Z-D-Leu-OGp(Boc)$_2$ were combined and the solvent was evaporated.

Z-D-Leu-OGp(Boc)$_2$ was dissolved in 10 ml MeOH and flushed with argon. Hydrolytic cleavage of the N-terminal Z-group was achieved by the addition of Pd/C catalyst and H$_2$ in 2 hours. After filtrating off H-D-Leu-OGp(Boc)$_2$ MeOH was evaporated under reduced pressure. Analytics was performed using reversed phase HPLC and mass spectrometry. The correct mass of 465 Da for the procduct was found and is in correspondence the calculated mass.

3.3 Synthesis of all-D-Peptide AcMLTLIQGK-KIVNHLRSRLAFEYNGQLIKILSKNIVAVGSL-OGp (1)

0.10 mmole TentaGel-R-Trityl resin (Rapp Polymere, Tübingen, Deutschland) was loaded with Fmoc-D-Ser(tBu)-OH (Bachem, Bubendorf, Switzerland) as described by Barlos et al. (Barlos et al., 1989). Therefore 0.10 mmol resin was incubated twice for 30 min with 0.6 mmole thionylchloride and subsequently washed with DCM. Following this the resin was incubated 90 min with 0.6 mmole Fmoc-D-Ser(tBu)-OH, 2.4 mmol DIPEA in 6 ml DCM. Afterwards the resin was blocked three times for 10 min using a solution of 10% MeOH (v/v), 10% DIPEA (v/v) in DCM and washed with DCM. Automated synthesis was done using an ABI 433 (Applied Biosystems, Foster City, USA) with the FASTmoc protocol. 10 eq. amino acid were activated using 9 eq. HATU and 20 eq. DIPEA in NMP. Coupling time was 45 min and Fmoc-deprotection was performed three times for 7 min with 20% (v/v) piperidine (Sigma-Aldrich Chemie GmbH, Schnelldorf, Deutschland) in NMP.

The cleavage of the fully protected peptide acid was achieved by incubating the peptidyl resin twice in 10 ml 30% (v/v) HFIP in DCM for 2 hours. After filtering off the peptide the solvent was evaporated and the residue precipitated using ice cold diethyl ether. The precipitated peptide was isolated and dried.

0.01 mmole fully protected peptide, 4 eq. PyBOP and 5 eq. H-D-Leu-OGp(Boc)$_2$ were dissolved in 6 ml NMP. After addition of 10 eq. DIPEA the mixture was stirred for 4 hours. Following this the solvent was reduced evaporated and the residue precipitated by ice cold diethyl ether. The precipitated peptide ester was dried and subsequently protection groups were cleaved off using 2.5% EDT, 2.5% water, 2.5% TIS in TFA for 2 hours. Following the evaporation of TFA the peptide was precipitated with ice cold diethyl ether. Reversed phase HPLC purification of the peptide ester was performed on a C18 column (Phenomenex, Aschaffenburg, Germany) using an ACN/water gradient. Fractions that contain product were combined and freeze dried.

Figure 2A:
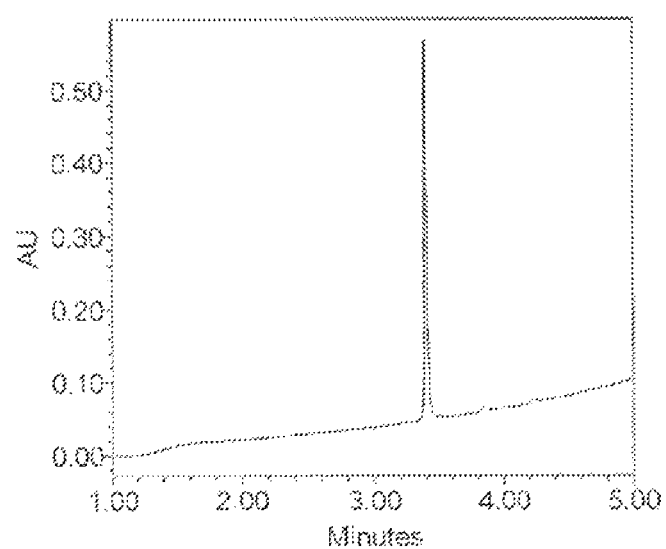
Figure 2B:
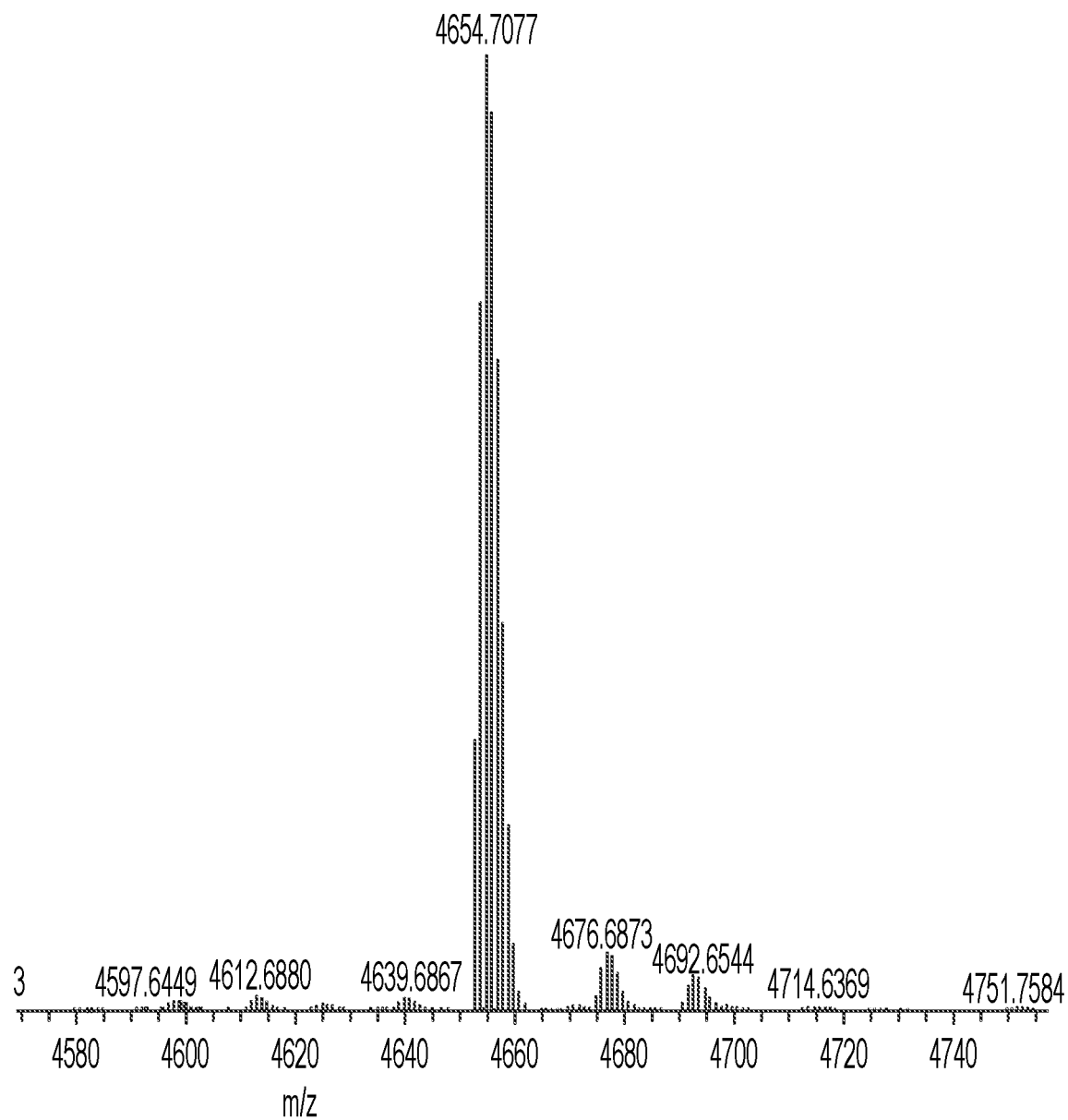

The final product was characterised by HPLC/UPLC (FIG. 2A) and mass spectrometry (FIG. 2B). The measured mass for the product of 4654.7 Da is in correspondence to the theoretical mass of 4652.7 Da.

3.4 Synthesis of all-D-Peptide H-RREEKLNDVDLLIIV-PEKKL LKHVLPNIRIKGLSFSVKA-SMe (2)

0.10 mmole TentaGel-R—NH$_2$ resin (Rapp Polymere, Tübingen, Deutschland) was loaded with Fmoc-D-Ala-OH using 5 eq. amino acid, eq. 4.9 eq. HATU and 10 eq. DIPEA for 45 min in 6 ml NMP. Subsequently the resin was washed with THF. Conversion to Fmoc-d-Ala-Ψ[CS—NH]—R-TentaGel was achieved by incubation with 4 eq. Lawesson reagent in THF at 80° C. for 2 hours. Following this the resin was washed with NMP. Subsequently the so prepared resin was used in automated peptide synthesis as described previously (see Example 1.3). Following this the corresponding thioester was generated by incubation with methyl iodide in DMF overnight according to Sharma et al. (Sharma et al., 2011). After filtering of the resin the peptide thioester containing solvent was evaporated and the residue precipitated using ice cold diethyl ether. The cleavage of side chain protection groups was performed with 2.5% EDT, 2.5% water, 2.5% TIS in TFA for 2 hours. Following the evaporation of TFA the peptide was precipitated with ice cold diethyl ether. Reversed phase HPLC purification of the peptide thioester was performed on a C18 column (Phenomenex, Aschaffenburg, Germany) using an ACN/water gradient. Fractions that contain product were combined and freeze dried.

Figure 3A:
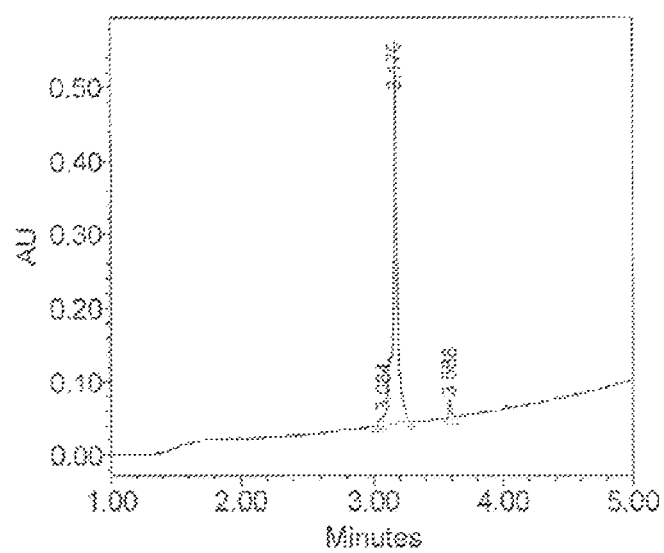
Figure 3B:
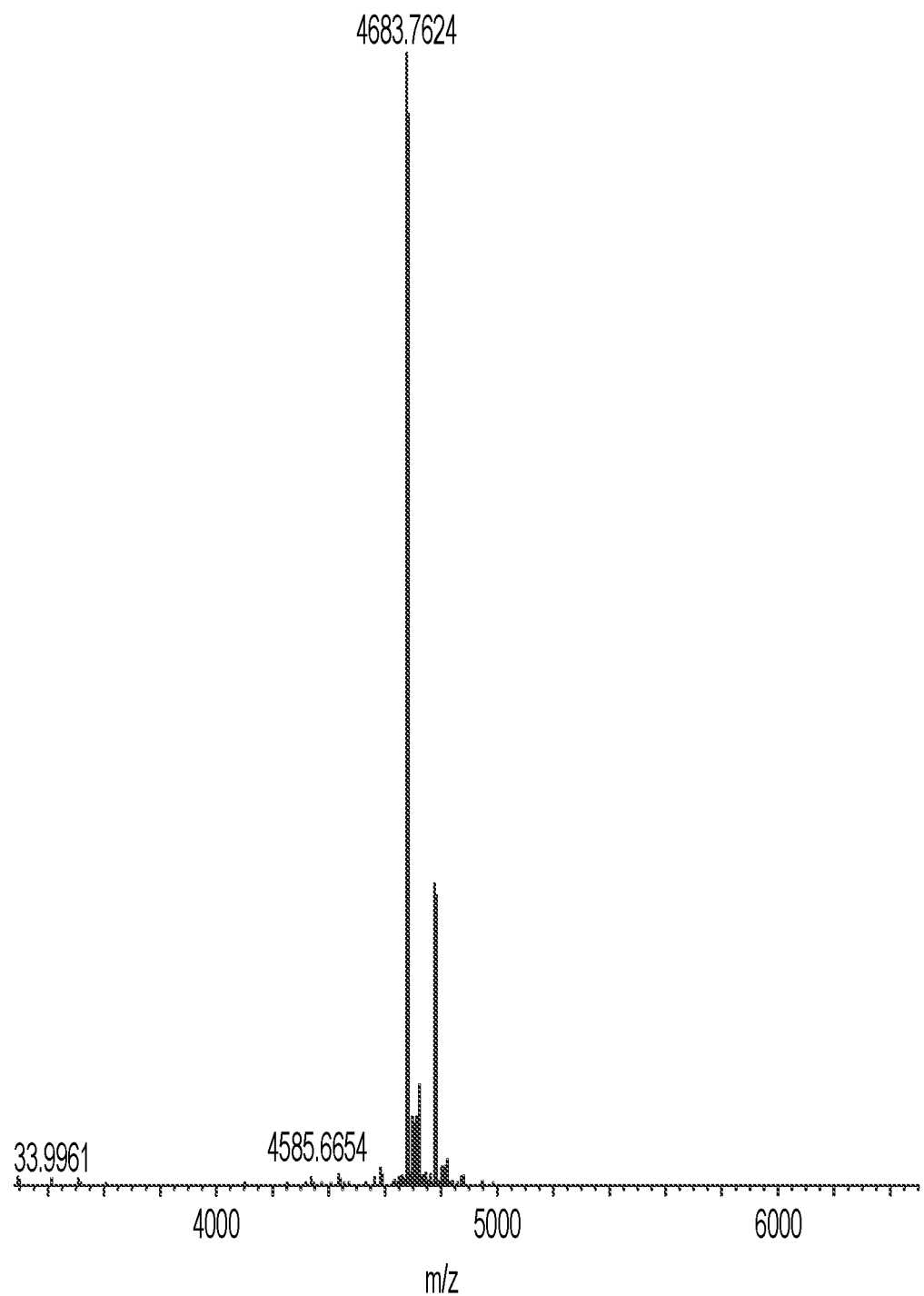

The final product was characterised by HPLC/UPLC (FIG. 3A) and mass spectrometry (FIG. 3B). The experimentally determined mass for the product (4683.8 Da) is in accordance with the theoretical value of 4681.7 Da

3.5 Synthesis of all-D-Peptide H-CGERKCVLFIEWEKKTYQLDLFTA-LAEEKPYAIFHFTGPVSYLIRIRAALKKKNYKL NQYGLFKNQTLVPLKITTEKELIKELGFTYRIPKKRL-OH (3)

0.10 mmole TentaGel-R-PHB resin (Rapp Polymere, Tübingen, Deutschland) was loaded with Fmoc-D-Leu-OH using 6 eq. amino acid, 6 eq. MSNT and 4.5 eq MeIm in DCM. Automated synthesis was done using an ABI 433 with the FASTmoc protocol. 10 eq. amino acid were activated using 9 eq. HATU and 20 eq. DIPEA in NMP. Coupling time was 45 min and Fmoc-deprotection was performed three times for 7 min with 20% (v/v) piperidine in NMP. Double coupling steps were performed after 42 amino acids. Cleavage of the N-terminal Fmoc-protected peptide was achieved using 2.5% EDT, 2.5% water, 2.5% TIS in TFA for 2 hours. Following the evaporation of TFA the peptide was precipitated with ice cold diethyl ether. Reversed phase HPLC purification of the crude N-terminal protected peptide was performed on a C18 column using an ACN/water gradient. Product containing fractions were combined and freeze dried. The Fmoc-protected peptide was subsequently dissolved and stirred in 20% piperine in DMF for cleaving off the N-terminal Fmoc-group. After 20 min the solvent was evaporated and the residue precipitated using ice cold diethyl ether. Subsequently the precipitated crude peptide was purified using reversed phase HPLC with C18 column with an ACN/water gradient. Product containing fractions were combined and freeze dried.

Figure 4B:
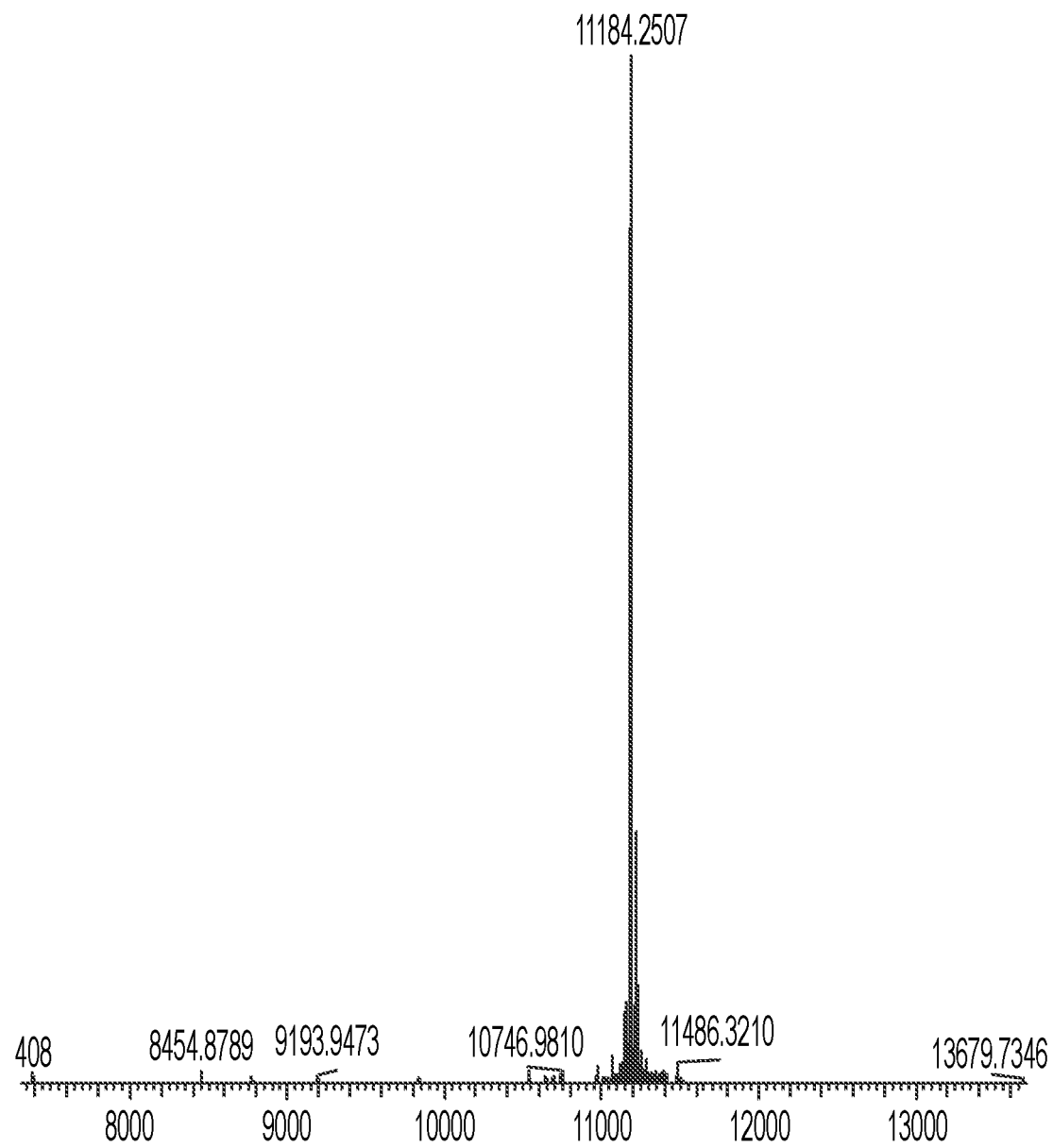

The final product was characterised by HPLC/UPLC (FIG. 4A) and mass spectrometry (FIG. 4B). The determined mass of the product (11184.3 Da) corresponds to the theoretical mass of 11178.2 Da.

3.6 Synthesis of all-D-Peptide Ac-MLTLIQGK-KIVNHLRSRLAFEYNGQLIKILSKNIVAVGSLR-REEKMLNDVDLLIIVP EKKLLKHVLPNIRIKGLSFSVKA-SMe (4) by Protease-Catalyzed Ligation of Peptide 1 with Peptide 2

Peptide 1 was solved 0.2 mM and peptide 2 was solved 0.6 mM in sodium-phosphate buffer (100 mM, pH 8.5, with 100 mM NaCl) containing 2% Triton X100 (Sigma Aldrich Chemie GmbH, Schnelldorf, Germany). After addition of 20 µM Clostripain (Endoprotease Arg-C, Worthington Biochemical Corporation, Lakewood, N.J., USA) the reaction mixture was shaken overnight at 37° C. The precipitated peptides were centrifuged, solved in H$_2$O/ACN/Formic Acid 60/40/0.5 and purified by reversed-phase HPLC using a RP-18-column (Phenomenex, Aschaffenburg, Germany) with a gradient of ACN in water of 30% to 60% within 30 min. Product containing fractions were combined and freeze dried.

Figure 5A:
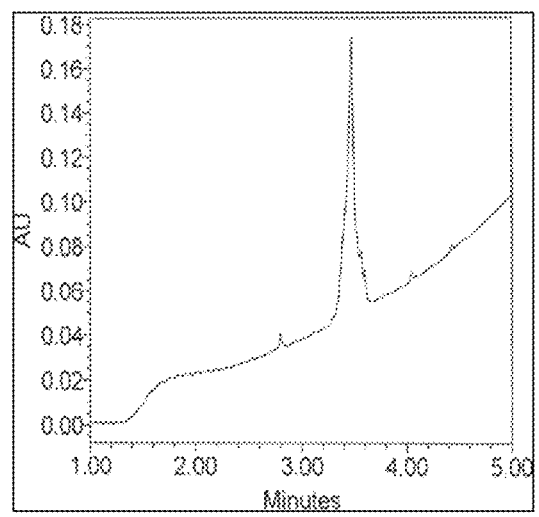
Figure 5B:
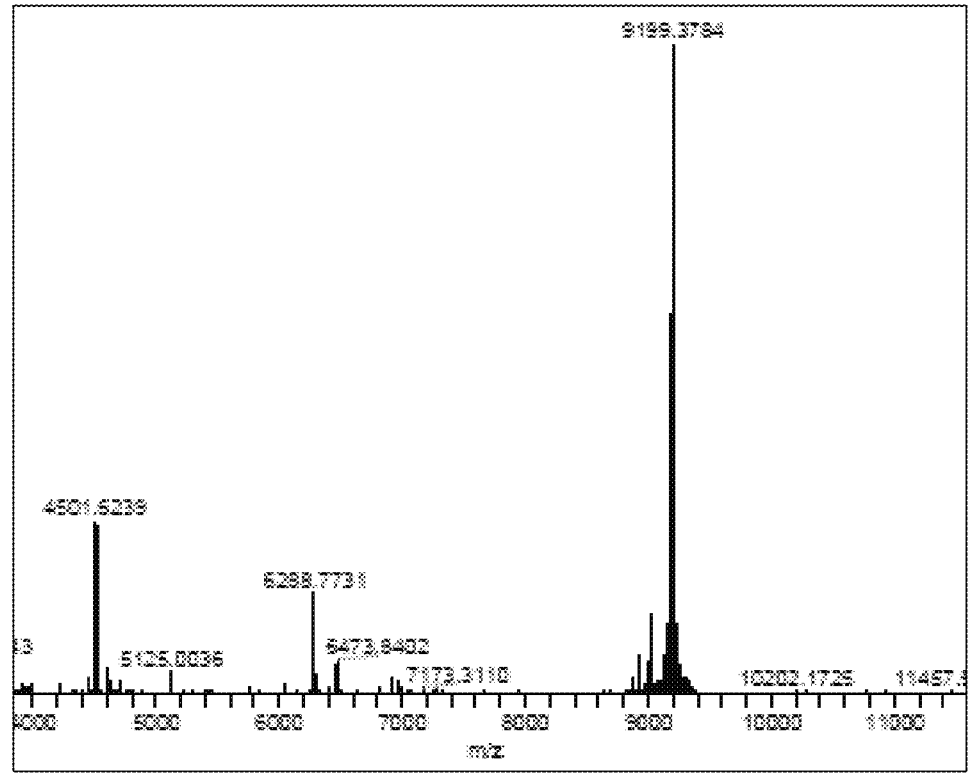

The final peptide was analyzed by reversed phase UPLC (FIG. 5A) and ESI-mass spectrometry (FIG. 5B). The theoretical molecular weight ($M_{theor}$=9199.3 Da) corresponds the observed molecular weight ($M_{obs}$=9199.4 Da).

3.7 Synthesis of all-D Polymerase X Variant V80A by Native Chemical Ligation of Peptide 4 with Peptide 3

Both peptides 3 and 4 were solved 0.2 M in TRIS-buffer (pH 8.6) containing 6 M GuanidinHCl (Sigma Aldrich Chemie GmbH, Schnelldorf, Germany), 200 mM mercaptophenyl-acetic acid (Sigma Aldrich Chemie GmbH, Schnelldorf, Germany) and 5 mm Tris(2-carboxyethyl)phosphine hydrochloride (Sigma Aldrich Chemie GmbH, Schnelldorf, Germany). The reaction mixture was shaking 72 h by room temperature. Afterwards the mixture was purified by reversed phase HPLC using a RP-8-column (Phenomenex, Aschaffenburg, Germany) with a gradient of ACN in water of 30% to 60% within 30 min. Fractions which contained the ligation product were pooled and dried. The dry powder was solved in water and purified by size exclusion chromatography using a SEC3000-column (Phenomenex, Aschaffenburg, Germany) with sodium-buffer phosphate (Sigma Aldrich Chemie GmbH, Schnelldorf, Germany) (50 mM, pH 6.8, 0.5% SDS) as eluent. Product containing fractions were combined and freeze dried.

Figure 6A:
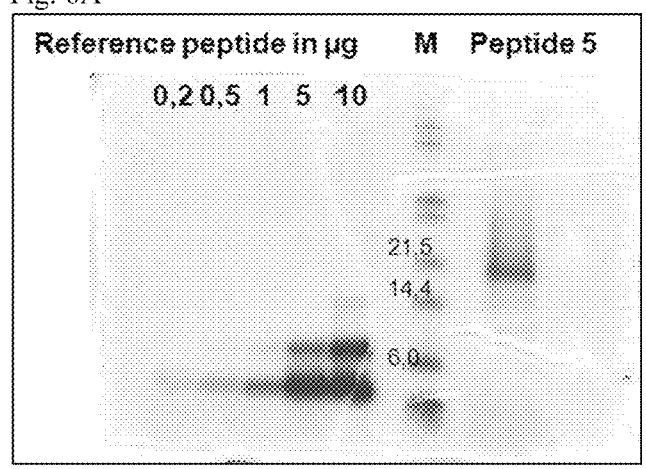
Figure 6B:
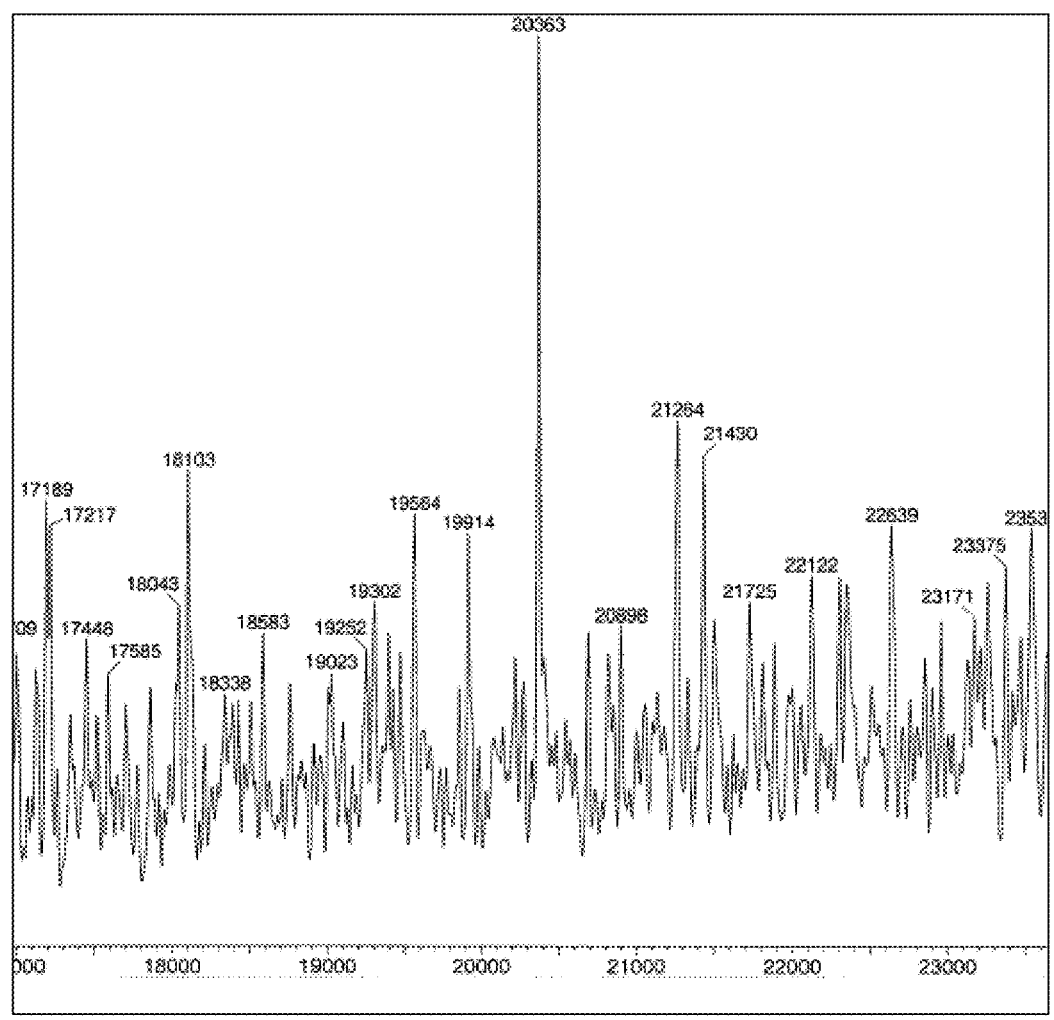

The final product was analyzed by SDS-PAGE (FIG. 6A) and ESI-mass spectrometry (FIG. 6B). A clear band was found in lane 7 between 14.4 kDa and 21.5 kDa indicating the pure full length polymerase. The theoretical molecular weight ($M_{theor}$=20342 Da) corresponds the observed molecular weight ($M_{obs}$=20361 Da) as shown by ESI-MS.

Example 4—Activity Confirmation of Synthetic Polymerase X Variant Consisting of D-Amino Acids The dry all-D polymerase X variant V80A according to example 3 was dissolved in 6 M guanidinium hydrochloride and refolded at 4° C. by step-wise dialysis in commercially available dialysis devices (Pierce/PerBio, Bonn, Germany) with 3,500 molecular weight cut-off. Final buffer was 50 mM sodium phosphate, 500 mM sodium chloride, pH 7.5. Protein concentration was estimated by sodium dodecyl sulphate (SDS) polyacrylamide gel electrophoresis (PAGE) on pre-cast gels (Invitrogen, Karlsruhe, Germany) using a standard series of known protein concentrations followed by SYPRO-RED staining (Invitrogen, Karlsruhe, Germany) and densitometric band analysis on a BioRad Fx scanner instrument.

The activity assay for the all-D polymerase X variant V80A was done with two different substrate types:

4.1 Activity Assays on Substrates with 1-Nucleotide Gap

Substrates were made by annealing a 33-mer lower strand DNA oligonucleotide with two 17-mer upper strand DNA oligonucleotides resulting in a gap of 1 nucleotide in the upper strand. Oligonucleotides were synthesized in L-configuration. Before annealing, 17-mer upper strand oligonucleotide MJ_1_58_MD was radioactively labeled at its 5'-end with $^{32}$P by a standard kinase reaction employing Gamma-$^{32}$P-Adenosine-Triphosphate (Gamma-$^{32}$P-ATP) and T4 polynucleotide kinase. To facilitate the kinase reaction of the L-oligonucleotide MJ_1_58_MD, two D-configurated guanosine bases were added at the 5' end during oligonucleotide synthesis. Annealing was done in 10 mM Tris-HCl, 5 mM MgCl$_2$, pH 8.0 by heating 10 min at 65° C. and slowly cooling down. Unincorporated gamma-32P-ATP was removed by purification over NAP-columns (GE healthcare, Freiburg, Germany). The complexes contained either A, C, G or T at the template position within the gap. For the setup of the substrate complexes see FIG. 7.

In the activity assay, synthetic all-D polymerase X variant V80A was combined with L-configurated 1-gap substrate complexes. As a negative control, each substrate was also incubated without all-D polymerase X variant V80A and L-desoxy-nucleotide-triphosphates (dNTP's). Depending on the template base within the 1-gap complex only the corresponding L-dNTP was added during the assay. A typical 6 µl assay contained 50 nM substrate complex, 1.7 ng/µl all-D polymerase X variant V80A, 8 µM of one L-dNTP and buffer (50 mM Tris-HCl, 10 mM MgCl$_2$, 4% glycerol, 0.1 mg/ml bovine serum albumin (BSA), pH 7.5). L-dNTP's were purchased as custom synthesis from Rasayan, Inc. (Encinitas, Calif., USA). The incubation time was 30 minutes at 37° C. The whole assay volume was mixed with sample buffer/dye, loaded on a denaturing sequencing gel a separated for 4 hours. The gel was exposed to Kodak K screen overnight at −80° C. and read out using BioRad Fx phosphoimager system.

Figure 8:
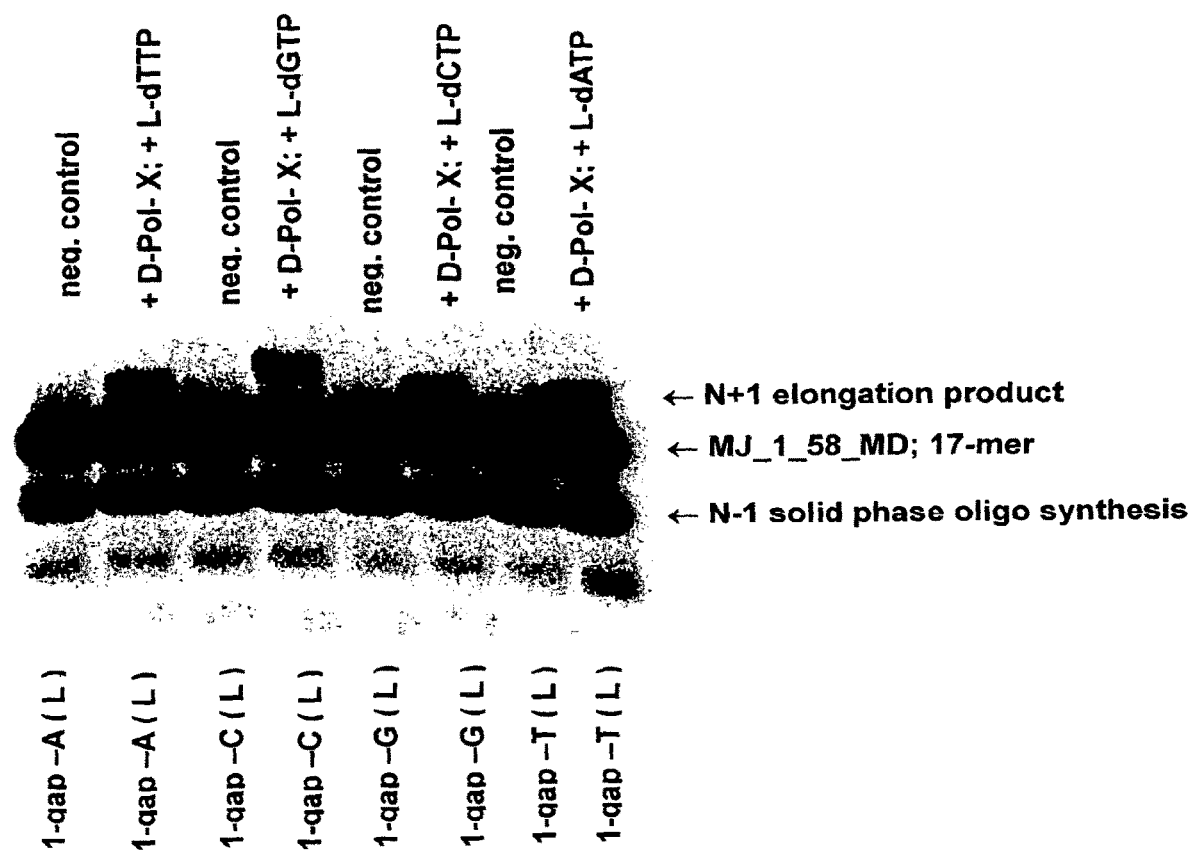
FIG. 8 shows gel electrophoresis of L-DNA elongation activity assay of D-polymerase X on 1-gap substrates.

As can be seen from FIG. 8, all-D polymerase X variant V80A gives elongation products on L-DNA 1-gap substrates, thus confirming the activity of the synthetic protein. Noteworthy, only all-D polymerase X variant V80A combined with L-substrate and L-dNTP's gave any elongation product. Also, only samples containing the L-dNTP corresponding to their template base yielded elongation product. That means on the A-complex the dTTP nucleotide, on the C-complex the dGTP nucleotide, on the G-complex the dCTP nucleotide and on the T-complex the dATP nucleotide had to be present to yield any elongation product.

4.2 Activity Assay on Substrates with 6-Nucleotide Gap

Substrates were made by annealing a 33-mer lower strand DNA oligonucleotide with two 17-mer and 12-mer upper strand DNA oligonucleotides resulting in a gap of 6 nucleotides in the upper strand. Oligonucleotides were synthesized in L-configuration. Before annealing, 17-mer upper strand oligonucleotide MJ_1_58_MD (L-configuration) was radioactively labeled at its 5'-end with $^{32}$P by a standard kinase reaction employing Gamma-$^{32}$P-Adenosine-Triphosphate (ATP) and T4 polynucleotide kinase. To facilitate the kinase reaction of the L-oligonucleotide MJ_1_58_MD, two D-configurated guanosine bases were added at the 5' end during oligonucleotide synthesis. Annealing was done in 10 mM Tris-HCl, 5 mM MgCl$_2$, pH 8.0 by heating 10 min at 65° C. and slowly cooling down. Unincorporated Gamma-$^{32}$P-ATP was removed by purification over NAP-columns (GE healthcare, Freiburg, Germany). For the setup of the substrate complexes see FIG. 9A.

In the activity assay synthetic all-D polymerase X variant V80A was combined with L-configurated 6-gap substrate complex. As a negative control, the substrate was also incubated without all-D polymerase X variant V80A and desoxy-nucleotide-triphosphates (L-dNTP's). A typical 6 µl assay contained 50 nM substrate complex, up to 1.3 ng/µl all-D polymerase X variant V80A, 8 µM each of the L-dNTP's and buffer (50 mM Tris-HCl, 10 mM MgCl$_2$, 4% glycerol, 0.1 mg/ml bovine serum albumin (BSA), pH 7.5). L-dNTP's were purchased as custom synthesis by Rasayan, Inc. (Encinitas, Calif., USA). A typical incubation time was 30 minutes at 37° C., but depending on activity of the batch longer incubations were used. The whole assay volume was mixed with sample buffer/dye, loaded on a denaturing sequencing gel a separated for 4 hours. The gel was exposed to Kodak K screen overnight at −80° C. and read out using BioRad Fx phosphoimager system.

Figures 9A, 9B:
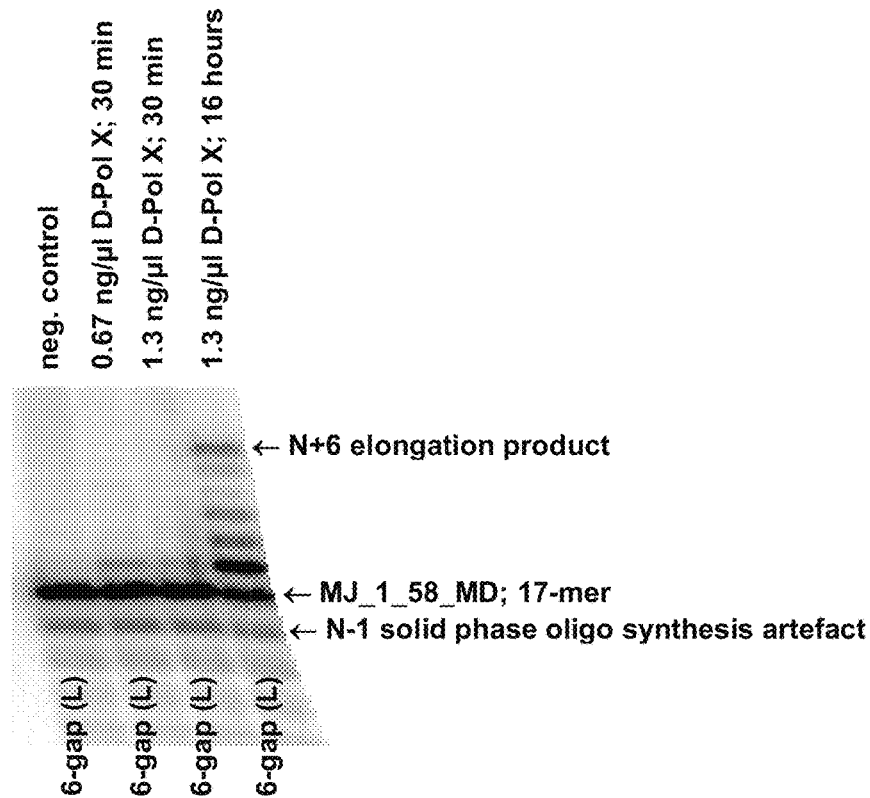
FIG. 9A shows composition of 6-gap L-DNA templates for activity test of D-polymerase X.
FIG. 9B shows gel electrophoresis of L-DNA elongation activity assay of D-polymerase X on 6-gap substrate.

As can be seen from FIG. 9B, synthetic all-D polymerase X variant V80A gives N+6 elongation products on L-DNA 6-gap substrates, thus confirming the activity of the synthetic protein. However, synthesis of N+6 elongation product was less evident than N+1 elongation product on the same 6-gap complex. Also increased incubation time was necessary to fill the 6-gap. Noteworthy, only all-D polymerase X variant V80A combined with L-substrate plus L-dNTP's gave any elongation product.

Example 5—DNA Synthesis by Polymerase X and Variants of Polymerase X

Polymerase X from African Swine Fever Virus (abbr. ASFV) is described in literature (Oliveros, 1997) as a highly distributive enzyme with gap-repair function. As shown in example 2 all-L-polymerase X and variants thereof has been shown to catalyze the incorporation of only very few nucleotides after each initiation on gapped substrates. Here we disclose a method which allows using all-L-polymerase X and variants for synthesizing longer DNA and show complete polymerization of a 83-mer strand.

5.1 Primer-Template Substrate

A primer-template complex has been used to test activity of all-L-polymerase X and variants thereof. The same complex has also been used to test variants V80G and V80A of the all-L-polymerase X.

List of D-oligonucleotides for the primer-template complex without nap:

| Name | Length, nt | Configuration | Sequence (5'→3') |
| --- | --- | --- | --- |
| MJ_1_33_DD | 19 | D | Atto532-GGAGCTCAGACTGGCACGC |
| MJ_1_1_DD | 83 | D | GTGGAACCGACAACTTGTGCTGCGTCCAGCATAAGAAAGGAG CTCCCTCAGAAGAAGCTGCGCAGCGTGCCAGTCTGAGCTCC |

Figures 10A, 10B:
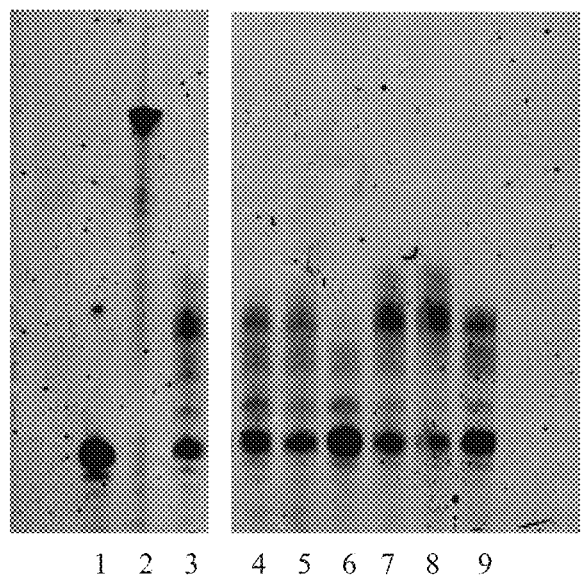
FIG. 10A shows primer-template complex D-DNA substrate for activity assay of L-polymerase X.
FIG. 10B shows gel electrophoresis of D-DNA elongation activity assay of L-polymerase X performed at constant temperature.

The substrate was made by annealing a template strand DNA oligonucleotide consisting of 83 nucleotides (MJ_1_1_DD) with a DNA oligonucleotide consisting of 19 nucleotides. Oligonucleotides were synthesized at NOXXON. The oligonucleotide MJ_1_33_DD carries the fluorescent dye Atto-532 (AttoTec, Siegen, Germany). Annealing was done in 10 mM Tris-HCl, 5 mM MgCl2, pH 8.0 by heating 10 min at 65° C. and slowly cooling down. The primer-template complex is depicted in FIG. 10A.

5.2 Reaction at Constant Temperature

In the activity assay, all-L-polymerase X or variants V80G or V80A of all-L-polymerase X were combined with D-configurated primer-template complex. A typical 6 μl assay contained 50 nM substrate complex, up to 1.3 ng/μl all-L-polymerase X or variants V80G or V80A of all-L-polymerase X, 8 μM each of the D-dNTP's and buffer (50 mM Tris-HCl, 10 mM MgCl$_2$, 4% glycerol, 0.1 mg/ml bovine serum albumin (BSA), pH 7.5). D-dNTP's were purchased from Rovalab (Teltow, Germany). Incubation time was 30 minutes at 37° C. for Pol-X samples. As a negative control, the substrate was also incubated without any all-L-polymerase X or variants V80G or V80A of all-L-polymerase X and without desoxy-nucleotide-triphosphates (D-dNTP's). A positive control was conducted with Taq polymerase (Invitrogen, Karlsruhe, Germany) used at final concentration of 0.083 U/μl in Taq buffer supplied by manufacturer. Taq samples were incubated 30 minutes at 60° C. The whole assay volume was mixed with sample buffer/dye, and separated on a denaturing gel. The gel was read out using BioRad Fx phosphoimager system.

All-L-polymerase X or variants V80G or V80A all-L-polymerase X were active, but were not able to complete the polymerization of the full 83-mer template. The Taq polymerase positive control shows complete polymerization of the 83-mer template, see FIG. 10B.

5.3 Reaction Under Thermal Cycling Conditions

Under the assumption that all-L-polymerase X after initiation catalyzes the incorporation of only one nucleotide and then pauses while staying on the DNA substrate, we performed repeated heat pulses (50° C., 2 minutes) in order to allow all-L-polymerase X for dissociation from and reassociation to the template. Using this repeated thermal cycling procedure we were able to perform full polymerization of the 83-mer with all-L-polymerase X. Reactions and controls were set-up as described above for constant temperature, except that the temperature profile for all-L-polymerase X samples was run as follows:

5 to 25 cycles of (30 minutes at 20° C.//2 minutes at 50° C.)

then a final step of 30 minutes at 20° C.

Figure 10C:
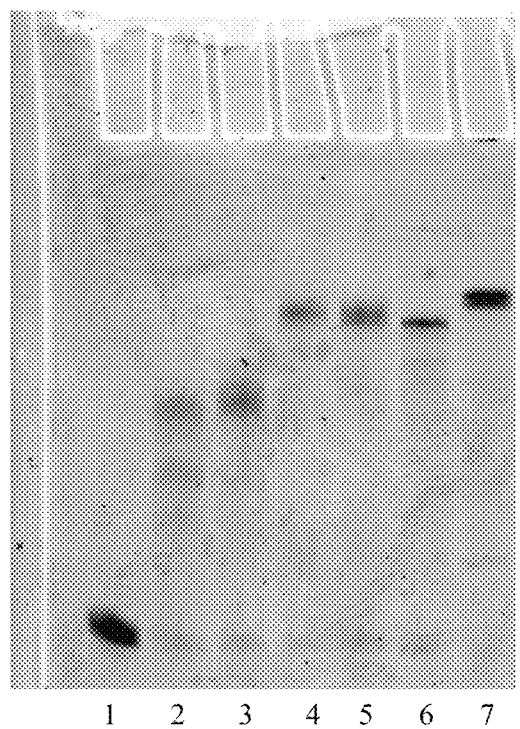
FIG. 10C shows gel electrophoresis of D-DNA elongation activity assay of L-polymerase X performed using thermal cycling.

It was observed that from 15 cycles onwards all-L-polymerase X was able to polymerize the full 83-mer template strand, similar to the positive control, see FIG. 10C.

Example 6—Primer Elongation with a Synthetic Polymerase X Variant Consisting of D-Amino Acids The method disclosed in this example uses L-configurated substrates for testing all-D configurated polymerase.

6.1 Primer-Template Substrate

List of L-oligonucleotides for the primer-template complex without gap:

| Name | Length, nt | Configuration | Sequence (5'→3') |
| --- | --- | --- | --- |
| MJ_1_109_MD | 21 | first two = D, others L | D(GG)-L(GGAGCTCAGACTGGCACGC) |

| Name | Length, nt | Configuration | Sequence (5'→3') |
|---|---|---|---|
| MJ_1_105_LD | 83 | L | GTGGAACCGACAACTTGTGCTGCGTCCAGCATAAGAAAGGAG CTCCCTCAGAAGAAGCTGCGCAGCGTGCCAGTCTGAGCTCC |

The substrate is made by annealing a 83-mer lower strand DNA oligonucleotide with the 19-mer upper strand DNA oligonucleotide. Oligonucleotides are synthesized at NOXXON's in-house facility in L-configuration. Before annealing, 21-mer upper strand oligonucleotide MJ_1_109_MD is radioactively labeled at its 5'-end with $^{32}$P by a standard kinase reaction employing Gamma-$^{32}$P-Adenosine-Triphosphate (ATP) and T4 polynucleotide kinase. To facilitate the kinase reaction of the L-oligonucleotide MJ_1_109_MD, two D-configurated guanosine bases are added at the 5' end during oligonucleotide synthesis. Annealing is done in 10 mM Tris-HCl, 5 mM MgCl$_2$, pH 8.0 by heating 10 min at 65° C. and slowly cooling down. Unincorporated Gamma-$^{32}$P-ATP is removed by purification over NAP-columns (GE healthcare, Freiburg, Germany).

6.2 Reaction at Constant Temperature

In the activity assay, synthetic all-D polymerase X variant V80A is combined with L-configurated primer-template complex. A typical 6 µl assay contains 50 nM substrate complex, up to 1.3 ng/µl all-D polymerase X variant, 8 µM each of the L-dNTP's and buffer (50 mM Tris-HCl, 10 mM MgCl$_2$, 4% glycerol, 0.1 mg/ml bovine serum albumin (BSA), pH 7.5). L-dNTP's were purchased from Rasayan, Inc. (Encinitas, Calif., USA). Incubation time is at least 30 minutes at 37° C. As a negative control, the substrate is also incubated without any polymerase and without desoxynucleotide-triphosphates (L-dNTP's). The whole assay volume is mixed with sample buffer/dye, and separated on a denaturing gel. The gel is read out using BioRad Fx phosphoimager system.

The synthetic all-D polymerase X variant V80A is active under this condition, but—similar to the all-L polymerase X counterpart—is not able to polymerize the full 83 nucleotide template strand.

6.3 Reaction Under Thermal Cycling Conditions

Analog to example 5 a repeated thermal cycling procedure is used to allow for full polymerization of the 83-mer L-substrate with all-D Polymerase X variant V80A. Reactions and controls are set-up as described above for constant temperature, except that the temperature profile was run as follows:

5 to 25 cycles of (30 minutes at 20° C.//2 minutes at 50° C.)

then a final step of 30 minutes at 20° C.

It is observed that all-D polymerase X variant V80A—similar to the all-L polymerase X counterpart—is able to polymerize the full 83-mer template strand when using thermal cycle elongation.

Example 7—Recombinant Expression and Purification of Polymerase Dpo4 and Variants of Polymerase Dpo4, all Consisting of L-Amino Acids The polymerase Dpo4 was originally discovered in *Sulfolobus Solfataricus* (abbr. Sso) (Boudsocq, 2001). The wild-type gene has an open reading frame (abbr. ORF) of 1,059 base pairs including start codon and stop codon. The encoded protein has a length of 352 amino acids. This example describes how polymerase Dpo4 and variants of polymerase Dpo4 have been expressed in *E. coli* and been purified using Strep-Tag.

7.1 Expression Constructs

Since the codon usage of Sso differs from *E. coli*, an *E. coli*-codon-optimized synthetic gene for wild-type Sso polymerase Dpo4 was purchased from GeneArt AG (Regensburg, Germany). The synthetic gene sequence was provided in pENTRY-IBA10 vector (originator company: IBA GmbH, Göttingen, Germany). The codon-optimized open reading frame including start codon, but not including stop codon had the following sequence:

ATGATTGTGCTGTTTGTGGATTTTGATTATTTTTATGCCCAGGTGGAAGA

AGTTCTGAATCCGAGCCTGAAAGGTAAACCGGTTGTTGTTTGTGTTTTTA

GCGGTCGCTTTGAAGATAGCGGTGCAGTTGCAACCGCCAATTATGAAGCC

CGTAAATTTGGTGTTAAAGCCGGTATTCCGATTGTTGAAGCCAAAAAAAT

TCTGCCGAATGCAGTTTATCTGCCGATGCGCAAAGAAGTTTATCAGCAGG

TTAGCAGCCGTATTATGAATCTGCTGCGCGAATATAGCGAAAAAATTGAA

ATTGCCAGCATTGATGAAGCCTATCTGGATATTAGCGATAAAGTGCGCGA

TTATCGCGAAGCATATAATCTGGGCCTGGAAATTAAAAATAAAATCCTGG

AAAAAGAAAAAATTACCGTGACCGTGGGCATTAGCAAAAATAAAGTGTTT

GCCAAAATTGCAGCAGATATGGCAAAACCGAATGGCATTAAAGTGATTGA

TGATGAAGAAGTGAAACGTCTGATTCGCGAACTGGATATTGCAGATGTTC

CGGGTATTGGCAATATTACCGCAGAAAAACTGAAAAAACTGGGCATTAAT

AAACTGGTTGATACCCTGAGCATTGAATTTGATAAACTGAAAGGCATGAT

TGGTGAAGCGAAAGCCAAATATCTGATTAGCCTGGCACGTGATGAATATA

ATGAACCGATTCGTACCCGTGTTCGTAAAAGCATTGGTCGTATTGTGACC

ATGAAACGCAATAGCCGTAATCTGGAAGAAATTAAACCGTACCTGTTTCG

TGCAATTGAAGAAAGCTATTATAAACTGGATAAACGCATTCCGAAAGCCA

TTCATGTTGTTGCAGTTACCGAAGATCTGGATATTGTTAGCCGTGGTCGT

ACCTTTCCGCATGGTATTAGCAAAGAAACCGCCTATAGCGAAAGCGTTAA

ACTGCTGCAGAAAATCCTGGAAGAAGATGAACGTAAAATTCGTCGTATTG

GTGTGCGCTTTAGCAAATTTATTGAAGCCATTGGCCTGGATAAATTTTTT

GATACC.

In order to obtain the expression construct for polymerase Dpo4, also referred to as all-L-polymerase Dpo4, the gene was subcloned from pENTRY-IBA10 into the pASG-IBA5 vector (IBA GmbH, Göttingen, Germany), using a commercially available StarGate cloning kit (IBA GmbH). Subcloning added a Strep-Tag II to the N-terminus and a stop codon to the C-terminus, and brought the gene under control of the tet promoter. The construct was named pMJ343 and was used for expression of all-L-polymerase Dpo4 in *E. coli*. The all-L-polymerase Dpo4 expressed from pMJ343 had the following sequence of 368 amino acids:

MASAWSHPQFEKSGMIVLFVDFDYFYAQVEEVLNPSLKGKPVVVCVFSGR

FEDSGAVATANYEARKFGVKAGIPIVEAKKILPNAVYLPMRKEVYQQVSS

RIMNLLREYSEKIEIASIDEAYLDISDKVRDYREAYNLGLEIKNKILEKE

KITVTVGISKNKVFAKIAADMAKPNGIKVIDDEEVKRLIRELDIADVPGI

-continued

GNITAEKLKKLGINKLVDTLSIEFDKLKGMIGEAKAKYLISLARDEYNEP

IRTRVRKSIGRIVTMKRNSRNLEEIKPYLFRAIEESYYKLDKRIPKAIHV

VAVTEDLDIVSRGRTFPHGISKETAYSESVKLLQKILEEDERKIRRIGVR

FSKFIEAIGLDKFFDTGS.

The initial 14 amino acids represented the Strep-Tag II including a few spacer amino acids, the final 2 amino acids represented spacer amino acids, and the middle 352 amino acid part was identical to the polymerase Dpo4 sequence as found in Sso.

Expression constructs for variants of all-L-polymerase Dpo4 were made using the commercially available QuikChange kit (Stratagene GmbH, Waldbronn, Germany) according to manufacturer's protocol. Plasmid pMJ343 served as template. Oligonucleotides needed for QuikChange were either synthesized at NOXXON (QC_38_up, QC_38_low, QC_39_up, QC_39_low, QC_40_up, QC_40_low) or purchased from Purimex (Grebenstein, Germany) (QC_28_up, QC_28_low, QC_29_up, QC_29_low, QC_30_up, QC_30_low).

The following variant expression constructs were made and used for expression of the variants of all-L-polymerase Dpo4 in *E. coli*

| variant | construct | oligonucleotides used for QuikChange mutagenesis procedure |
|---|---|---|
| A155C | pMJ361 | QC_28_up<br>(5'CAAAAATAAAGTGTTTGCCAAAATTGCATGCGATATGGCAAAACCG AATGGCATTAAAG 3')<br>QC_28_low<br>(5'CTTTAATGCCATTCGGTTTTGCCATATCGCATGCAATTTTGGCAAA CACTTTATTTTTG 3') |
| V203C | pMJ362 | QC_29_up<br>(5'TGAAAAAACTGGGCATTAATAAACTGTGTGATACCCTGAGCATTGA ATTTG 3')<br>QC_29_low<br>(5'CAAATTCAATGCTCAGGGTATCACACAGTTTATTAATGCCCAGTTT TTTCA 3') |
| C31S | pMJ363 | QC_30_up<br>(5'TGAAAGGTAAACCGGTTGTTGTTTCTGTTTTTAGCGGTC 3')<br>QC_30_low<br>(5'GACCGCTAAAAACAGAAACAACAACCGGTTTACCTTTCA 3') |
| A155C + V203C | pMJ365 | QC_28_up<br>QC_28_low<br>QC_29_up<br>QC_29_low |
| S85C | pMJ502 | QC_38_up<br>(5'ATGCGCAAAGAAGTTTATCAGCAGGTTTGTAGCCGTATTATGAATC 3')<br>QC_38_low<br>(5'GATTCATAATACGGCTACAAACCTGCTGATAAACTTCTTTGCGCAT-3') |
| S86C | pMJ503 | QC_39_up<br>(5'AAGTTTATCAGCAGGTTAGCTGTCGTATTATGAATCTGCTGCG 3')<br>QC_39_low<br>(5'CGCAGCAGATTCATAATACGACAGCTAACCTGCTGATAAACTT 3') |
| S96C | pMJ504 | QC_40_up<br>(5'ATTATGAATCTGCTGCGCGAATATTGTGAAAAAATTGAAATTGCCA GCATT 3')<br>QC_40_low<br>(5'AATGCTGGCAATTTCAATTTTTTCACAATATTCGCGCAGCAGATTC ATAAT 3') |

7.2 Protein Expression in *E. coli*

All-L-polymerase Dpo4 was expressed in *E. coli* using expression construct pMJ343. Mutant variants of all-L-polymerase Dpo4 were expressed from pMJ361, pMJ362, pMJ363, pMJ365, pMJ502, pMJ503 or pMJ504. For expression, the appropriate expression construct was transformed in *E. coli* strain 'NEB express' (New England Biolabs, Frankfurt am Main, Germany) using 'Transformation and Storage Solution' (Epicentre/Biozym, Hessisch Oldendorf, Germany) and maintained with the antibiotic Ampicillin. Expression was done in medium 'EnBase Flo' or 'EnPresso' (BioSilta, Oulu, Finland) for 48 h at 30° C. using 200 ng/ml Anhydrotetracyclin (IBA GmbH, Göttingen, Germany) as inducer. Cells were harvested by centrifugation and either stored at −80° C. or immediately processed.

7.3 Protein Purification

Fresh or frozen *E. coli* cells were resuspended on ice in 'Buffer W' (100 mM Tris-HCl, pH 8.0, 150 mM NaCl, 1 mM EDTA) and lysed using a 'French Press' (G. Heinemann, Schwäbisch Gmünd, Germany) cell disrupter. Purification was done at 4° C. on an 'ÄKTA Express' system equipped with 5 ml StrepTrap HP columns (GE healthcare, Freiburg, Germany). Step elution was done with Buffer W including 2.5 mM Desthiobiotin (IBA GmbH, Göttingen, Germany) Fractions were analyzed using SDS-PAGE (Invitrogen, Karlsruhe, Germany), pooled and, if required, further purified with anion-ion-exchange chromatography on an 'ÄKTA purifier' system equipped with 'Q HP' columns (GE healthcare, Freiburg, Germany). Protein identity was confirmed by LC-MS mass spectometry and correct fractions were pooled, concentrated and re-buffered using VivaSpin 15R concentration devices with 10,000 molecular weight cut-off (MWCO) (VivaSciences/Sartorius Stedim Biotech, Göttingen, Germany). Purified protein was stored at -20° C. in a buffer consisting of 100 mM KCl, 10 mM Tris-HCl pH 7.4, 0.1 mM EDTA, 1 mM DTT, 50% glycerol. Protein concentrations were estimated by gel-densiometry using a bovine serum albumin (abbr. BSA) standard on SDS-PAGE and staining with SYPRO Red (Invitrogen, Karlsruhe, Germany).

Example 8—Production of a Synthetic Polymerase Dpo4 Consisting of Two Fragments All-L polymerase Dpo4 has a length of 352 amino acids. In order to chemically produce the all-L polymerase Dpo4, such a synthetic all-L polymerase Dpo4 had to be assembled from shorter fragments that can be synthesized by solid-phase peptide synthesis, wherein said shorter fragments had to be ligated by a peptide ligation method such as the native chemical ligation. This example describes how ligation fragments 1-154, 155-352, 155-202 and 203-352 of Dpo4 have been expressed in *E. coli*, purified and ligated to each other by native chemical ligation to yield the synthetic all-L-polymerase Dpo4.

8.1 Expression Constructs

As disclosed in example 7 the gene for all-L-polymerase Dpo4 has been obtained as a synthetic gene construct from a commercial source (GeneArt, Regensburg, Germany). All fragments of this example were cloned based on that codon-optimized sequence. The following expression constructs for fragments 1-154, 155-352, 155-202 and 203-352 of the all-L-polymerase Dpo4 variant A155C were made:

| Fragment of Dpo4 (amino acid range) | expression construct |
|---|---|
| 1-154-thioester | pMJ370 |
| 155-352 contained A155C mutation | pMJ384 |
| 203-352 contained A155C mutation | pMJ385 |
| 155-202 thioester | pMJ388 |

8.1.1 Fragment 1-154-Thioester of all-L-Polymerase Dpo4 Variant A155C—Expression Construct pMJ370

This construct contains the fragment 1-154 of the all-L-polymerase Dpo4 variant A155C followed by an Mxe GyrA intein, which was used to produce the thioester, and a chitin-binding domain (CBD). The construct was assembled from two PCR products. PCR product 1 was made using pMJ343 as a template and primers MJ_1_90_DD (5'-Phosphate-AGCGGCTCTTCGATGATTGTGCTGTTTGTG-GATTTT-3') and MJ_1_91_DD (5'-Phosphate-AGCGGCTCTTCGGCATGCAATTTTGGCAAACACTTT-3') to amplify the fragment 1-154 of all-L-polymerase Dpo4 variant A155C. PCR product 2 was made using pTWIN1 (New England Biolabs, Frankfurt am Main, Germany) as a template and primers MJ_1_72_DD (5'-Phosphate-AGCGGCTCTTCGTGCATCACGGGAGAT-3') and MJ_1_73_DD (5'-Phosphate-AGCGGCTCTTCGCCCTT-GAAGCTGCCACAAGGCAGGAACGTT-3') to amplify the Mxe Gyr A intein and the CBD. Primers MJ_1_90_DD and MJ_1_91_DD were from Purimex (Grebenstein, Germany) while primers MJ_1_72_DD and MJ_1_73_DD were from IBA GmbH (Göttingen, Germany). The two PCR products were gel-purified on a flash-gel system (LONZA, Basel, Switzerland) and cloned together in pENTRY-IBA20 using the StarGate Mutagenesis ENTRY cloning kit (IBA GmbH, Göttingen, Germany) to result in pMJ366. Subcloning from pMJ366 in pASG-IBAwt1 (IBA GmbH, Göttingen, Germany) using the StarGate Transfer cloning kit (IBA GmbH, Göttingen, Germany) yielded pMJ370. The construct pMJ370 encodes the fragment 1-154-thioester of all-L-polymerase Dpo4 variant A155C with the following protein sequence of 154 amino acids length (after intein cleavage/thioester production):

```
MIVLFVDFDYFYAQVEEVLNPSLKGKPVVVCVFSGRFEDSGAVATANYEA
RKFGVKAGIPIVEAKKILPNAVYLPMRKEVYQQVSSRIMNLLREYSEKIE
IASIDEAYLDISDKVRDYREAYNLGLEIKNKILEKEKITVTVGISKNKVF
AKIA-thioester.
```

8.1.2 Fragment 155-352 of all-L-Polymerase Dpo4 Variant A155C—Expression Construct pMJ384

This construct contains a 'Profinity eXact' tag followed by the fragment 155-352 of all-L-polymerase Dpo4 variant A155C. The 'Profinity eXact' tag was used for purification and proteolytic cleavage. The construct was assembled from two PCR products. PCR product 1 was made using pPAL7 (Bio-Rad, München, Germany) as a template and primers MJ_1_99_DD (5'-Phosphate-AGCGGCTCTTCGATGG-GAGGGAAATCAAACGGGGAA-3') and MJ_1_100_DD (5'-Phosphate-AGCGGCTCTTCGGCACAAAGCTTT-GAAGAGCTTGTC-3') to amplify the 'Profinity eXact' tag. PCR product 2 was made using pMJ361 as a template and primers MJ_1_96_DD (5'-Phosphate-AGCGGCTCTTCGTGCGATATGGCAAAACCGAATGG-CATTAAA-3') and MJ_1_97_DD (5'-Phosphate-AGCGGCTCTTCGCCCTTAGGTATCAAAAAATTTATC CAGG-3') to amplify the dpo4 fragment 155-352 containing the A155C mutation. Primers MJ_1_96_DD, MJ_1_97_DD, MJ_1_99_DD and MJ_1_100_DD were all from Purimex (Grebenstein, Germany). The 2 PCR products were gel-purified on a flash-gel system (LONZA, Basel, Switzerland) and cloned together in pENTRY-IBA20 using the StarGate Mutagenesis ENTRY cloning kit (IBA GmbH, Göttingen, Germany) to result in pMJ382. Subcloning from pMJ382 in pASG-IBA5 (IBA GmbH, Göttingen, Germany) using the StarGate Transfer cloning kit (IBA GmbH, Göttingen, Germany) yielded pMJ384. The construct pMJ384 encodes the fragment 155-352 of all-L-polymerase Dpo4 containing mutation A155C with the following protein sequence of 198 amino acids length (after proteolytic cleavage):

```
CDMAKPNGIKVIDDEEVKRLIRELDIADVPGIGNITAEKLKKLGINKLVD

TLSIEFDKLKGMIGEAKAKYLISLARDEYNEPIRTRVRKSIGRIVTMKRN

SRNLEEIKPYLFRAIEESYYKLDKRIPKAIHVVAVTEDLDIVSRGRTFPH

GISKETAYSESVKLLQKILEEDERKIRRIGVRFSKFIEAIGLDKFFDT.
```

8.1.3 Fragment 203-352 of all-L-Polymerase Dpo4 Variant A155C—Expression Construct pMJ385

This construct contains a 'Profinity eXact' tag followed by the dpo4 fragment 203-352 containing mutation V203C. The 'Profinity eXact' tag was used for purification and proteolytic cleavage. The construct was assembled from two PCR products. PCR product 1 was made using pPAL7 (Bio-Rad, München, Germany) as a template and primers MJ_1_99_DD (5'-Phosphate-AGCGGCTCTTCGATGG-GAGGGAAATCAAACGGGGAA-3') and MJ_1_100_DD (5'-Phosphate-AGCGGCTCTTCGGCACAAAGCTTT-GAAGAGCTTGTC-3') to amplify the 'Profinity eXact' tag. PCR product 2 was made using pMJ362 as a template and primers MJ_1_98_DD (5'-Phosphate-AGCGGCTCTTCGTGTGATACCCTGAGCATT-GAATTT-3') and MJ_1_97_DD (5'-Phosphate-AGCGGCTCTTCGCCCTTAGGTATCAAAAAATTTATC CAGG-3') to amplify the dpo4 fragment 203-352 containing the V203C mutation. Primers MJ_1_97_DD, MJ_1_98_DD, MJ_1_99_DD and MJ_1_100 DD were all from Purimex (Grebenstein, Germany). The 2 PCR products were gel-purified on a flash-gel system (LONZA, Basel, Switzerland) and cloned together in pENTRY-IBA20 using the StarGate Mutagenesis ENTRY cloning kit (IBA GmbH, Göttingen, Germany) to result in pMJ383. Subcloning from pMJ383 in pASG-IBA5 (IBA GmbH, Göttingen, Germany) using the StarGate Transfer cloning kit (IBA GmbH, Göttingen, Germany) yielded pMJ385. The construct pMJ385 encodes the dpo4 fragment 203-352 V203C with the following protein sequence of 150 amino acids length (after proteolytic cleavage):

```
CDTLSIEFDKLKGMIGEAKAKYLISLARDEYNEPIRTRVRKSIGRIVTMK

RNSRNLEEIKPYLFRAIEESYYKLDKRIPKAIHVVAVTEDLDIVSRGRTF

PHGISKETAYSESVKLLQKILEEDERKIRRIGVRFSKFIEAIGLDKFFDT
```

8.1.4 Fragment 155-202 of all-L-Polymerase Dpo4—Expression Construct pMJ388

This construct contains the dpo4 fragment 155-202 followed by an Mxe GyrA intein, which was used to produce the thioester, and a chitin-binding domain (CBD). The construct was assembled from two PCR products. PCR product 1 was made using pMJ343 as a template and primers MJ_1_101_DD (5'-Phosphate-AGCGGCTCTTC-GATGGCAGATATGGCAAAACCGAAT-3') and MJ_1_102_DD (5'-Phosphate-AGCGGCTCTTCGGCACAGTTTAT-TAATGCCCAGTTT-3') to amplify the dpo4 155-202 fragment. PCR product 2 was made using pTWIN1 (New England Biolabs, Frankfurt am Main, Germany) as a template and primers MJ_1_72_DD (5'-Phosphate-AGCGGCTCTTCGTGCATCACGGGAGAT-3') and MJ_1_73_DD (5'-Phosphate-AGCGGCTCTTCGCCCTT-GAAGCTGCCACAAGGCAGGAACGTT-3') to amplify the Mxe Gyr A intein and the CBD. Primers MJ_1_101_DD and MJ_1_102_DD were from Purimex (Grebenstein, Germany) while primers MJ_1_72_DD and MJ_1_73_DD were from IBA GmbH (Göttingen, Germany). The 2 PCR products were gel-purified on a flash-gel system (LONZA, Basel, Switzerland) and cloned together in pENTRY-IBA20 using the StarGate Mutagenesis ENTRY cloning kit (IBA GmbH, Göttingen, Germany) to result in pMJ386. Subcloning from pMJ386 in pASG-IBAwt1 (IBA GmbH, Göttingen, Germany) using the StarGate Transfer cloning kit (IBA GmbH, Göttingen, Germany) yielded pMJ388. The construct pMJ388 encodes the dpo4 fragment 155-202 with the following protein sequence of 48 amino acids length (after E. coli mediated cleavage of the inital Methionine and after intein cleavage/thioester production):

```
ADMAKPNGIKVIDDEEVKRLIRELDIADVPGIGNITAEKLKKLGINKL-thioester
```

8.2 Protein Expression in E. coli

For expression, the appropriate expression construct was transformed in E. coli strain 'NEB express' (New England Biolabs, Frankfurt am Main, Germany) using 'Transformation and Storage Solution' (Epicentre/Biozym, Hessisch Oldendorf, Germany) and maintained with the antibiotic Ampicillin. Expression was done in medium 'EnBase Flo' or 'EnPresso' (BioSilta, Oulu, Finland) at ambient temperature, using 200 ng/ml Anhydrotetracyclin (IBA GmbH, Göttingen, Germany) as inducer during an overnight period. Cells were harvested by centrifugation and either stored at −80° C. or immediately processed.

8.3 Purification and Generation of a Thioester from Constructs pMJ370 and pMJ388 with Mxe Gyr A Intein Fresh or frozen E. coli cells were resuspended on ice in 'column buffer' (20 mM HEPES, pH 8.5, 500 mM NaCl) and lysed using a 'French Press' (G. Heinemann, Schwäbisch Gmünd, Germany) cell disrupter. Purification was done at 4° C. on an 'ÄKTA Express' system (GE healthcare, Freiburg, Germany) equipped with columns containing chitin binding beads (New Englands Biolabs, Frankfurt am Main, Germany). After applying cell lysate and washing with column buffer until baseline, the columns were incubated 20 hours at 4° C. with 50 mM 2-mercaptoethane sulfonate (abbr. MESNA) in column buffer to induce intein-mediated protein cleavage and thioester formation. Cleaved protein carrying thioester was washed out of the column with column buffer, concentrated and subjected to gelfiltration using BioGel P60 medium material (BioRad, München, Germany) in a buffer consisting of 5 mM Bis-Tris, pH 6.5, 250 mM NaCl. Protein concentrations were estimated by gel-densiometry using a bovine serum albumin (BSA) standard on SDS-PAGE and staining with SYPRO Red (Invitrogen, Karlsruhe, Germany). Protein identity and the presence of the thioester were confirmed by LC-MS mass spectrometry.

8.4 Purification and Proteolytic Cleavage from Construct pMJ384 with 'Profinity eXact' Tag Purification of fragment 155-352 of the all-L-polymerase Dpo4 variant A155C from pMJ384 was done as follows: Fresh or frozen E. coli cells were resuspended on ice in 'Buffer W' (100 mM Tris-HCl, pH 8.0, 150 mM NaCl, 1 mM EDTA) and lysed using a 'French Press' (G. Heinemann, Schwäbisch Gmünd, Germany) cell disrupter. Purification was done at 4° C. on an 'ÄKTA Express' system equipped with 5 ml StrepTrap HP columns (GE healthcare, Freiburg, Germany). Step elution was done with Buffer W including 2.5 mM Desthiobiotin (IBA GmbH, Göttingen, Germany). Eluted protein was subjected to buffer exchange in 'Profinity eXact elution buffer' (0.1 M Na-phosphate, pH 7.2, 0.1 M NaF) using a HiPrep 26/10 desalting column (GE healthcare, Freiburg, Germany) and then slowly pumped through a Profinity eXact column. The sample was concentrated, supplemented with Tris(2-carboxyethyl)phosphine) (TCEP) to 1 mM final concentration and applied to gelfiltration using a HiLoad 16/60 Superdex 75 prep grade column (GE healthcare, Freiburg, Germany) developed in a buffer consisting of 5 mM Bis-Tris, pH 6.5, 250 mM NaCl. Protein was concentrated and stored at −80° C. Protein concentrations were estimated by gel-densiometry using a bovine serum albumin (BSA) standard on SDS-PAGE and staining with SYPRO Red (Invitrogen, Karlsruhe, Germany). Protein identity was confirmed by LC-MS mass spectrometry.

8.5 Purification and Proteolytic Cleavage from Construct pMJ385 with 'Profinity eXact' Tag Purification of dpo4 fragment 203-352 V203C from pMJ385 was done as follows: Inclusion bodies were prepared and denatured as described in the 'i-FOLD Protein refolding system' manual (Novagen/Merck-Millipore, Darmstadt, Germany). Solubilized protein was subjected to buffer exchange into 'Buffer W' (100 mM Tris-HCl, pH 8.0, 150 mM NaCl, 1 mM EDTA) using Sephadex G-25 fine material (GE healthcare, Freiburg, Germany) and purified at 4° C. on an 'ÄKTA Express' system equipped with Strep-Trap HP columns (GE healthcare, Freiburg, Germany). Step elution was done with Buffer W including 2.5 mM Desthiobiotin (IBA GmbH, Göttingen, Germany). Eluted protein solution was supplemented with NaF to a final concentration of 0.1 M and Tris(2-carboxyethyl)phosphine) (TCEP) to a final concentration of 1 mM and then slowly pumped through a Profinity eXact column. Flowthrough was diluted 1:3 with deionized water and pH adjusted to 7.2 using HCl. The sample was further purified by cation-exchange-chromatography using HiTrap SP HP columns (GE healthcare, Freiburg, Germany) equilibrated in 'Buffer A' (50 mM Na-Phosphate, pH 7.2, 1 mM 2-mercaptoethanol). Step elution was done using 17%, 25% and 100% of 'Buffer B' (50 mM Na-Phosphate, pH 7.2, 1 M NaCl, 1 mM 2-mercaptoethanol). Fractions were pooled, concentrated and applied to gelfiltration using a HiLoad 16/60 Superdex 75 prep grade column (GE healthcare, Freiburg, Germany) developed in deionized water. Protein was shock frozen in liquid nitrogen and lyophilized. Protein concentrations were estimated by gel-densiometry using a bovine serum albumin (BSA) standard on SDS-PAGE and staining with SYPRO Red (Invitrogen, Karlsruhe, Germany). Protein identity was confirmed by LC-MS mass spectrometry.

8.6 Synthesis of Synthetic all-L-Polymerase Dpo4 Variant A155C by Native Chemical Ligation of the Fragments 1-154-Thioester and 155-352

The fragments 1-154-thioester and 155-352 of all-L-polymerase Dpo4 variant A155C were solved 50 µM in TRIS-buffer (pH 8.6) containing 2% Triton X100, 1% thiophenol and 5 mM tris(2-carboxyethyl)phosphine hydrochloride. The reaction mixture was shaken 72 h by room temperature. Afterwards the ligation success was analyzed by SDS-PAGE (FIG. 11A) and LC-ESI-mass spectrometry (RP18-column, gradient of ACN with 0.1% TFA in water with 0.1% TFA 5-95% in 20 mM, FIG. 11B). A clear band was found in lane around 41 kDa indicating the full length polymerase. The theoretical molecular weight ($M_{theor}$=40223 Da) corresponds the observed molecular weight ($M_{obs}$=40265 Da) as shown by ESI-MS.

8.7 Synthesis of Fragment 155-352 by Native Chemical Ligation of the Fragments 155-202-Thioester and 203-352

The fragments 155-202-thioester and 203-352 V203C of all-L-polymerase Dpo4 were solved 0.2 M in TRIS-buffer (pH 8.6) containing 2% SDS, 1% thiophenol and 5 mM tris(2-carboxyethyl)phosphine hydrochloride. The reaction mixture was shaken 72 h by room temperature. Analysis of the ligation success was performed by SDS-PAGE (FIG. 20A) and LC-ESI-mass spectrometry (RP18-column, gradient of ACN with 0.1% TFA in water with 0.1% TFA 5-95% in 20 min, FIG. 20B). A clear band was found in lane 7 around 21.5 kDa indicating the ligation product. The theoretical molecular weight ($M_{theor}$=22749 Da) corresponds the observed molecular weight ($M_{obs}$=22769 Da) as shown by ESI-MS.

Example 9—Activity Confirmation of Polymerase Dpo4 and Variants of Polymerase Dpo4 Consisting of L-Amino Acids This example describes a PCR activity test for all-L-polymerase Dpo4 and variants of all-L-polymerase Dpo4 according to example 7 and for the synthetic all-L-polymerase Dpo4 according to example 8.

9.1 Templates for PCR Activity Assay

Template for the PCR reaction is a 83-mer single-stranded D-DNA oligonucleotide (MJ_1_1_DD) from which, in the first thermal cycle, the opposite strand is made. Thereafter both strands serve as template for exponential amplification. Template DNA oligonucleotide and DNA primers are synthesized at NOXXON in D-configuration.

List of oligonucleotides for the PCR activity assay:

| Name | Length, nt | Sequence (5'→3') |
|---|---|---|
| MJ_1_1_DD | 83 | GTGGAACCGACAACTTGTGCTGCGTCCAGCAT AAGAAAGGAGCTCCCTCAGAAGAAGCTGCGCA GCGTGCCAGTCTGAGCTCC |
| DE4.40T7 | 38 | TCTAATACGACTCACTATAGGAGCTCAGACTG GCACGC |
| DE4.40R | 20 | GTGGAACCGACAACTTGTGC |

9.2 PCR Reactions

15 µl PCR reactions contained 0.2 mM each of the four D-dNTP's, 10 nM 83-mer ssDNA (MJ_1_1_DD) template, 1 µM of forward and reverse primer, 1× ThermoPol buffer (Invitrogen, 20 mM Tris-HCl, 10 mM KCl, 10 mM $(NH_4)_2SO_4$, 2 mM $MgSO_4$, 0.1% Triton X-100, pH 8.8@25° C.) and at least 0.67 ng/µl all-L-polymerase Dpo4 or a variant of all-L-polymerase Dpo4 or the synthetic all-L-polymerase Dpo4. The forward primer is DE4.40T7, the reverse primer is DE4.40R, yielding a PCR product of 102 base pairs length. The D-dNTP's were purchased from Rovalab (Teltow, Germany). Negative controls were conducted by omitting all-L-polymerase Dpo4 or a variant of all-L-polymerase Dpo4 or the synthetic all-L-polymerase Dpo4. Positive controls were conducted using commercially available all-L-dpo4 (New England Biolabs, Frankfurt am Main, Germany).

The thermal cycling program consisted of 1 cycle (85° C., 3 min) then at least 7 cycles (85° C., 30 sec/56° C., 1 min/60° C., 4 min) then hold at 4° C. 4 µl aliquots of the PCR reactions were mixed with sample loading buffer and analyzed on TBE-PAGE or on agarose gels (LONZA, Cologne, Germany). A DNA standard ladder containing, among others, a 100 bp band was applied on the gel.

9.3 Activity Confirmation

Figure 12B:
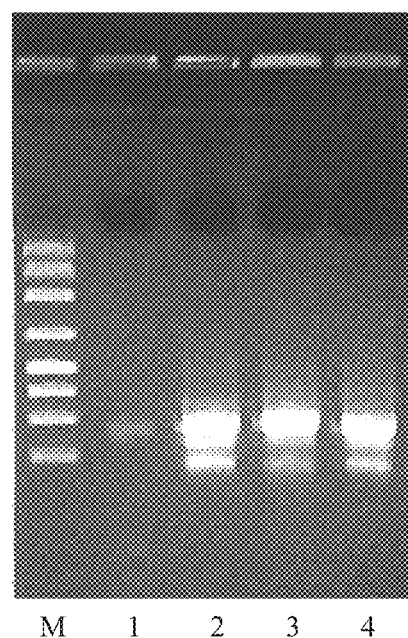

All-L-polymerase Dpo4, the variants A155C, V203C, C31S, A155C/V203C, S85C, S86C, S96C of all-L-polymerase Dpo4 and the synthetic all-L-polymerase Dpo4 were tested. All tested polymerases were able to amplify the template strand in the PCR reaction. FIG. 12A shows the analysis of PCR reactions performed with the variants A155C, V203C, C31S, A155C/V203C of all-L-polymerase Dpo4, all of which showed a band in the range of about 100 bp as compared with the DNA standard ladder. Expected PCR product size was 102 base pairs. Said band does not appear in the negative controls, where polymerase is omitted. Also said 102 bp band migrates higher than the 83-mer template. FIG. 12B shows the analysis of PCR reactions performed with the recombinant all-L-polymerase dpo4 and with the synthetic all-L-polymerase dpo4 which was made by ligation of fragments. The gel showed bands in the range of about 100 bp as compared with the DNA standard ladder. Expected PCR product size was 102 base pairs. Said band is very weak in the negative controls, where polymerase is omitted. Recombinant all-L-polymerase dpo4 and synthetic all-L-polymerase dpo4 show identical activity as can be seen when comparing lanes 2 and 3 from FIG. 12B.

Example 10—Synthesis of a Variant of Polymerase Dpo4 Consisting of D-Amino Acids Within the example the synthesis of the all-D polymerase Dpo variant A155C/V203C is described. The amino acid sequence of the all-D polymerase Dpo variant A155C/V203C is

```
Ac-MIVLFVDFDYFYAQVEEVLNPSLKGKPVVVCVFSGRFEDSGAVATAN
YEARKFGVKAGIPIVEAKKILPNAVYLPMRKEVYQQVSSRIMNLLREYSE
KIEIASIDEAYLDISDKVRDYREAYNLGLEIKNKILEKEKITVTVGISKN
KVFAKIACDMAKPNGIKVIDDEEVKRLIRELDIADVPGIGNITAEKLKKL
GINKLCDTLSIEFDKLKGMIGEAKAKYLISLARDEYNEPIRTRVRKSIGR
IVTMKRNSRNLEEIKPYLFRAIEESYYKLDKRIPKAIHVVAVTEDLDIVS
RGRTFPHGISKETAYSESVKLLQKILEEDERKIRRIGVRFSKFIEAIGLD
KFFDT-OH.
```

All amino acids used are protected according to the Solid-phase peptide synthesis Fmoc/tBu-strategy requirements (Eric Atherton et al, 1981). All amino acids used are D-amino acids (Bachem, Bubendorf, Switzerland).

10.1 Synthesis of H-D-Met-OGp(Boc)$_2$ 1 mmole Z-D-Met-OH, 0.9 eq. TBTU and 0.9 mmol HO-Gp(Boc)$_2$ were dissolved in 10 ml DMF. After addition of 2 eq. DIPEA the solution was stirred for 2 hours. After evaporating the solvent the raw product was purified with flash chromatography using DCM. Pure fractions of Z-D-Met-OGp(Boc)$_2$ were combined and the solvent was evaporated.

Z-D-Met-OGp(Boc)$_2$ was dissolved in 10 ml MeOH and flushed with argon. Hydrolytic cleavage of the N-terminal Z-group was achieved by the addition of Pd/C catalyst and H$_2$ in 2 hours. After filtrating off H-D-Met-OGp(Boc)$_2$ MeOH was evaporated under reduced pressure. Analytics was performed using reversed phase HPLC and mass spectrometry. The calculated mass of 482 Da is in accordance to the determined mass of 483 Da.

10.2 Synthesis of Fully Protected all-D-Peptide H-RTFPHGISKETAYSESVKLLQKILEEDERKIR-RIGVRFSKFIEAIGLDKFFDT-NH$_2$ (1)

0.1 mmole Fmoc-Sieber rink amide NovaSynTG resin was loaded after Fmoc-deprotection with Fmoc-D-Thr(tBu)-OH using 5 eq. amino acid, eq. 4.9 eq. HATU and 10 eq. DIPEA for 45 min in 6 ml NMP.

Automated synthesis was done using an ABI 433 with the FASTmoc protocol. 10 eq. amino acid were activated using 9 eq. HATU and 20 eq. DIPEA in NMP. Coupling time was 45 min and Fmoc-deprotection was performed three times for 7 min with 20% (v/v) piperidine in NMP. Double coupling was performed after coupling of 42 amino acids.

The cleavage of the fully protected peptide acid was achieved by incubating the peptidyl resin twice in 10 ml 1% (v/v) TFA in DCM for 2 hours. After filtering off the peptide the solvent was evaporated and the residue precipitated using ice cold diethyl ether. The precipitated peptide was isolated and dried.

The final product was characterised by HPLC and mass spectrometry (FIG. 13). The calculated mass for the product (6244 Da) corresponds to the measured mass (6249 Da).

10.3 Synthesis of Fully Protected all-D-Peptide Boc-VDTLSIEFDKLKGMIGEAKAKYLISLARDEYNEPIR-TRVRKSIGRIVTMKRNSRNLEEIK PYLFRAIEE-SYYKLDKRIPKAIHVVAVTEDLDIVSRG-OH (2)

0.10 mmole TentaGel-R-Trityl resin was loaded with Fmoc-D-Gly-OH as described in Barlos et al. (Barlos et al., 1989). Therefore 0.10 mmol resin was incubated twice for 30 min with 0.6 mmole thionylchloride and subsequently washed with DCM. Following this the resin was incubated 90 min with 0.6 mmole Fmoc-Gly-OH, 2.4 mmol DIPEA in 6 ml DCM. Afterwards the resin was blocked three times for 10 min using a solution of 10% MeOH (v/v), 10% DIPEA (v/v) in DCM and washed with DCM. Automated synthesis was done using an ABI 433 with the FASTmoc protocol. 10 eq. amino acid were activated using 9 eq. HATU and 20 eq. DIPEA in NMP. Coupling time was 45 min and Fmoc-deprotection was performed three times for 7 min with 20% (v/v) piperidine in NMP. Double coupling was performed after coupling of 39 amino acids.

The cleavage of the fully protected peptide acid was achieved by incubating the peptidyl resin twice in 10 ml 30% (v/v) HFIP in DCM for 2 hours. After filtering off the peptide the solvent was evaporated and the residue precipitated using ice cold diethyl ether. The precipitated peptide was isolated and dried. The final product was characterised by HPLC and mass spectrometry (FIG. 14). The experimentally determined mass of the product (11289 Da) was in accordance to the theoretical value (11286 Da).

10.4 Synthesis of all-D-Peptide H-VDTLSIEFDKLKG-MIGEAKAKYLISLARDEYNEPIRTRVRKSIG-RIVTMKRNSRNLEE IKPYLFRAIEE-SYYKLDKRIPKAIHVVAVTEDLDIV SRGRTFPHGISKETAYSESVKLLQ KILEEDERKIR-RIGVRFSKFIEAIGLDKFFDT-NH$_2$ (3) by Fragment Condensation of Peptide 1 with Peptide 2.

5 µmole (2) and 1 eq. (1) were dissolved in 25% (v/v) TFE in DCM. After addition of 5 eq. PyBOP and 10 eq. DIPEA the mixture was stirred overnight. After evaporating the solvent the peptide was precipitated using ice cold diethyl ether and filtered off.

The cleavage of the side chain protection groups of the peptide was performed with 2.5% EDT, 2.5% water, 2.5% TIS in TFA for 2 hours. Following the evaporation of TFA the peptide was precipitated with ice cold diethyl ether. Reversed phase HPLC purification of the N-terminal Fmoc-protected peptide was performed on a C18 column using an ACN/water gradient. Fractions that contain product were combined and freeze dried.

The final product was characterised by HPLC and mass spectrometry (FIG. 15). The experimentally determined mass (17531 Da) corresponds to the theoretical molecular mass (17512 Da).

10.5 Synthesis of all-D-Peptide Z-CDMAKPNGIKVID-DEEVKRLIRELDIADVPGIGNITAEKLKKLGINKL-benzyl-thioester (4)

0.10 mmole TentaGel-R-Trityl resin was loaded with Fmoc-D-Leu-OH as described in Barlos et al. (Barlos et al., 1989). Therefore 0.10 mmol resin was incubated twice for 30 min with 0.6 mmole thionylchloride and subsequently washed with DCM. Following this the resin was incubated 90 min with 0.6 mmole Fmoc-D-Leu-OH, 2.4 mmol DIPEA in 6 ml DCM. Afterwards the resin was blocked three times for 10 min using a solution of 10% MeOH (v/v), 10% DIPEA (v/v) in DCM and washed with DCM. Automated synthesis was done using an ABI 433 with the FASTmoc protocol. 10 eq. amino acid were activated using 9 eq. HATU and 20 eq. DIPEA in NMP. Coupling time was 45 min and Fmoc-deprotection was performed three times for 7 min with 20% (v/v) piperidine in NMP.

The cleavage of the fully protected peptide acid was achieved by incubating the peptidyl resin twice in 10 ml 30% (v/v) HFIP in DCM for 2 hours. After filtering off the peptide the solvent was evaporated and the residue precipitated using ice cold diethyl ether. The precipitated peptide was isolated and dried.

Figure 16B:
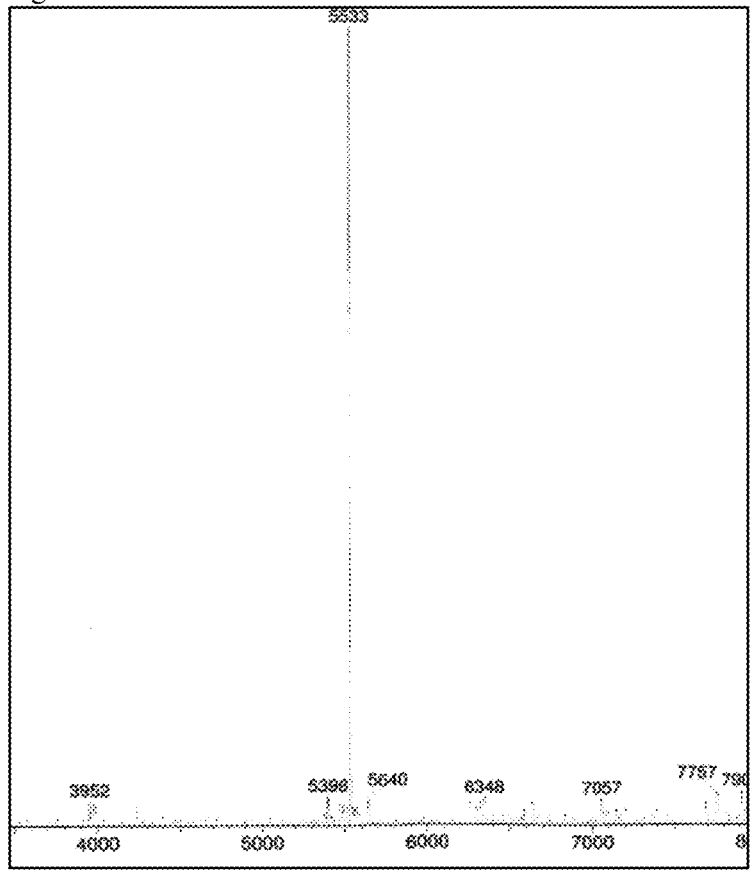

The N-terminal Z- and completely side chain protected peptide 4 was solved 1 mM in DMF. After addition of 5 eq. PyBOP, 10 eq. DIPEA and 30 eq. benzyl mercaptan the mixture was stirred for 4 h. Then the DMF was evaporated, the peptide was precipitated and washed with ice-cold diethyl ether. The side chain protecting groups were removed by treatment with 2.5% EDT, 2.5% water, 2.5% TIS in TFA for 2 hours. After the evaporation of TFA the peptide was precipitated and washed with ice cold diethyl ether. The peptide-benzyl-thioester was then purified by reversed-phase HPLC and analyzed by reversed-phase HPLC (FIG. 16A) and ESI-MS (FIG. 16B). The theoretical molecular weight ($M_{theor}$=5527 Da) corresponds the observed molecular weight ($M_{obs}$=5533 Da) as shown by ESI-MS.

10.6 Synthesis of all-D-Peptide H-RKEV-YQQVSSRIMNLLREYSEKIEIASIDEAYLDIS-DKVRDYREAYNLGLEIKNKILE KEKITVTV-GISKNKVFAKIA-SMe (7)

0.10 mmole TentaGel-R—NH$_2$ resin was loaded with Fmoc-D-Ala-OH using 5 eq. amino acid, eq. 4.9 eq. HATU and 10 eq. DIPEA for 45 min in 6 ml NMP. Subsequently the resin was washed with THF. Conversion to Fmoc-D-Ala-Ψ[CS—NH]R-TentaGel was achieved by incubation with 4 eq. Lawesson reagent in THF at 80° C. for 2 hours. Following this the resin was washed with NMP. Subsequently the so prepared resin was used in automated peptide synthesis as described previously (ABI 433, FASTmoc protocol, 10 eq. amino acid were activated using 9 eq. HATU and 20 eq. DIPEA in NMP; coupling time was 45 min and Fmoc-deprotection was performed three times for 7 min with 20% (v/v) piperidine in NMP). Double coupling steps were performed after 44 coupled amino acids.

Following this the corresponding thioester was generated by incubation with methyl iodide in DMF overnight according to Sharma et al. (Sharma et al, 2011). After filtering of the resin the peptide thioester containing solvent was evaporated and the residue precipitated using ice cold diethyl ether. The cleavage of side chain protection groups was performed with 2.5% EDT, 2.5% water, 2.5% TIS in TFA for 2 hours. Following the evaporation of TFA the peptide was precipitated with ice cold diethyl ether. Reversed phase HPLC purification of the peptide thioester was performed on a C18 column using an ACN/water gradient. Fractions that contain product were combined and freeze dried.

Figure 17B:
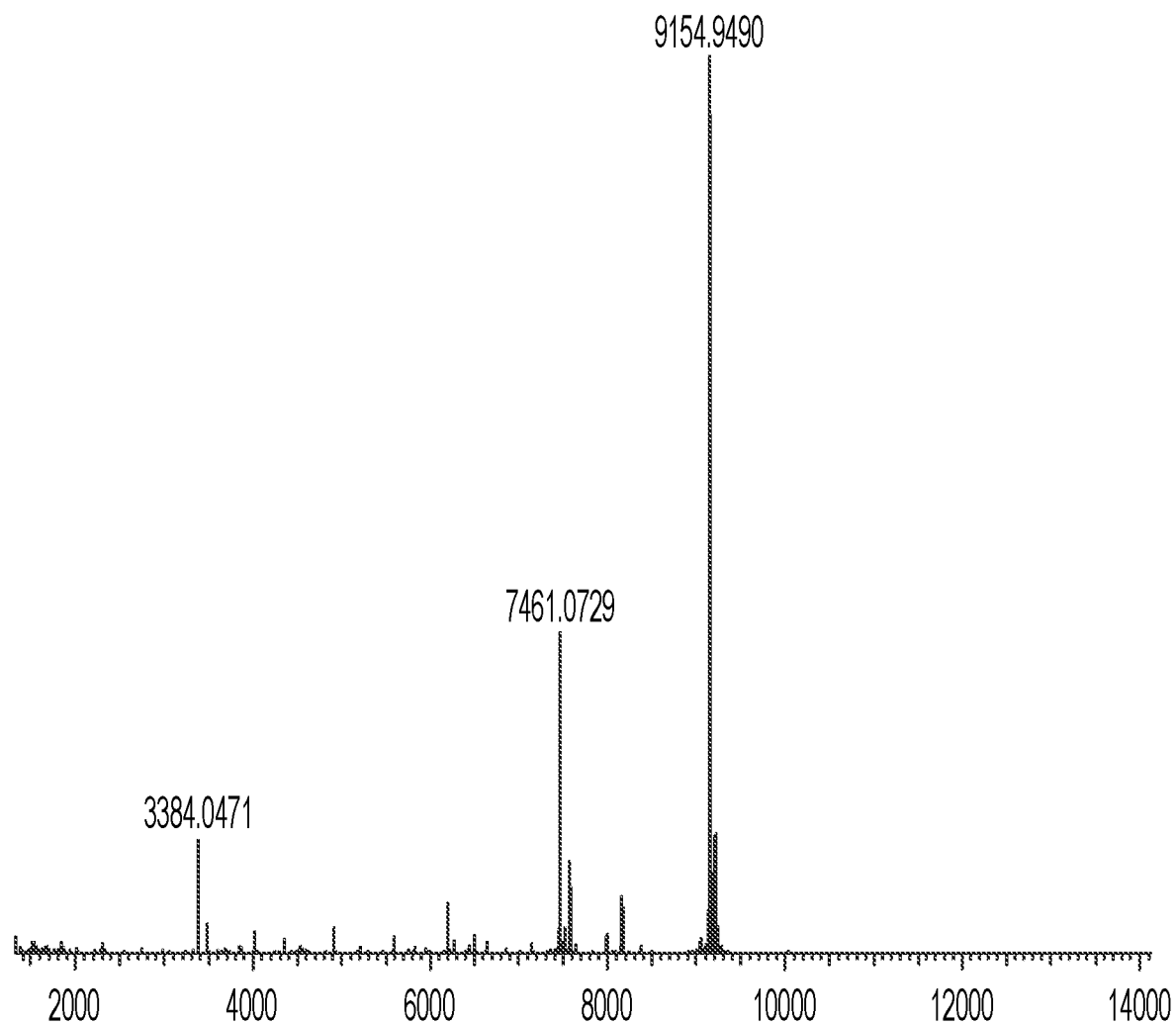

The final product was characterised by HPLC (FIG. 17A) and mass spectrometry (FIG. 17B). The molecular mass of the product determined by mass spectrometry (9155 Da) was in accordance to the calculated mass (9150 Da).

10.7 Synthesis of Ac-MIVLFVDFDYFYAQVEEVLNPSLKGKPVVVCVFS-GRFEDSGAVATANYEARKFG VKAGIPIVEAKKILP-NAVYLPM-OGp (6)

0.10 mmole TentaGel-R-Trityl resin was loaded with Fmoc-D-Pro-OH as described in Barlos et al. (Barlos et al., 1989). Therefore 0.10 mmol resin was incubated twice for 30 min with 0.6 mmole thionylchloride and subsequently washed with DCM. Following this the resin was incubated 90 min with 0.6 mmole Fmoc-D-Pro-OH, 2.4 mmol DIPEA in 6 ml DCM. Afterwards the resin was blocked three times for 10 min using a solution of 10% MeOH (v/v), 10% DIPEA (v/v) in DCM and washed with DCM. Automated synthesis was done using an ABI 433 with the FASTmoc protocol. 10 eq. amino acid were activated using 9 eq. HATU and 20 eq. DIPEA in NMP. Coupling time was 45 min and Fmoc-deprotection was performed three times for 7 min with 20% (v/v) piperidine in NMP. Double coupling was performed after coupling of 46 amino acids. Acetylation of the N-terminus was performed with 10% (v/v) acetic anhydride and 10% (v/v) DIPEA in DMF three times for 10 min.

The cleavage of the fully protected peptide acid was achieved by incubating the peptidyl resin twice in 10 ml 30% (v/v) HFIP in DCM for 2 hours. After filtering off the peptide the solvent was evaporated and the residue precipitated using ice cold diethyl ether. The precipitated peptide was isolated and dried.

0.01 mmole fully protected peptide, 4 eq. PyBOP and 5 eq. H-D-Met-OGp(Boc)$_2$ were dissolved in 6 ml NMP. After addition of 10 eq. DIPEA the mixture was stirred for 4 hours. Following this the solvent was reduced evaporated and the residue precipitated by ice cold diethyl ether. The precipitated peptide ester was dried and subsequently protection groups were cleaved off using 2.5% EDT, 2.5% water, 2.5% TIS in TFA for 2 hours. Following the evaporation of TFA the peptide was precipitated with ice cold diethyl ether. Reversed phase HPLC purification of the peptide ester was performed on a C18 column using an ACN/water gradient. Fractions that contain product were combined and freeze dried.

Figure 18B:
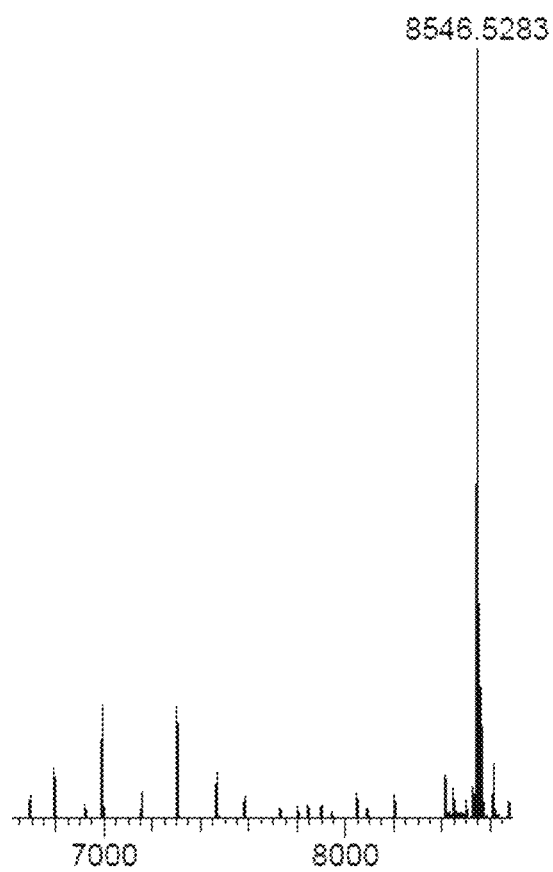

The final product was characterised by HPLC (FIG. 18A) and mass spectrometry (FIG. 18B). The experimentally determined mass (8547 Da) corresponded to the theoretical molecular mass (8541 Da).

10.8 Synthesis of all-D-Peptide H-CDMAKPNGIKVID-DEEVKRLIRELDIADVPGIGNITAEKLKKLGIN-KLCDTLSIEFDK LKGMIGEAKAKYLIS-LARDEYNEPIRTRVRKSIGRIVTMKRNSRNLEEIKPYL-FRAIEES YYKLDKRIPKAIHVVAVTEDLDIVSRGRTFPHGIS-KETAYSESVKLLQKILEEDERKIRR IGVRFSK-FIEAIGLDKFFDT-OH (5) by Native Chemical Ligation of Peptide 4 with Peptide 3

Both peptides 3 and 4 are solved 0.2 M in TRIS-buffer (pH 8.6) containing 2% SDS, 1% thiophenol and 5 mM tris(2-carboxyethyl)phosphine hydrochloride. The reaction mixture shaked 72 h by room temperature. Afterwards the mixture is purified is by reversed-phase HPLC. For removal of the N-terminal Z-protecting group the peptide was solved in 270 eq. TFA and 50 eq. thioanisol and shakes for 6 h at room temperature (Yoshiaki Kiso et. al., 1980). After evaporation of TFA the peptide was precipitated and washed by ice-cold diethyl ether and purified again by reversed-phase HPLC (Phenomenex, Aschaffenburg, Germany). Analysis of the free peptide 5 is performed by SDS-PAGE, reversed phase UPLC and ESI-mass spectrometry. The correct mass of the product is found.

10.9 Synthesis of all-D-Peptide Ac-MIVLFVDFDYFYAQVEEVLNPSLKGKPVVVCVFS-GRFEDSGAVATANYEARKFG VKAGIPIVEAKKILP-NAVYLPMRKEVYQQVSSRIMNLLREYSEKIEIASIDE-AYLDISDK VRDYREAYNLGLEIKNKILEKEKITVTVGISKNKVFA-KIA-SMe (8) by Protease-Catalyzed Ligation of Peptide 6 with Peptide 7

Surprisingly, the synthetic all-D polymerase Dpo4 variant A155C/V203C is active without extra refolding efforts and thus is used without further refolding procedure. Protein concentration is estimated by sodium dodecyl sulphate (abbr. SDS) polyacrylamide gel electrophoresis (abbr. PAGE) on pre-cast gels (Invitrogen, Karlsruhe, Germany) using a standard series of known protein concentrations followed by SYPRO-RED staining (Invitrogen, Karlsruhe, Germany) and densiometric band analysis on a BioRad Fx scanner instrument.

11.1 Templates for PCR Activity Assay

Template for the PCR reaction is a 83-mer single-stranded L-DNA oligonucleotide (MJ_1_105_LD) from which, in the first thermal cycle, the opposite strand is made. Thereafter both strands serve as template for exponential amplification. Template DNA oligonucleotide and DNA primers are synthesized at NOXXON in L-configuration.

List of oligonucleotides for PCR activity assay:

| Name | Length, nt | Configuration | Sequence (5'→3') |
|---|---|---|---|
| MJ_1_105_LD | 83 | L | GTGGAACCGACAACTTGTGCTGCGTCCAGCATAAGA AAGGAGCTCCCTCAGAAGAAGCTGCGCAGCGTGCCA GTCTGAGCTCC |
| MJ_oligo_187_LD | 38 | L | TCTAATACGACTCACTATAGGAGCTCAGACTGGCAC GC |
| MJ_oligo_189_LD | 20 | L | GTGGAACCGACAACTTGTGC |

Figure 19B:
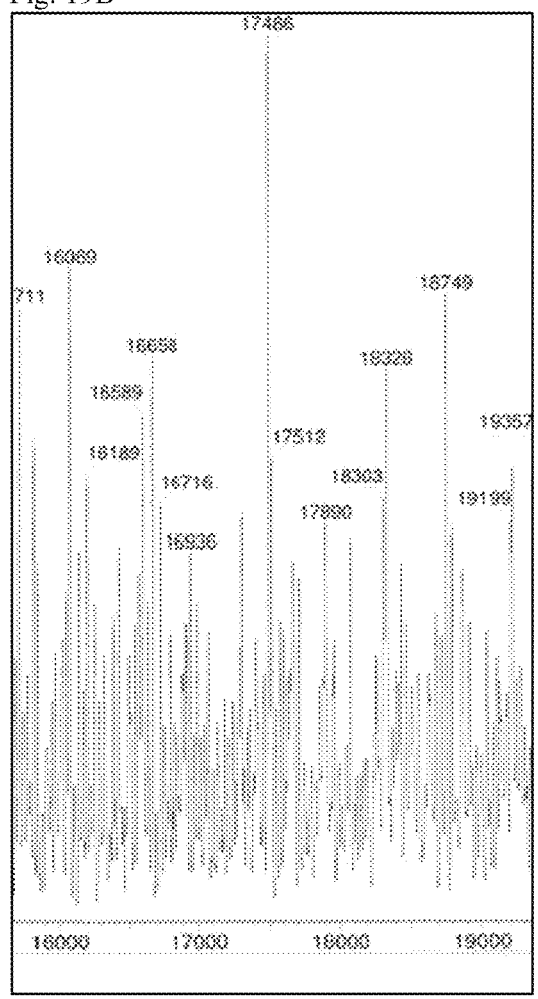

Peptide 6 was solved 0.2 mM and peptide 7 was solved 0.6 mM in sodium-phosphate buffer (100 mM, pH 8.5, with 100 mM NaCl) containing 4 M Urea. After addition of 20 µM Clostripain (Endoprotease Arg-C, Worthington Biochemical Corporation, Lakewood, N.J., USA) the reaction mixture was shaken overnight at 37° C. The precipitated peptides were centrifuged, solved in H$_2$O/Formic Acid 80/20 and will be purified by reversed phase HPLC using a RP-18-column (Phenomenex, Aschaffenburg, Germany) with a gradient of ACN in water of 5% to 95% within 30 min. The final peptide was analyzed by SDS-PAGE (FIG. 19A) and ESI-mass spectrometry (FIG. 19B). A band was found in lane 1 between 14.4 kDa and 21.5 kDa indicating the ligation product. The theoretical molecular weight of the ligation product ($M_{theor}$=17476 Da) corresponds the observed molecular weight ($M_{obs}$=17486 Da) as shown by ESI-MS.

10.10 Synthesis of the all-D Polymerase Dpo Variant A115C/V203C by Native Chemical Ligation of Peptide 8 with Peptide 5

Both peptides 5 and 8 are solved 0.2 M in TRIS-buffer (pH 8.6) containing 2% Triton X100, 1% thiophenol and 5 mM tris(2-carboxyethyl)phosphine hydrochloride. The reaction mixture shakes 72 h by room temperature. Afterwards the mixture is purified by reversed-phase HPLC and analyzed by SDS-PAGE, reversed phase UPLC and ESI-mass spectrometry. The correct mass of the ligation product is found.

Example 11—Activity Confirmation of Synthetic Polymerase Dpo4 Consisting of D-Amino Acids This example describes a PCR activity test for all-D polymerase Dpo4 variant A155C/V203C according to example 10.

11.2 PCR Reactions

15 µl PCR reactions contain 0.2 mM each of the four L-dNTP's, 10 nM 83-mer ssDNA (MJ_1_105_LD) template, 1 µM of forward and reverse primer, 1× ThermoPol buffer (Invitrogen, 20 mM Tris-HCl, 10 mM KCl, 10 mM (NH$_4$)$_2$SO$_4$, 2 mM MgSO$_4$, 0.1% Triton X-100, pH 8.8@25° C.) and at least 0.67 ng/µl all-D polymerase Dpo4 variant A155C/V203C. The forward primer is MJ_oligo_187_LD yielding a PCR product of 102 bp, which is distinguishable from the 83-mer template. The reverse primer is MJ_oligo_189_LD. The L-dNTP's are purchased as custom synthesis by Rasayan, Inc. (Encinitas, Calif., USA).

Negative controls are conducted by omitting the all-D polymerase Dpo4 variant A155C/V203C.

The thermal cycling program consists of 1 cycle (85° C., 3 min) then at least 7 cycles (85° C., 30 sec/56° C., 1 min/60° C., 4 min) then hold at 4° C. 4 µl aliquots of the PCR reactions are mixed with sample loading buffer and analyzed on TBE gels. A DNA standard ladder containing, among others, a 100 bp band is applied on the gel.

11.3 Activity Confirmation

The PCR reaction with all-D polymerase Dpo4 variant A155C/V203C and L-DNA substrate and L-nucleotides yields a band in the range of about 100 bp as compared with the DNA standard ladder. Said band does not appear in the negative controls, where polymerase is omitted. Also said 102 bp band migrates higher than the 83-mer template. The all-D polymerase Dpo4 variant A155C/V203C dependent appearance of an L-DNA amplification product thus confirms the activity of the synthetic all-D polymerase Dpo4 variant A155C/V203C in a thermal amplification process.

Example 12—Synthesis of D- or L-Nucleic Acids

L-DNA nucleic acids or D-DNA nucleic acids were produced by solid-phase synthesis with an ABI 394 synthesizer (Applied Biosystems, Foster City, Calif., USA) using 2'TBDMS DNA phosphoramidite chemistry with standard exocyclic amine protecting groups (Damha and Ogilvie, 1993). For the DNA synthesis dA(N-Bz)-, dC(N—Ac)—, dG(N-ibu)-, and dT in the D- and L-configuration were applied. All phosphoramidites were purchased from Chem-Genes, Wilmington, Mass. After synthesis and deprotection L-DNA nucleic acids or D-DNA nucleic acids were purified by gel electrophoresis.

REFERENCES

The complete bibliographic data of the documents recited herein are, if not indicated to the contrary, as follows, whereby the disclosure of said references is incorporated herein by reference.

Altschul S. F., Gish W., et al. (1990) Basic local alignment search tool. J Mol Biol. 215(3):403-10.

Altschul S. F., Madden T. L., et al. (1997) Gapped BLAST and PSI-BLAST: a new generation of protein database search programs. Nucleic Acids Res. 25(17):3389-402.

Atherton E., Logan C. J. and Sheppard R. C. (1981) Peptide synthesis. Part 2. Procedures for solid-phase synthesis using Nα-fluorenylmethoxycarbonylamino-acids on polyamide supports. Synthesis of substance P and of acyl carrier protein 65-74 decapeptide J. Chem. Soc., Perkin Trans. 1, 538-546

Barlos, K., Gatos, D., Kallitsis, J., Papaphotiu, G., Sotiriu, P., Yao, W. Q. and Schäfer, W. (1989) Darstellung geschützter Peptid-Fragmente unter Einsatz substituierter Triphenylmethyl-Harze. Tetrahedron Letters. 30(30): 3943-3946

Bock L. C., Griffin L. C., Latham J. A., Vermaas E. H. and Toole J. J. (1992) Selection of single-stranded DNA molecules that bind and inhibit human thrombin. Nature. 355(6360):564-6.

Boudsocq, F., S. Iwai, et al. (2001). "Sulfolobus solfataricus P2 DNA polymerase IV (Dpo4): an archaeal DinB-like DNA polymerase with lesion-bypass properties akin to eukaryotic poleta." Nucleic Acids Res 29(22): 4607-16.

Burmeister P. E. et al (2006) 2'-Deoxy purine, 2'-O-methyl pyrimidine (dRmY) aptamers as candidate therapeutics. Oligonucleotides. 16(4):337-51.

Damha M J, Ogilvie K K. (1993) Oligoribonucleotide synthesis. The silyl-phosphoramidite method. Methods Mol Biol. 20:81-114

Ellington A. D. and Szostak J. W. (1990) In vitro selection of RNA molecules that bind specific ligands. Nature. 346(6287):818-22.

Freier S. M. and Altmann K. H. (1997) The ups and downs of nucleic acid duplex stability: structure-stability studies on chemically-modified DNA:RNA duplexes. Nucleic Acids Res. 25(22):4429-43.

Klussmann S. (2006). The Aptamer Handbook—Functional Oligonucleotides and their Applications. Edited by S. Klussmann. WILEY-VCH, Weinheim, Germany, ISBN 3-527-31059-2

Klussmann S., Nolte A., Bald R., Erdmann V. A. and Fürste J. P. (1996) Mirror-image RNA that binds D-adenosine. Nat Biotechnol. 14(9):1112-5.

Kusser W. (2000) Chemically modified nucleic acid aptamers for in vitro selections: evolving evolution. J Biotechnol 74(1): 27-38.

Mairal T., Ozalp V. C., Lozano Sanchez P., et al. (2008) Aptamers: molecular tools for analytical applications. Anal Bioanal Chem. 390(4):989-1007

Mandal K., Uppalapati M., Ault-Riché D., Kenney J., Lowitz J., Sidhu S. S. and Kent S. B. H. (2012) Chemical synthesis and X-ray structure of a heterochiral {D-protein antagonist plus vascular endothelial growth factor} protein complex by racemic crystallography. PNAS. 109(37)

McGinnis S., Madden T. L. et al. (2004) BLAST: at the core of a powerful and diverse set of sequence analysis tools. Nucleic Acids Res. 32(Web Server issue): W20-5.

Needleman and Wunsch (1970) A general method applicable to the search for similarities in the amino acid sequence of two proteins. J Mol Biol. 48(3):443-53.

Nolte A., Klussmann S., Bald R., Erdmann V. A. and Furste J. P. (1996) Mirror-design of L-oligonucleotide ligands binding to L-arginine. Nat Biotechnol. 14(9):1116-9.

Oliveros, M., R. J. Yanez, et al. (1997). "Characterization of an African swine fever virus 20-kDa DNA polymerase involved in DNA repair." J Biol Chem 272(49): 30899-910.

Pearson and Lipman (1988) Improved tools for biological sequence comparison. Proc. Nat'l. Acad. Sci. USA 85: 2444

Sambrook et al. (ed.), (1989) Molecular Cloning: A Laboratory Manual, 2nd ed., vol. 1-3, Cold Spring Harbor Laboratory Press, Cold Spring Harbor, N.Y.

Sekizaki, H., Itoh, K., Toyota, E. and Tanizawa, K. (1996) Synthesis and tryptic hydrolysis of p-guanidinophenyl esters derived from amino acids and peptides. Chemical & Pharmaceutical Bulletin. 44(8):1577-9

Sekizaki, H., Itoh, K., Toyota, E. and Tanizawa, K. (1996) Trypsin-catalyzed peptide synthesis and various p-guanidinophenyl esters as acyl donors. Chemical & Pharmaceutical Bulletin. 44(8):1585-7

Sharma, I. and Crich, D. (2011) Direct Fmoc-Chemistry-Based Solid-Phase Synthesis of Peptidyl Thioesters. Journal of Organic Chemistry. 76(16):6518-24

Smith and Waterman (1981), Adv. Appl. Math. 2: 482

Tuerk C. and Gold L. (1990) Systematic evolution of ligands by exponential enrichment: RNA ligands to bacteriophage T4 DNA polymerase. Science. 249(4968):505-10.

Usman N. and Cedergren R. (1992) Exploiting the chemical synthesis of RNA. Trends Biochem Sci. 17(9):334-9

Venkatesan N., Kim S. J., et al. (2003) Novel phosphoramidite building blocks in synthesis and applications toward modified oligonucleotides. Curr Med Chem 10(19): 1973-91

Wincott F, DiRenzo A, et al. (1995). Synthesis, deprotection, analysis and purification of RNA and ribozymes. Nucleic Acids Res.; 23(14):2677-84.

The features of the present invention disclosed in the specification, the claims and/or the drawings may both separately and in any combination thereof be material for realizing the invention in various forms thereof.

The invention claimed is:

1. A protein comprising a polymerase activity exhibiting moiety, wherein the polymerase activity exhibiting moiety of said protein consists of an amino acid sequence of between 300 and 360 amino acids, wherein amino acids of the amino acid sequences are D-amino acids, wherein the polymerase activity adds one or more L-nucleotides to the 3' end of a first L-nucleic acid.

2. The protein according to claim 1, wherein the protein is thermostable.

3. The protein according to claim 1, wherein the protein comprises DNA-polymerase activity.

4. The protein according to claim 3, wherein the DNA-polymerase activity is a DNA-dependent DNA-polymerase activity.

5. The protein according to claim 1, wherein the polymerase activity exhibiting moiety comprises *Sulfolobus solfataricus* DNA polymerase.

6. A method for adding one or more L-nucleotides to the 3' end of a first L-nucleic acid, wherein the method comprises the step of reacting the one or more L-nucleotides with the first L-nucleic acid in the presence of the protein of claim 1 comprising a polymerase activity exhibiting moiety, wherein the polymerase activity adds one or more L-nucleotides to the 3' end of the first L-nucleic acid.

7. The method according to claim 1, wherein the first L-nucleic acid is a primer consisting of DNA, RNA, modified DNA, modified RNA or combinations thereof.

8. The method according to claim 1, wherein the reaction further comprises a second L-nucleic acid, wherein one molecule of the first L-nucleic acid is hybridized to one molecule of the second L-nucleic acid.

9. The method according to claim 8, wherein the polymerase activity exhibiting moiety synthesizes a third L-nucleic acid that is complementary to the second L-nucleic acid, wherein the third L-nucleic acid comprises the first L-nucleic acid and the L-nucleotides added to the 3' end of the first L-nucleic acid.

10. A method for amplifying a target L-nucleic acid comprising contacting said target L-nucleic acid with at least one primer under conditions allowing hybridization of said at least one primer to said target L-nucleic acid and extending said primer with the protein of claim 1 comprising a polymerase activity exhibiting moiety, wherein the polymerase activity adds in the presence of L-nucleotides, one or more L-nucleotides to said primer.

11. The method according to claim 10, wherein the at least one primer consists of L-nucleotides and optionally a modification.

12. The method according to claim 10, wherein said method uses two primers, wherein at least one of said two primers consists of L-nucleotides and optionally a modification.

13. A method for identifying a target molecule binding L-nucleic acid molecule comprising the following steps of:
(a) generating a heterogeneous population of L-nucleic acid molecules;
(b) contacting the heterogeneous population of L-nucleic acid molecules of step (a) with the target molecule;
(c) separating L-nucleic acid molecules which are not bound by the target molecule; and
(d) amplifying L-nucleic acid molecules which are bound by the target molecule, wherein the amplifying step uses the protein according to claim 1,
wherein the protein consists of an amino acid sequence, wherein amino acids of the amino acid sequence are D-amino acids.

14. The method according to claim 13, further comprising the step of:
(e) sequencing the L-nucleic acid molecules which are bound by the target molecule; and
(f) synthesizing nucleic acid molecules, the nucleotide sequence of which is identical to the nucleotide sequence of the L-nucleic acid molecules sequenced in step (e).

15. The method according to claim 14, wherein after step (d) the following step is introduced:
(da) contacting the amplified nucleic acid molecules with the target molecule, wherein step (b) and optionally steps (c) and/or (d) are carried out prior to step (e), wherein steps (da), (b), (c) and optionally (d) are carried out in that order one or several times.

16. The method according to claim 13, wherein nucleic acid molecules of the heterogeneous population of L-nucleic acid molecules of step (a) comprise a 5' end and a 3' end primer binding site and, sequences which are complementary to said 3' end and to said 5' primer binding sites which allow amplification of the L-nucleic acid molecules obtained in step (d) by a polymerase chain reaction, wherein primers used in the polymerase chain reaction consist of L-nucleotides, and nucleotides used in the polymerase chain reaction are L-nucleotides.

17. A method for producing the protein according to claim 1, wherein
a) two or more fragments of the protein according to claim 1 are chemically synthesized, whereby the two or more fragments in entirety form the protein, and
b) the two or more fragments of step a) are ligated to each other by segment condensation, native chemical ligation, enzymatic ligation or combinations thereof,
wherein the protein consists of D-amino acids.

18. The method for producing a protein according to claim 17, wherein enzyme used in enzymatic ligation is Clostripain.

* * * * *